United States Patent
Shibata et al.

(10) Patent No.: US 10,158,080 B2
(45) Date of Patent: Dec. 18, 2018

(54) AMINO FLUORENE POLYMER AND ORGANIC LIGHT-EMITTING DEVICE INCLUDING THE SAME

(71) Applicant: SAMSUNG ELECTRONICS CO., LTD., Suwon-si, Gyeonggi-do (KR)

(72) Inventors: Katsunori Shibata, Kanagawa (JP); Norihito Ishii, Kanagawa (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 227 days.

(21) Appl. No.: 15/251,312

(22) Filed: Aug. 30, 2016

(65) Prior Publication Data

US 2017/0062724 A1    Mar. 2, 2017

(30) Foreign Application Priority Data

Sep. 1, 2015 (JP) .................................. 2015-171690
Jan. 13, 2016 (KR) ........................ 10-2016-0004403

(51) Int. Cl.
*H01L 51/50* (2006.01)
*H01L 51/00* (2006.01)
(Continued)

(52) U.S. Cl.
CPC ........ *H01L 51/0039* (2013.01); *C07C 13/567* (2013.01); *C07C 211/61* (2013.01);
(Continued)

(58) Field of Classification Search
USPC ................ 428/690, 917; 313/504, 505, 506; 257/40, E51.05, E51.026, E51.032,
(Continued)

(56) References Cited

U.S. PATENT DOCUMENTS 7,897,269 B2   3/2011   Kambe et al.
8,562,870 B2  10/2013   McCulloch et al.
(Continued)

FOREIGN PATENT DOCUMENTS

JP    1995-090255 A    4/1995
JP    1996-054833 A    2/1996
(Continued)

OTHER PUBLICATIONS

Extended European Search Report dated Jan. 19, 2017, issued by the European Patent Office for Patent Application No. 16185561.4-1302.

*Primary Examiner* — Gregory D Clark
(74) *Attorney, Agent, or Firm* — Cantor Colburn LLP

(57) ABSTRACT

An amino fluorene polymer including a first repeating unit represented by Formula 1:

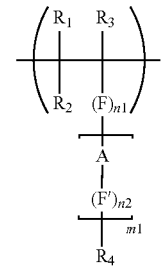

Formula 1 wherein, in Formula 1, A, F, F', m1, n1, n2, $R_1$, $R_2$, $R_3$, and $R_4$ are the same as described in the specification.

20 Claims, 1 Drawing Sheet

(51) Int. Cl.
*C07C 211/61* (2006.01)
*C08G 61/12* (2006.01)
*C07C 13/567* (2006.01)
*C08F 12/28* (2006.01)
*C08F 12/32* (2006.01)
*C08F 212/14* (2006.01)
*C09D 125/18* (2006.01)

(52) U.S. Cl.
CPC .............. *C08F 12/28* (2013.01); *C08F 12/32* (2013.01); *C08F 212/14* (2013.01); *C08G 61/128* (2013.01); *C09D 125/18* (2013.01); *H01L 51/0043* (2013.01); *C07C 2602/06* (2017.05); *C07C 2603/18* (2017.05); *C08G 2261/12* (2013.01); *C08G 2261/224* (2013.01); *C08G 2261/228* (2013.01); *C08G 2261/312* (2013.01); *C08G 2261/3142* (2013.01); *C08G 2261/3162* (2013.01); *C08G 2261/342* (2013.01); *C08G 2261/512* (2013.01); *C08G 2261/59* (2013.01); *C08G 2261/95* (2013.01); *H01L 51/5056* (2013.01)

(58) Field of Classification Search
USPC .... 257/E51.052; 564/26, 426, 432, 433, 434
See application file for complete search history.

(56) References Cited

U.S. PATENT DOCUMENTS

| | | | | |
|---|---|---|---|---|
| 2004/0170863 | A1* | 9/2004 | Kim | .................. C07C 13/72 |
| | | | | 428/690 |
| 2005/0208331 | A1* | 9/2005 | Maeda | ............... C09K 19/3847 |
| | | | | 428/690 |
| 2006/0040137 | A1 | 2/2006 | Kambe et al. | |
| 2006/0151782 | A1 | 7/2006 | Holmes et al. | |
| 2008/0154005 | A1 | 6/2008 | Suzuki et al. | |
| 2012/0001127 | A1 | 1/2012 | Brown et al. | |
| 2014/0138661 | A1 | 5/2014 | Ludemann et al. | |
| 2015/0094437 | A1 | 4/2015 | Caille et al. | |
| 2015/0108408 | A1 | 4/2015 | Eckes et al. | |

FOREIGN PATENT DOCUMENTS

| | | | | |
|---|---|---|---|---|
| JP | 1996-269133 | A | 10/1996 | |
| JP | 2000-150169 | A | 5/2000 | |
| JP | 2001-098023 | A | 4/2001 | |
| JP | 2002-110359 | A | 4/2002 | |
| JP | 2003-313240 | A | 11/2003 | |
| JP | 2004-059743 | A | 2/2004 | |
| JP | 2004-303490 | A | 10/2004 | |
| JP | 2005-054077 | A | 3/2005 | |
| JP | 2005-232097 | * | 9/2005 | ........... C08C 211/61 |
| JP | 2006-059878 | A | 3/2006 | |
| JP | 2006-237592 | A | 9/2006 | |
| JP | 2007-101807 | * | 4/2007 | |
| JP | 2008-198989 | A | 8/2008 | |
| JP | 2008198989 | | 8/2008 | |
| JP | 2008-218983 | A | 9/2008 | |
| JP | 2012111719 | A | 6/2012 | |
| JP | 2015-519424 | A | 7/2015 | |
| KR | 10-2003-0032306 | A | 4/2003 | |
| KR | 10-2014-0128878 | A | 11/2014 | |
| KR | 10-2015-0008119 | A | 1/2015 | |
| WO | 2005-020642 | A1 | 3/2005 | |
| WO | 2014132636 | A1 | 9/2014 | |

* cited by examiner

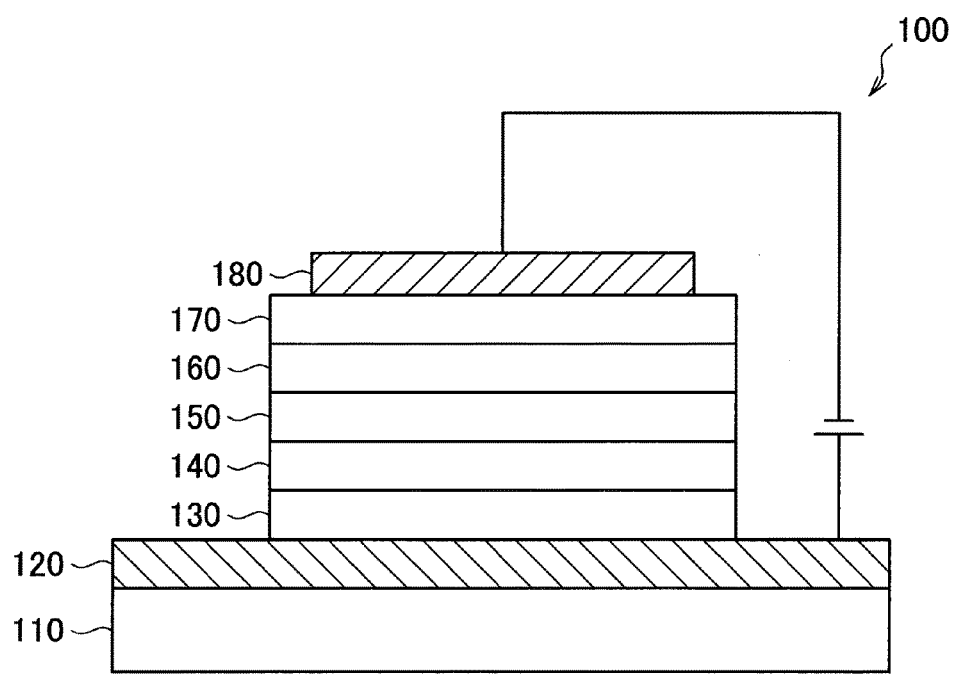

AMINO FLUORENE POLYMER AND ORGANIC LIGHT-EMITTING DEVICE INCLUDING THE SAME

CROSS-REFERENCE TO RELATED APPLICATION

This application claims priority to Japanese Patent Application No. 2015-171690, filed on Sep. 1, 2015, in Japan Patent Office, and Korean Patent Application No. 10-2016-0004403, filed on Jan. 13, 2016, in the Korean Intellectual Property Office, and all the benefits accruing therefrom under 35 U.S.C. § 119, the contents of which are incorporated herein in their entirety by reference.

BACKGROUND

1. Field

The present disclosure relates to an amino fluorene polymer and an organic light-emitting device including the amino fluorene polymer.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers such as holes and electrons are recombined in the emission layer to produce excitons. These excitons change from an excited state to a ground state to thereby generate light.

Various types of organic light emitting devices are known. However, there still remains a need in OLEDs having low driving voltage, high efficiency, high brightness, and long lifespan.

SUMMARY

Provided are an amino fluorene polymer and an organic light-emitting device including the amino fluorene polymer.

Additional aspects will be set forth in part in the description which follows and, in part, will be apparent from the description, or may be learned by practice of the presented embodiments.

According to an aspect of an embodiment, an amino fluorene polymer includes a first repeating unit represented by Formula 1:

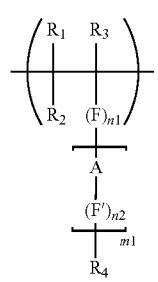

Formula 1 wherein, in Formula 1, $R_1$ to $R_3$ are each independently selected from a hydrogen atom, a substituted or unsubstituted $C_1$-$C_{10}$ alkyl group, and a substituted or unsubstituted $C_6$-$C_{30}$ aryl group;

m1 is an integer from 1 to 20;

F and F' are each independently selected from a substituted or unsubstituted azafluorenylene group and a substituted or unsubstituted fluorenylene group;

n1 and n2 are each independently selected from 1 and 2;

A is a group represented by Formula 2;

$R_4$ is selected from a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, $-Si(Q_1)(Q_2)(Q_3)$, and $-N(Q_1)(Q_2)$;

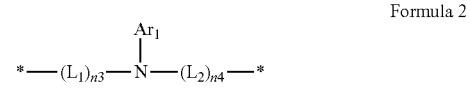

Formula 2 wherein, in Formula 2, $L_1$ and $L_2$ are each independently selected from a single bond, a substituted or unsubstituted $C_1$-$C_{20}$ alkylene group, a substituted or unsubstituted $C_3$-$C_{16}$ cycloalkylene group, a substituted or unsubstituted $C_6$-$C_{30}$ arylene group, a substituted or unsubstituted $C_1$-$C_{20}$ oxyalkylene group, a substituted or unsubstituted $C_3$-$C_{16}$ oxycycloalkylene group, a substituted or unsubstituted $C_6$-$C_{30}$ oxyarylene group, a substituted or unsubstituted $C_7$-$C_{40}$ aralkylene group, a substituted or unsubstituted $C_5$-$C_{30}$ heteroarylene group, $-Si(Q_4)(Q_5)-$, and $-N(Q_4)-$;

n3 and n4 are each independently selected from 1 and 2;

$Ar_1$ is selected from a hydrogen atom, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, and $-N(Q_6)(Q_7)$;

wherein, $Ar_1$ optionally binds to F, F', $L_1$, or $L_2$ to form a ring;

$Q_1$ to $Q_7$ are each independently selected from a hydrogen atom, a substituted or unsubstituted $C_1$-$C_{20}$ alkyl group, and a substituted or unsubstituted $C_6$-$C_{30}$ aryl group; and

* is a binding site to an adjacent atom.

According to an aspect of another embodiment, an organic light-emitting device includes:

a first electrode;

a second electrode; and an organic layer disposed between the first electrode and the second electrode, wherein the organic layer includes the amino fluorene polymer.

BRIEF DESCRIPTION OF THE DRAWING

These and/or other aspects will become apparent and more readily appreciated from the following description of the embodiments, taken in conjunction with the accompanying drawing in which:

FIG. 1 is a schematic cross-sectional view illustrating an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

As used herein, the expression of a numerical range with, such as "from x to y", refers to the range "from x or greater to y or less."

Unless defined otherwise, performing processes and measuring physical properties are considered as being done at a temperature of about 20 to 25° C. and a relative humidity of about 40% to about 50%.

To manufacture a large organic light-emitting device at lower costs, a liquid coating method may be used. A liquid coating method has a higher utilization efficiency of material compared to vacuum deposition methods. It is a convenient method of manufacturing a large organic light-emitting device, which does not need an expensive vacuum deposition apparatus.

Examples of used materials for a liquid coating method may include a small molecule material and a polymer material. The polymer material may have high coating uniformity and may have advantages of ease of forming multilayer.

For example, Patent documents 1 to 10 listed below disclose materials for organic light-emitting devices, wherein a part of small molecule material is replaced by vinyl groups, followed by polymerization to obtain polymerized materials for organic light-emitting devices.

Patent document 1: JP 1995-090255
Patent document 2: JP 1996-054833
Patent document 3: JP 1996-269133
Patent document 4: JP 2001-098023
Patent document 5: JP 2002-110359
Patent document 6: JP 2003-313240
Patent document 7: JP 2004-059743
Patent document 8: JP 2006-237592
Patent document 9: JP 2008-198989
Patent document 10: JP 2008-218983

However, an organic light-emitting device manufactured using such materials as disclosed in Patent documents 1 to 10 by a liquid coating method may have insufficient lifetime.

Hereinafter, embodiments of the present disclosure are described in greater details, but are not limited thereto.

Amino Fluorene Polymer

An amino fluorene polymer according to an embodiment may be a material with the ability to form a layer of an organic light-emitting device by liquid coating method. The amino fluorene polymer may have high solubility in solvents and may ensure high stability of layers after being coated. An organic light-emitting device including the amino fluorene polymer may have improved lifetime.

The amino fluorene polymer may be a polymer obtained by polymerization of polymerizable monomers. The amino fluorene polymer may include a first repeating unit represented by Formula 1.

Formula 1

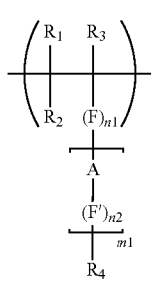

In Formula 1, $R_1$ to $R_3$ may be each independently selected from a hydrogen atom, a substituted or unsubstituted $C_1$-$C_{10}$ alkyl group, and a substituted or unsubstituted $C_6$-$C_{30}$ aryl group.

For example, in Formula 1, $R_1$ to $R_3$ may be each independently selected from a hydrogen atom, a methyl group, an ethyl group, an n-propyl group, and an n-butyl group. However, embodiments are not limited thereto.

In certain embodiments, in Formula 1, $R_1$ to $R_3$ may be each independently selected from a hydrogen atom and a methyl group. However, embodiments are not limited thereto.

In Formula 1, m1, which indicates the number of repeating of a moiety represented by *-A-(F')$_{n2}$—*', may be an integer from 1 to 20.

For example, in Formula 1, m1 may be an integer from 1 to 15. However, embodiments are not limited thereto.

In Formula 1, F and F' may be each independently selected from a substituted or unsubstituted azafluorenylene group and a substituted or unsubstituted fluorenylene group.

For example, in Formula 1, F and F' may be each independently a group represented by Formula 3. However, embodiments are not limited thereto.

Formula 3

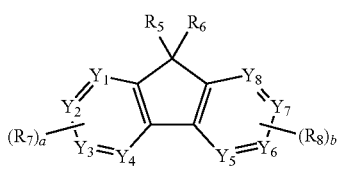

In Formula 3, $R_5$ to $R_8$ may be each independently selected from a binding site, a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$);

wherein, adjacent groups selected from $R_5$ to $R_8$ may be optionally linked to one another to form a ring;

wherein two groups selected from $R_5$ to $R_8$ may be binding sites to adjacent atoms (i.e., two groups selected from $R_5$ to $R_8$ may represent open valences);

$Q_1$ to $Q_3$ may be each independently selected from a hydrogen atom, a substituted or unsubstituted $C_1$-$C_{20}$ alkyl group, and a substituted or unsubstituted $C_6$-$C_{30}$ aryl group;

a and b may be each independently selected from 1, 2, 3, and 4; and $Y_1$ to $Y_8$ may be each independently a carbon atom or a nitrogen atom.

For example, in Formula 3, $R_5$ to $R_8$ may be each independently selected from a binding site, a hydrogen atom, a $C_1$-$C_{20}$ alkyl group, a $C_6$-$C_{30}$ aryl group, and a $C_5$-$C_{30}$ heteroaryl group, a $C_1$-$C_{20}$ alkyl group substituted with at least one selected from a halogen atom and a $C_6$-$C_{30}$ aryl group, and a $C_6$-$C_{30}$ aryl group and a $C_5$-$C_{30}$ heteroaryl group, each substituted with at least one selected from a $C_6$-$C_{30}$ aryl group, each substituted with at least one selected from $C_1$-$C_{20}$ alkyl group, a $C_6$-$C_{30}$ aryl group, and a $C_6$-$C_{30}$ aryl group;

wherein, adjacent groups selected from $R_5$ to $R_8$ may be optionally linked to one another to form a ring; and wherein two groups selected from $R_5$ to $R_8$ may be binding sites to adjacent atoms (i.e., two groups selected from $R_5$ to $R_8$ may represent open valences). However, embodiments are not limited thereto.

In certain embodiments, in Formula 3, $R_5$ to $R_8$ may be each independently selected from a binding site, a hydrogen atom, a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethylbutyl group, a 1-isopropyl propyl group, a 1,2-dimethyl butyl group, an n-heptyl group, a 1,4-dimethyl pentyl group, a 3-ethylpentyl group, a 2-methyl-1-isopropyl propyl group, a 1-ethyl-3-methyl butyl group, an n-octyl group, a 2-ethyl hexyl group, a 3-methyl-1-isopropyl butyl group, a 2-methyl-1-iso-propyl group, a 1-tert-butyl-2-methyl a propyl group, an n-nonyl group, a 3,5,5-trimethyl hexyl group, an n-decyl group, an iso-decyl group, an n-undecyl group, a 1-methyl decyl group, an n-dodecyl group, an n-tridecyl group, an n-tetradecyl group, an n-pentadecyl group, an n-hexadecyl group, an n-heptadecyl group, an n-octadecyl group, an n-nonadecyl group and an n-eicosyl group, a phenyl group, a naphthyl group, an anthracenyl group, a phenanthrenyl group, a pyridyl group, a pyrimidyl group, a pyrazinyl group, a triazinyl group, a furanyl group, and a thiophenyl group, a methyl group, an ethyl group, and an n-propyl group, each substituted with at least one selected from —F, a phenyl group, and a naphthyl group, and a phenyl group, a naphthyl group, an anthracenyl group, a phenanthrenyl group, a pyridyl group, a pyrimidyl group, a pyrazinyl group, a triazinyl group, a furanyl group, and a thiophenyl group, each substituted with at least one selected from a methyl group, an ethyl group, an n-propyl group, an iso-propyl group, an n-butyl group, an isobutyl group, a sec-butyl group, a tert-butyl group, an n-octyl group, a phenyl group, a naphthyl group, a phenyl group substituted with a methyl group, and a phenyl group substituted with a tert-butyl group;

wherein, adjacent groups selected from $R_5$ to $R_8$ may be optionally linked to one another to form a ring; and wherein two groups selected from $R_5$ to $R_8$ may be binding sites to adjacent atoms (i.e., two groups selected from $R_5$ to $R_8$ may represent open valences). However, embodiments are not limited thereto.

In certain embodiments, in Formula 3, $R_5$ to $R_8$ may be each independently selected from a binding site, a hydrogen atom, a methyl group, an ethyl group, an n-propyl group, an iso-propyl group, an n-butyl group, an isobutyl group, a sec-butyl group, a tert-butyl group, an n-octyl group, an n-octadecyl group, a phenyl group, a pyridinyl group, and a thiophenyl group, a methyl group and an ethyl group, each substituted with at least one selected from —F and a phenyl group, and a phenyl group substituted with at least one selected from a methyl group, a tert-butyl group, an n-octyl group, a phenyl group, and a phenyl group substituted with a tert-butyl group;

wherein, adjacent groups selected from $R_5$ to $R_8$ may be optionally linked to one another to form a ring; and wherein two groups selected from $R_5$ to $R_8$ may be binding sites to adjacent atoms (i.e., two groups selected from $R_5$ to $R_8$ may represent open valences). However, embodiments are not limited thereto.

In certain embodiments, in Formula 1, F and F' may be each independently selected from groups represented by Formulae 4-1 to 4-58. However, embodiments are not limited thereto.

4-1
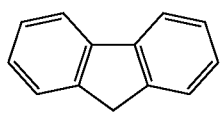

4-2
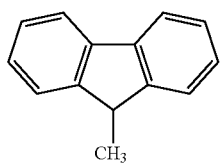

4-3
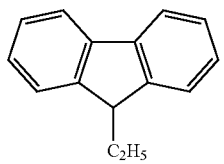

4-4
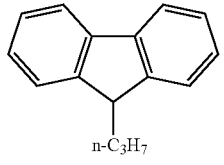

4-5
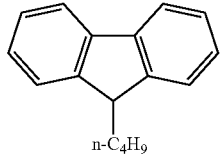

4-6
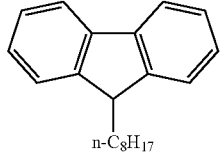

4-7
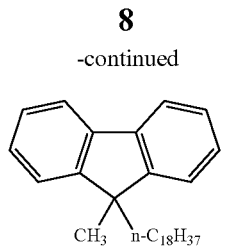

4-8
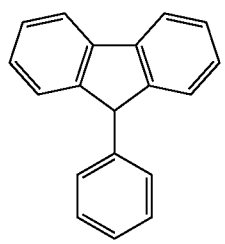

4-9
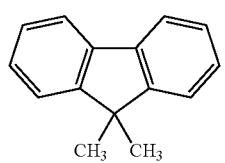

4-10
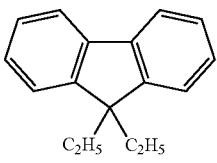

4-11
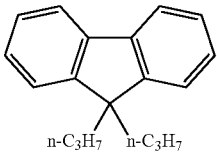

4-12
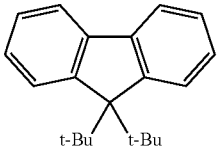

4-13
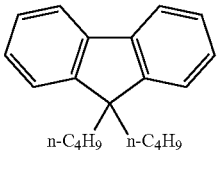

4-14
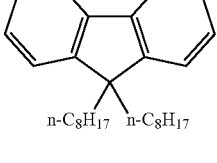

4-15
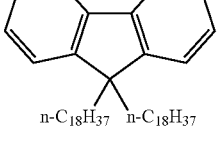

-continued
4-16
4-17
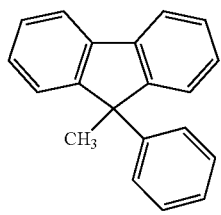
4-18
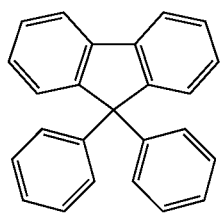
4-19
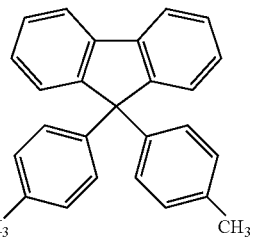
4-20
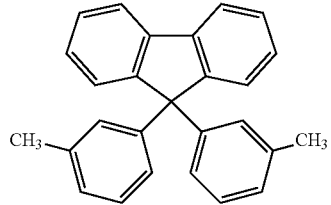
4-21
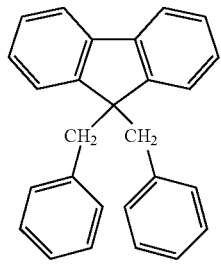
4-22
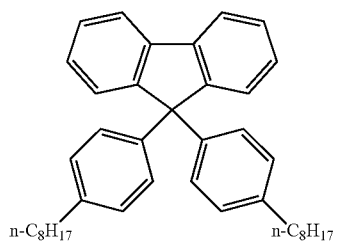
-continued
4-23
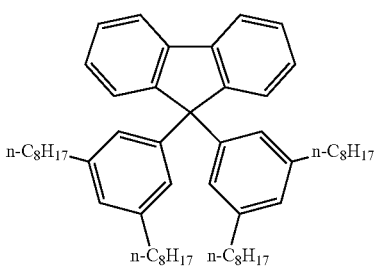
4-24
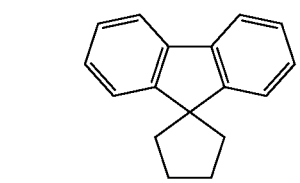
4-25
4-26
4-27
4-28
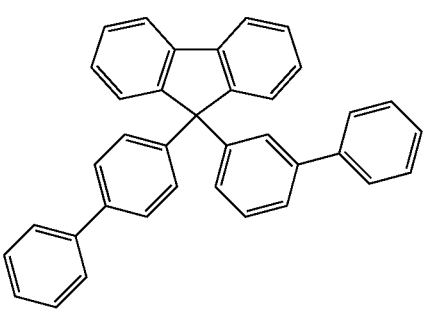

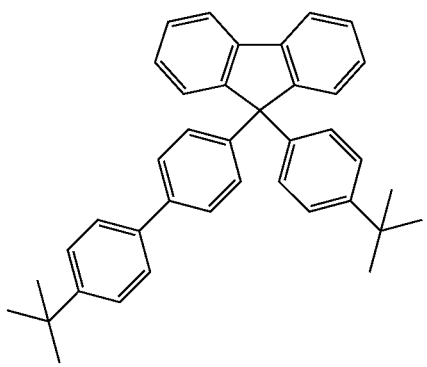
4-29
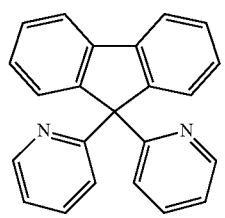
4-30
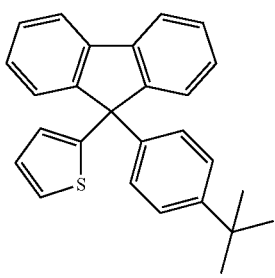
4-31
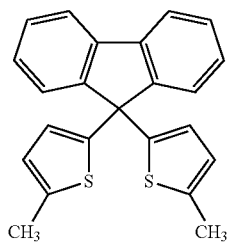
4-32
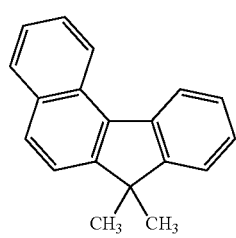
4-33
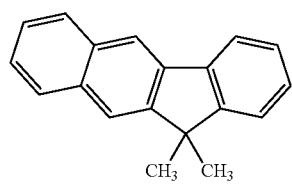
4-34
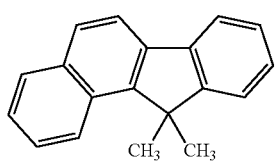
4-35
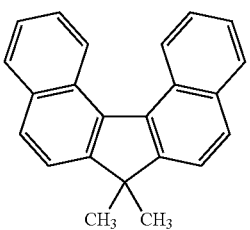
4-36
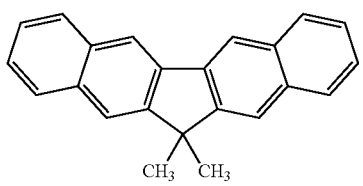
4-37
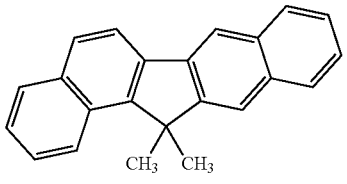
4-38
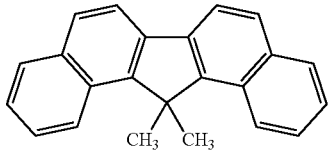
4-39
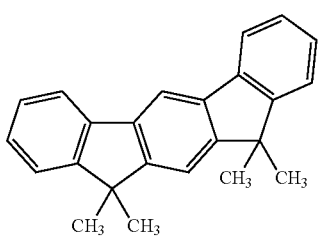
4-40
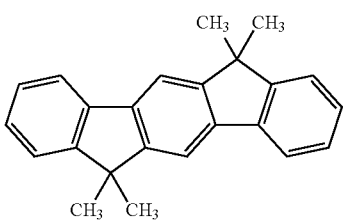
4-41

| 4-42 | 4-48 |
| 4-43 | 4-49 |
| 4-44 | 4-50 |
| 4-45 | 4-51 |
| 4-46 | 4-52 |
| 4-47 | 4-53 |
|      | 4-54 |

-continued

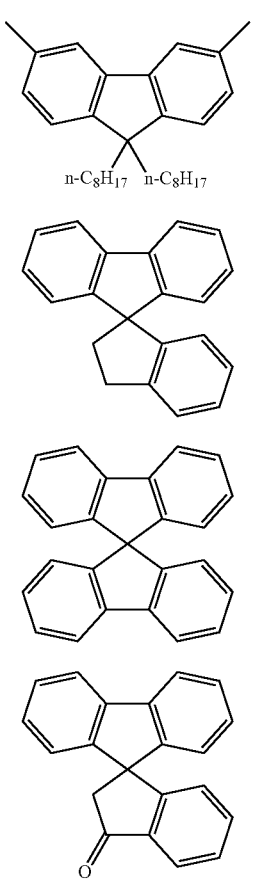

4-55

4-56

4-57

4-58

In Formulae 4-1 to 4-58, any two hydrogen atoms may be replaced by binding sites to adjacent atoms.

In Formula 1, n1 as the number of repeating of F, and n2 as the number of repeating of F' may be each independently selected from 1 and 2.

In Formula 1, A may be a group represented by Formula 2.

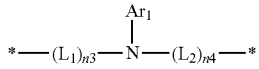

Formula 2

In Formula 2, $L_1$ and $L_2$ may be each independently selected from a single bond, a substituted or unsubstituted $C_1$-$C_{20}$ alkylene group, a substituted or unsubstituted $C_3$-$C_{16}$ cycloalkylene group, a substituted or unsubstituted $C_6$-$C_{30}$ arylene group, a substituted or unsubstituted $C_1$-$C_{20}$ oxyalkylene group, a substituted or unsubstituted $C_3$-$C_{16}$ oxycycloalkylene group, a substituted or unsubstituted $C_6$-$C_{30}$ oxyarylene group, a substituted or unsubstituted $C_7$-$C_{40}$ aralkylene group, a substituted or unsubstituted $C_5$-$C_{30}$ heteroarylene group, —Si($Q_4$)($Q_5$)-, and —N($Q_4$)-;

n3 and n4 may be each independently selected from 1 and 2;

$Ar_1$ may be selected from a hydrogen atom, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, and —N($Q_6$)($Q_7$);

wherein, $Ar_1$ may optionally bind to F, F', $L_1$, or $L_2$ to form a ring;

$Q_4$ to $Q_7$ may be each independently selected from a hydrogen atom, a substituted or unsubstituted $C_1$-$C_{20}$ alkyl group, and a substituted or unsubstituted $C_6$-$C_{30}$ aryl group; and

* may be a binding site to an adjacent atom.

For example, in Formula 2, $L_1$ and $L_2$ may be each independently selected from a single bond, a $C_1$-$C_{20}$ alkylene group, and a $C_6$-$C_{30}$ arylene group, and a $C_1$-$C_{20}$ alkylene group and a $C_6$-$C_{30}$ arylene group, each substituted with at least one selected from a $C_1$-$C_{20}$ alkyl group and a $C_6$-$C_{30}$ aryl group. However, embodiments are not limited thereto.

In certain embodiments, in Formula 2, $L_1$ and $L_2$ may be each independently selected from a single bond, a methylene group, and a phenylene group, and a methylene group and a phenylene group, each substituted with at least one selected from a methyl group, an n-hexyl group, and a phenyl group. However, embodiments are not limited thereto.

For example, in Formula 2, $Ar_1$ may be selected from a hydrogen atom, a $C_1$-$C_{20}$ alkyl group, and a $C_6$-$C_{30}$ aryl group, and a $C_6$-$C_{30}$ aryl group substituted with at least one selected from a $C_1$-$C_{20}$ alkyl group, a $C_6$-$C_{30}$ aryl group, and a $C_1$-$C_{20}$ alkoxy group; and wherein, $Ar_1$ may optionally bind to F, F', $L_1$, or $L_2$ to form a ring. However, embodiments are not limited thereto.

In certain embodiments, in Formula 2, $Ar_1$ may be selected from a hydrogen atom, a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methylbutyl group, an n-octyl group, a 2-ethyl hexyl group, a 3-methyl-1-isopropyl butyl group, a 2-methyl-1-iso-propyl group, a 1-tert-butyl-2-methyl-propyl group, a phenyl group, a naphthyl group, an anthracenyl group, and a phenanthrenyl group, and a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethylpentyl group, a 2-methyl-1-isopropyl propyl group, a 1-ethyl-3-methyl butyl group, an n-octyl group, a phenyl group, a naphthyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, and an n-octyloxy group; and wherein, $Ar_1$ may optionally bind to F, F', $L_1$, or $L_2$ to form a ring. However, embodiments are not limited thereto.

In certain embodiments, in Formula 2, $Ar_1$ may be selected from a hydrogen atom, a methyl group, an n-hexyl group, a phenyl group, a naphthyl group, and groups represented by Formulae 8-1 to 8-6; and wherein, $Ar_1$ may optionally bind to F, F', $L_1$, or $L_2$ to form a ring. However, embodiments are not limited thereto.

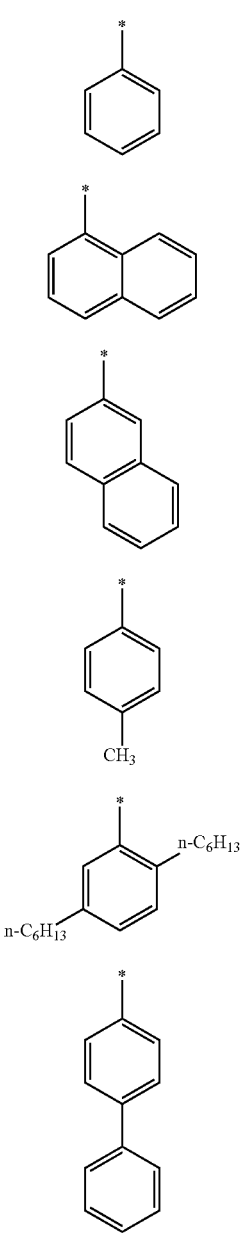

In Formulae 8-1 to 8-6, * may be a binding site to an adjacent atom.

In Formula 1, $R_4$ may be selected from a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$); and $Q_1$ to $Q_3$ may be each independently selected from a hydrogen atom, a substituted or unsubstituted $C_1$-$C_{20}$ alkyl group, and a substituted or unsubstituted $C_6$-$C_{30}$ aryl group.

For example, in Formula 1, $R_4$ may be selected from a hydrogen atom, a $C_1$-$C_{20}$ alkyl group, a $C_6$-$C_{30}$ aryl group, a $C_1$-$C_{20}$ alkoxy group, and —N($Q_1$)($Q_2$), and a $C_6$-$C_{30}$ aryl group substituted with at least one selected from a $C_1$-$C_{20}$ alkyl group, a $C_6$-$C_{30}$ aryl group, and a $C_1$-$C_{20}$ alkoxy group; and $Q_1$ and $Q_2$ may be each independently selected from a hydrogen atom and a $C_6$-$C_{30}$ aryl group; and a $C_6$-$C_{30}$ aryl group substituted with a $C_1$-$C_{20}$ alkyl group. However, embodiments are not limited thereto.

In certain embodiments, in Formula 1, $R_4$ may be selected from a hydrogen atom, a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethyl hexyl group, a 3-methyl-1-isopropyl butyl group, a 2-methyl-1-iso-propyl group, a 1-tert-butyl-2-methyl-propyl group, a phenyl group, a naphthyl group, an anthracenyl group, a phenanthrenyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, an n-octyloxy group, and —N($Q_1$)($Q_2$), and a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a phenyl group, a naphthyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, and an n-octyloxy group; and $Q_1$ and $Q_2$ may be each independently selected from a hydrogen atom, a phenyl group, a naphthyl group, an anthracenyl group, and a phenanthrenyl group, and a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, and a tert-butyl group. However, embodiments are not limited thereto.

In certain embodiments, in Formula 1, $R_4$ may be selected from a hydrogen atom, a methyl group, an n-hexyl group, a phenyl group, a naphthyl group, a methoxy group, and groups represented by Formulae 8-1 to 8-7. However, embodiments are not limited thereto.

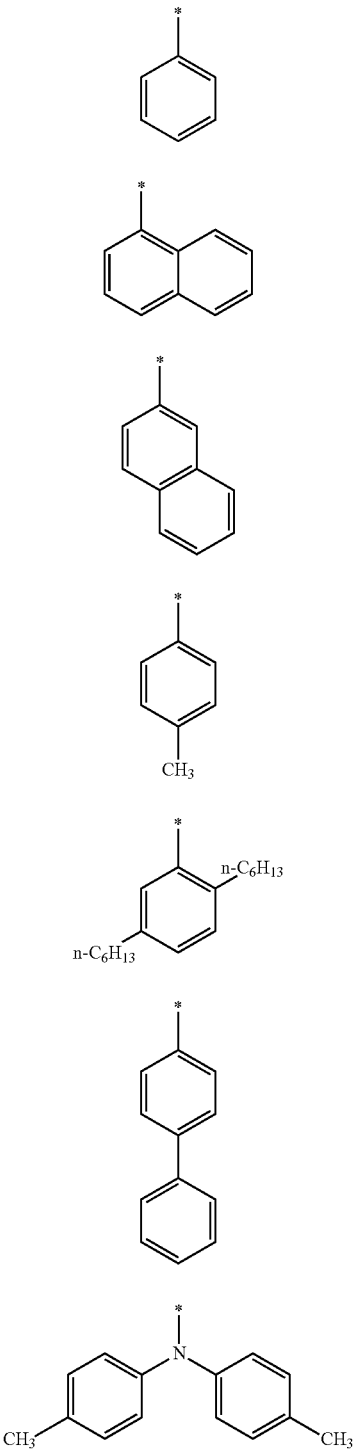

In Formulae 8-1 to 8-7, * may be a binding site to an adjacent atom.

For example, the first repeating unit of Formula 1 may be represented by Formula 1-1. However, embodiments are not limited thereto.

Formula 1-1'

In Formula 1-1, $R_1$ to $R_3$ may be each independently selected from a hydrogen atom, a substituted or unsubstituted $C_1$-$C_{10}$ alkyl group, and a substituted or unsubstituted $C_6$-$C_{30}$ aryl group;

m1 may be an integer from 1 to 20;

F and F' are each independently selected from a substituted or unsubstituted azafluorenylene group and a substituted or unsubstituted fluorenylene group;

n1 and n2 may be each independently selected from 1 and 2;

A may be a group represented by Formula 2; and $R_4$ may be selected from a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$).

Formula 2

$$*\!-\!(L_1)_{n3}\!-\!\underset{\underset{Ar_1}{|}}{N}\!-\!(L_2)_{n4}\!-\!*$$

In Formula 2, $L_1$ and $L_2$ may be each independently selected from a single bond, a substituted or unsubstituted $C_1$-$C_{20}$ alkylene group, a substituted or unsubstituted $C_3$-$C_{16}$ cycloalkylene group, a substituted or unsubstituted $C_6$-$C_{30}$ arylene group, a substituted or unsubstituted $C_1$-$C_{20}$ oxyalkylene group, a substituted or unsubstituted $C_3$-$C_{16}$ oxycycloalkylene group, a substituted or unsubstituted $C_6$-$C_{30}$ oxyarylene group, a substituted or unsubstituted $C_7$-$C_{40}$ aralkylene group, a substituted or unsubstituted $C_5$-$C_{30}$ heteroarylene group, —Si($Q_4$)($Q_5$)-, and —N($Q_4$)-;

n3 and n4 may be each independently selected from 1 and 2;

Ar₁ may be selected from a hydrogen atom, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, and —N(Q₆)(Q₇);

wherein, Ar₁ may optionally bind to F, F', L₁, or L₂ to form a ring;

* may be a binding site to an adjacent atom;

R₅ to R₈ may be each independently selected from a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si(Q₁)(Q₂)(Q₃), and —N(Q₁)(Q₂);

wherein, adjacent groups selected from R₅ to R₈ may be optionally linked to one another to form a ring;

a and b may be each independently selected from 1, 2, 3, and 4;

Y₁ to Y₈ may be each independently a carbon atom or a nitrogen atom; and

Q₁ to Q₇ may be each independently selected from a hydrogen atom, a substituted or unsubstituted $C_1$-$C_{20}$ alkyl group, and a substituted or unsubstituted $C_6$-$C_{30}$ aryl group.

For example, the first repeating unit of Formula 1 may be selected from units represented by the following formulae. However, embodiments are not limited thereto.

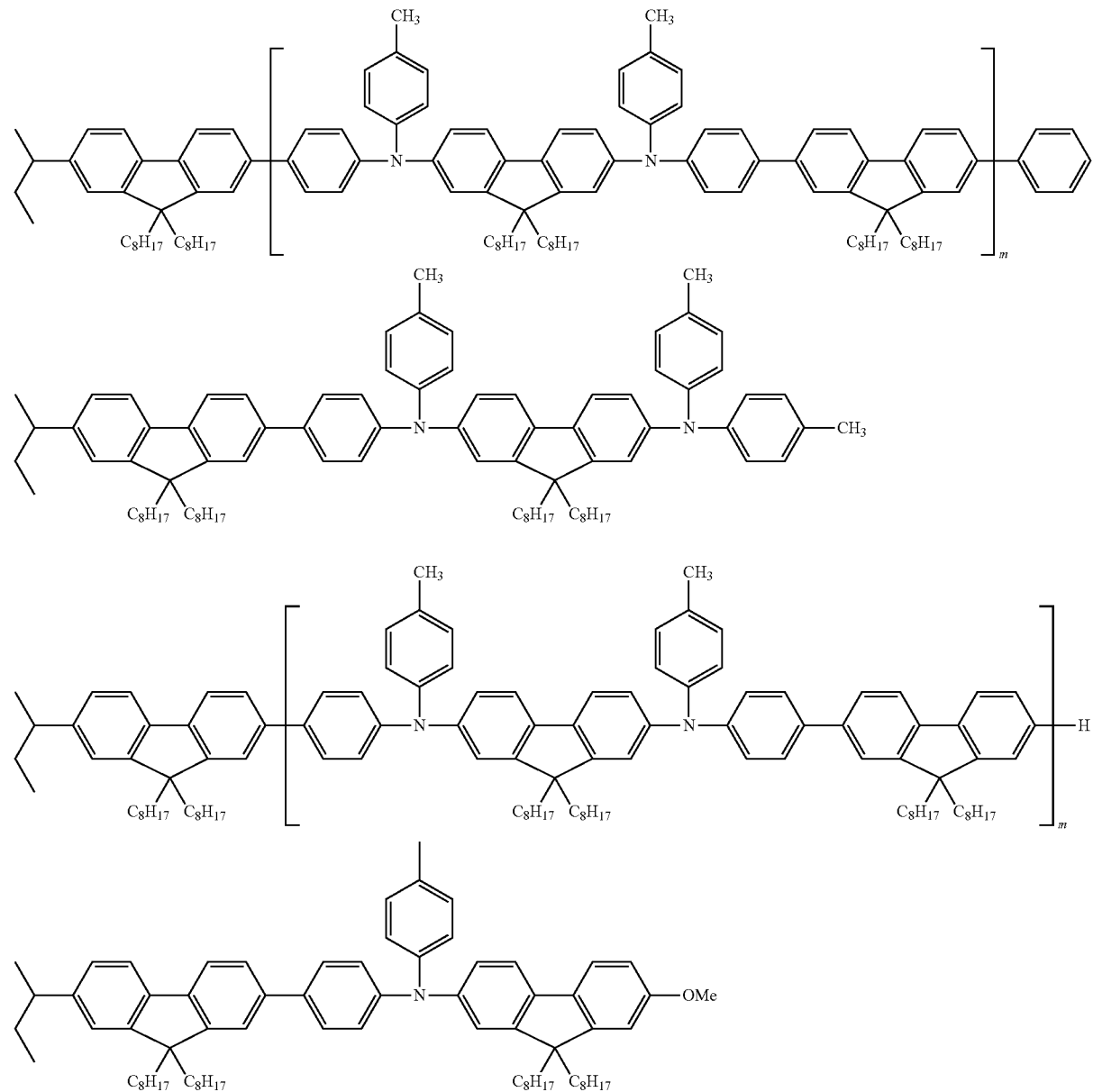

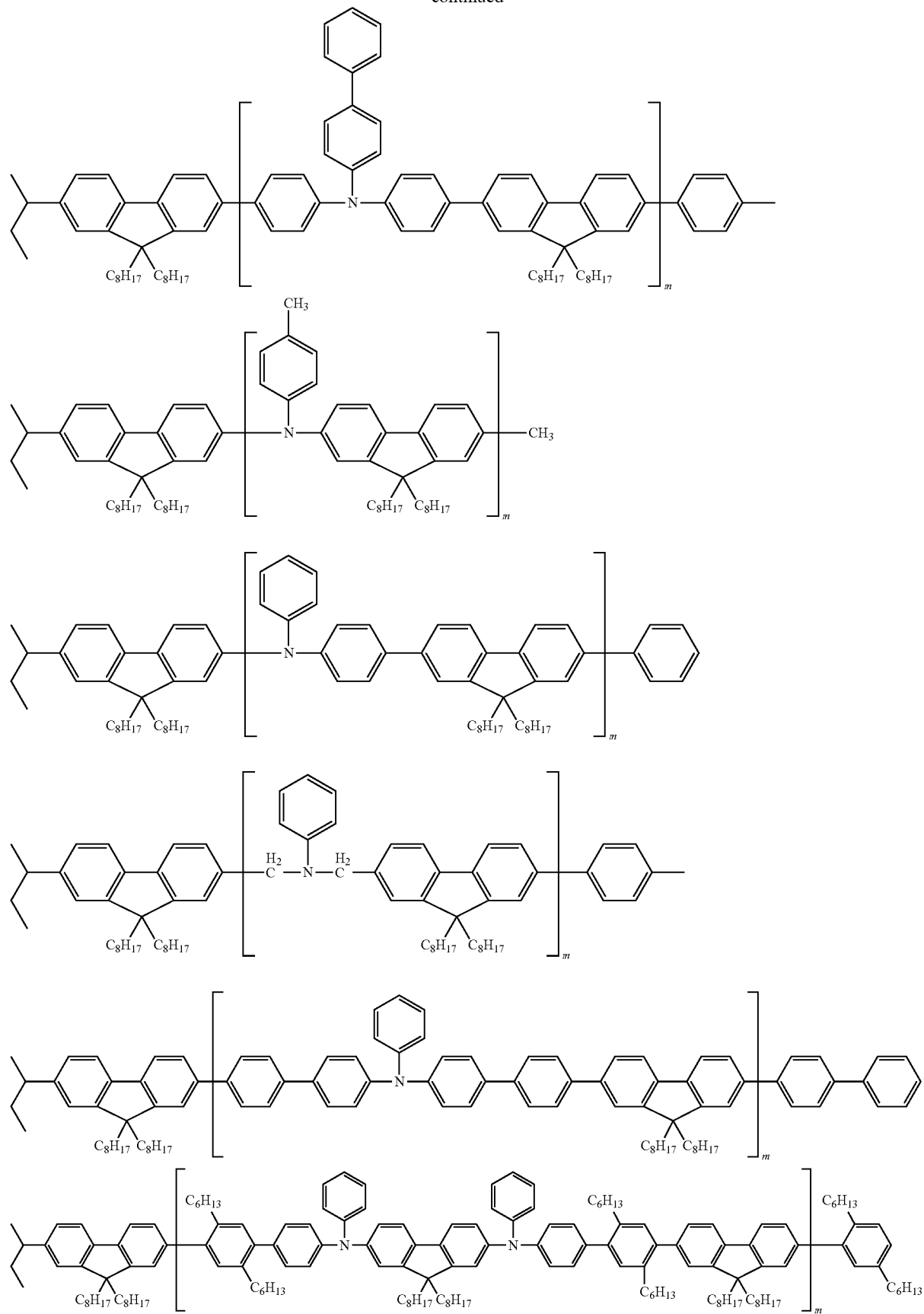

-continued
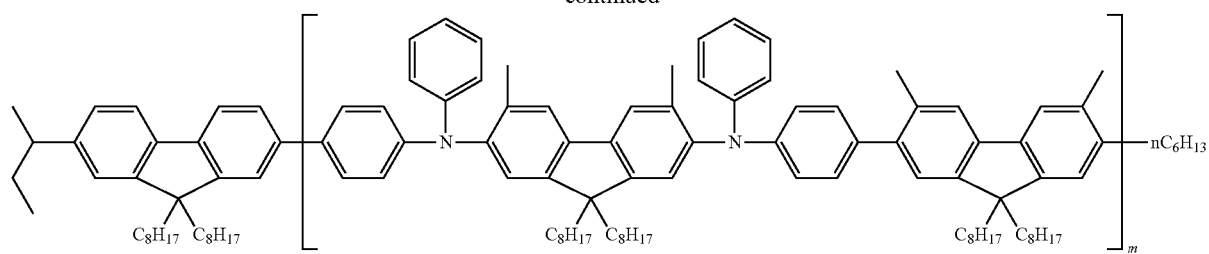
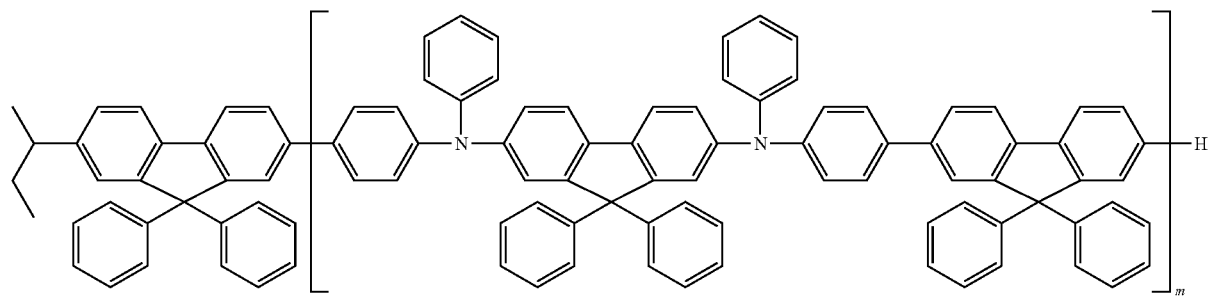
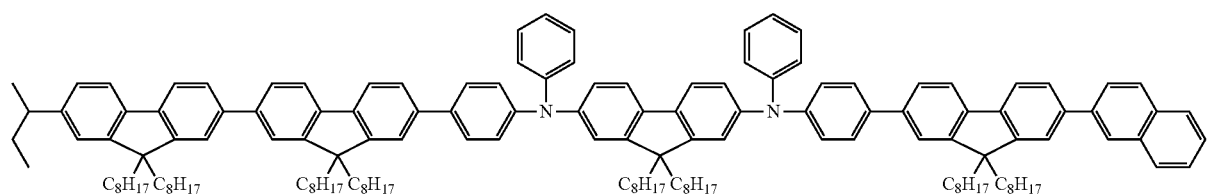
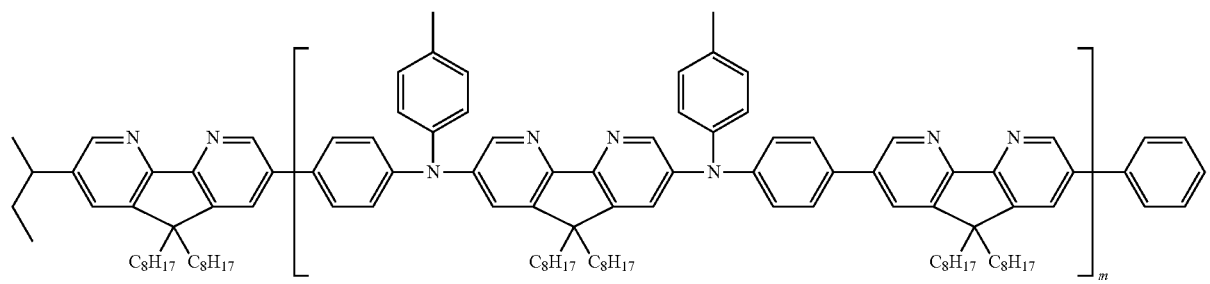
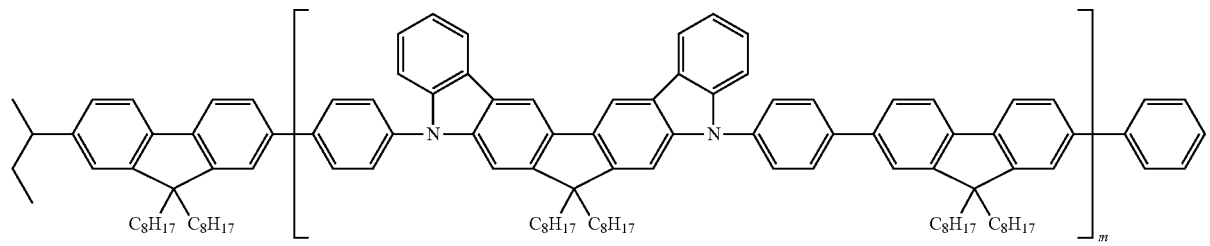
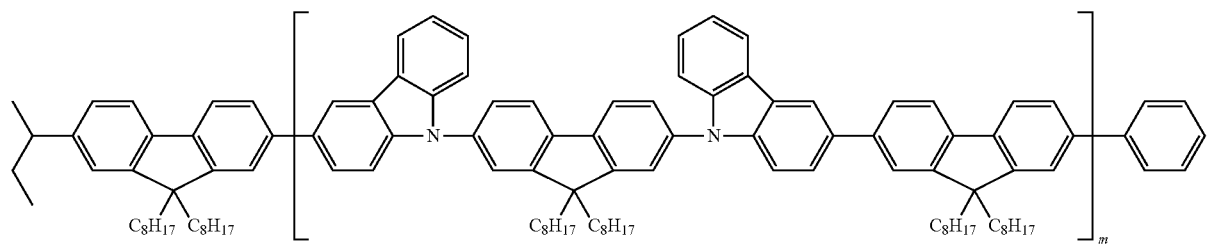

-continued
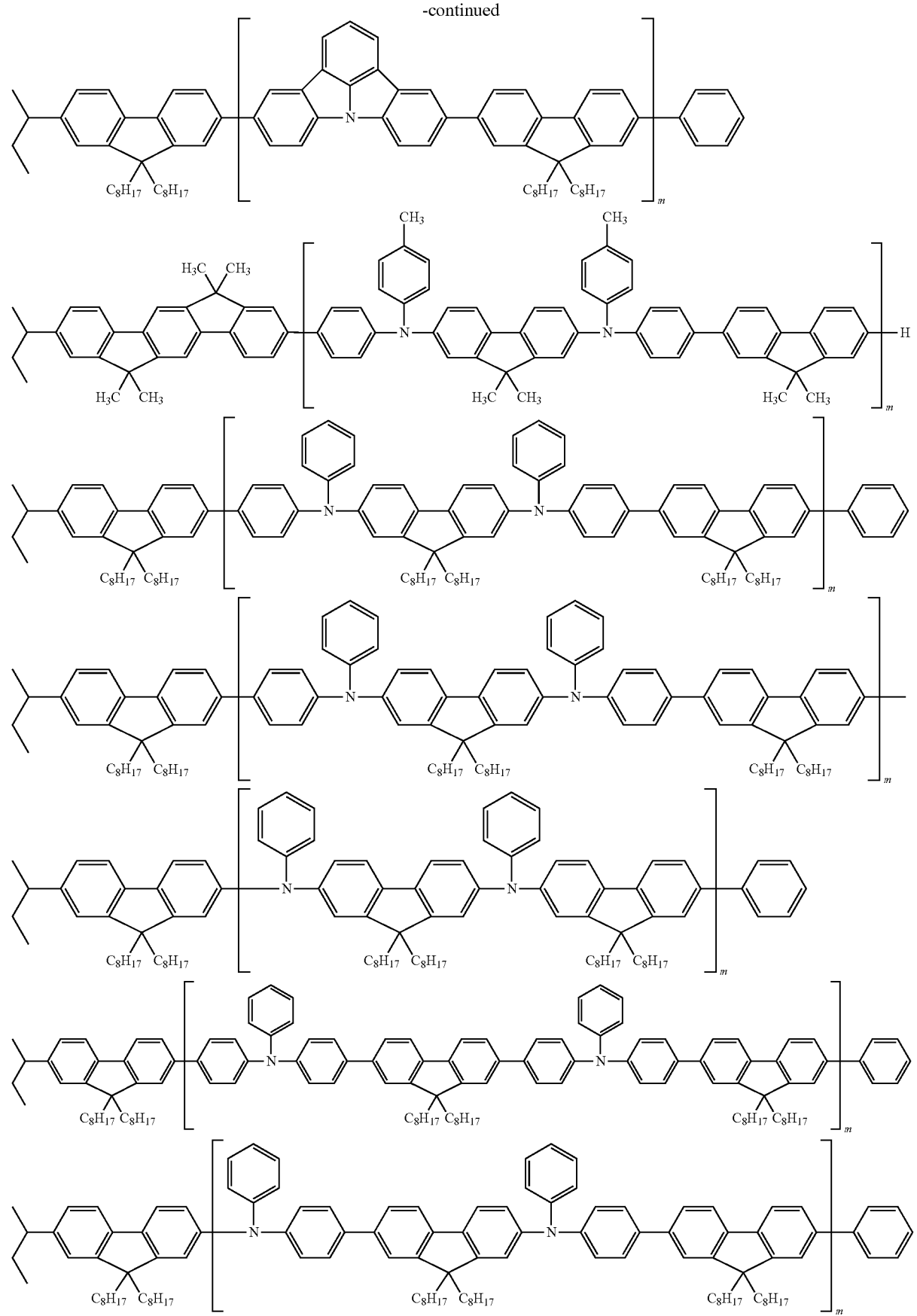

-continued

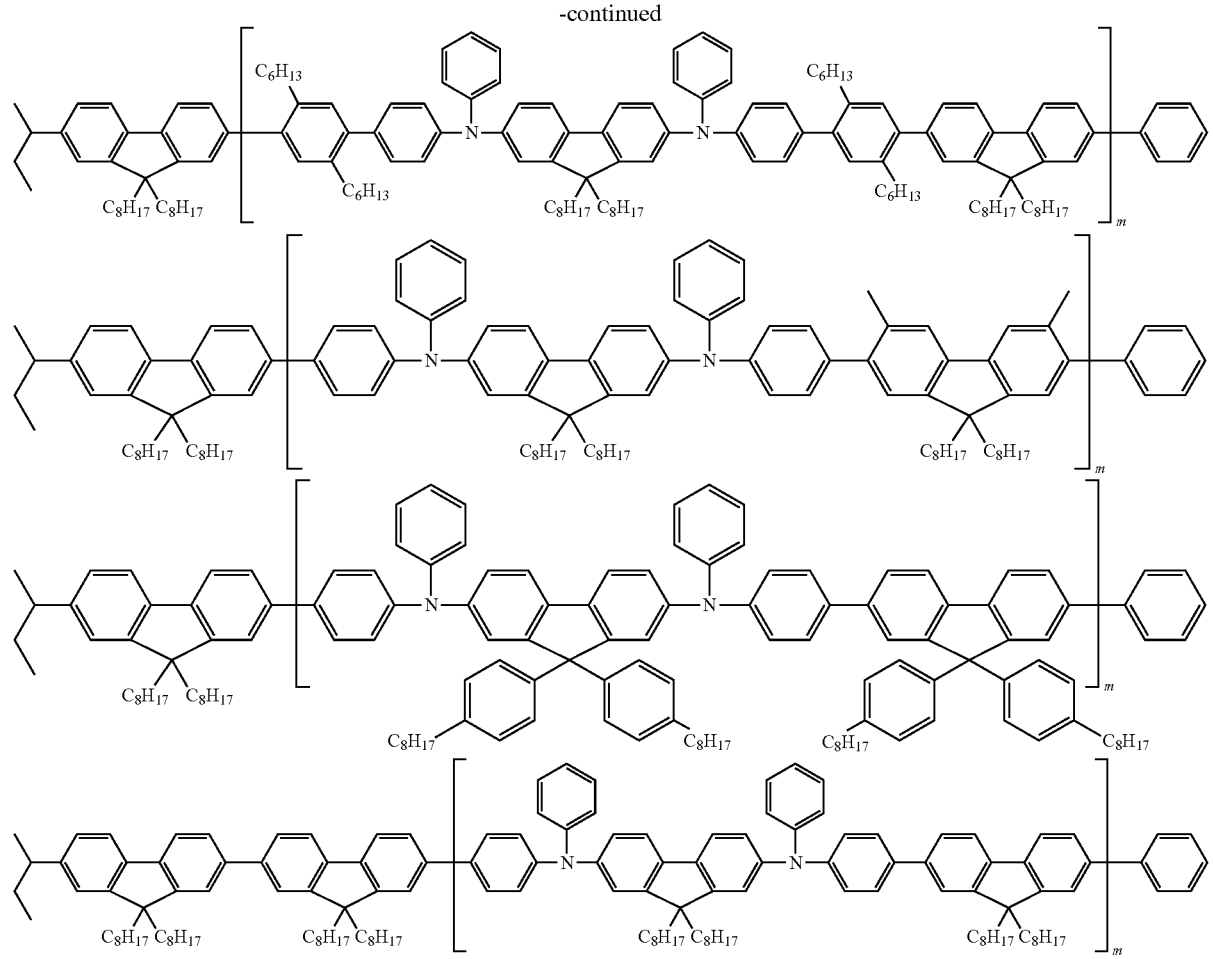

In the above formulae, m may be an integer from 1 to 10.

An amino fluorene polymer according to any embodiment includes a fluorene structure directly bound to a side chain of the polymer, wherein the fluorene structure further includes: i) a substituent with an amine structure and ii) a substituent with a fluorene structure. The amino fluorene polymer may include consecutive substituents with amine structure and consecutive substituents with fluorene structure. Alternatively, the substituents with amine structure may alternate with the substituents with fluorene structure.

An organic light-emitting device including an amino fluorene polymer according to any of the embodiments may have improved emission lifetime and improved current efficiency.

The amino fluorene polymer including a first repeating unit represented by Formula 1 may include a fluorenylene group at a polymerization site, and thus may have about 3 times or greater higher carbon-carbon bond dissociation energy, compared to polymers including a phenylene group at a polymerization site. Accordingly, an organic light-emitting device including the amino fluorene polymer may have improved lifetime.

The amino fluorene polymer may have a number average molecular weight (Mn) of, for example, about 10,000 Daltons (Da) or greater to about 100,000 Da or less. However, embodiments are not limited thereto. While not wishing to be bound by theory, it is understood that when the amino fluorene polymer has a number average molecular weight within this range, a coating composition for forming a layer including the amino fluorene polymer (for example, a hole injection layer and/or a hole transport layer) may have an appropriate viscosity, and thus the resulting layer may have a uniform thickness.

The amino fluorene polymer may have a weight average molecular weight (Mw) of, for example, about 10,000 Da or greater to about 300,000 Da or less. However, embodiments are not limited thereto. While not wishing to be bound by theory, it is understood that when the amino fluorene polymer has a weight average molecular weight within this range, a coating composition for forming a layer including the amino fluorene polymer (for example, a hole injection layer and/or a hole transport layer) may have an appropriate viscosity, and thus the resulting layer may have a uniform thickness.

The amino fluorene polymer may have a polydispersity index (as a ratio of weight average molecular weight to number average molecular weight (Mn/Mw)) of, for example, about 1.5 or greater and 2.5 or less. However, embodiments are not limited thereto. While not wishing to be bound by theory, it is understood that when the amino fluorene polymer has a polydispersity index within this range, a coating composition for forming a layer including the amino fluorene polymer (for example, a hole injection layer and/or a hole transport layer) may have an appropriate viscosity, and thus the resulting layer may have a uniform thickness.

Methods of measuring or calculating the number average molecular weight (Mn), weight average molecular weight (Mw), and polydispersity index are not particularly limited, and may be any known methods. As used herein, a number average molecular weight (Mn), a weight average molecular weight (Mw), and a polydispersity index are values measured by the methods described in examples that will be described later.

The amino fluorene polymer may further include a second repeating unit derived from a monomer including at least one cross-linking group. That is, the amino fluorene polymer may be a copolymer including a first repeating unit as described above and a second repeating unit.

The cross-linking group may be selected from cross-linking groups represented by Formulae 5-1 to 5-10. However, embodiments are not limited thereto.

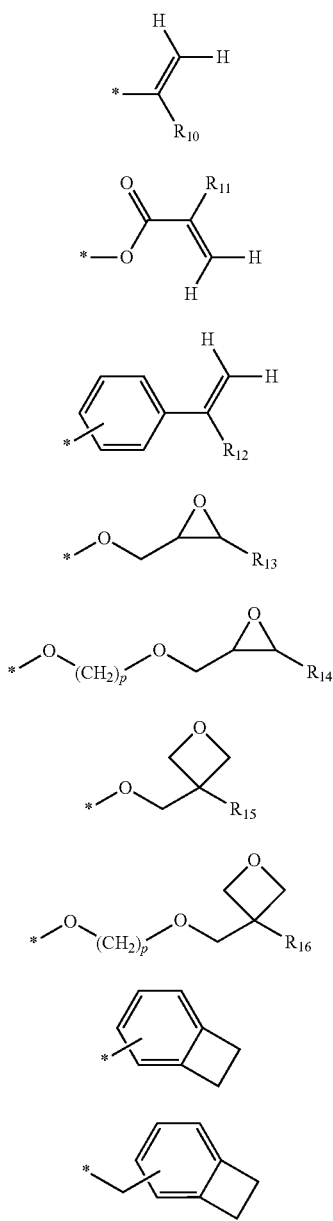

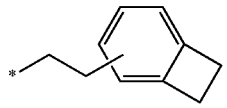

In Formulae 5-1 to 5-10,
$R_{10}$ to $R_{16}$ may be each independently a hydrogen atom, or a substituted or unsubstituted $C_1$-$C_{20}$ alkyl group;
p may be an integer from 1 to 10; and
* may be a binding site to an adjacent atom.

In certain embodiments, the second repeating unit may be represented by Formula 6. However, embodiments are not limited thereto.

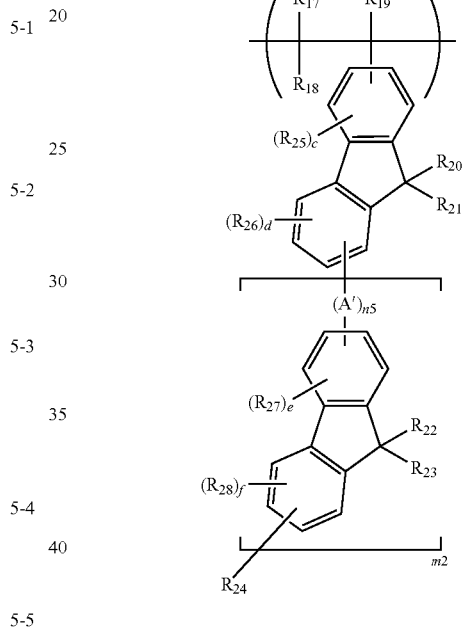

In Formula 6,
$R_{17}$ to $R_{19}$ may be each independently a hydrogen atom, a substituted or unsubstituted $C_1$-$C_{10}$ alkyl group, or a substituted or unsubstituted $C_6$-$C_{30}$ aryl group;
$R_{20}$ to $R_{28}$ may be each independently selected from cross-linking groups represented by Formulae 5-1 to 5-10, a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$);
wherein, adjacent groups of $R_{20}$ to $R_{28}$ may be optionally linked to one another to form a ring;
at least one group of $R_{20}$ to $R_{28}$ may be selected from cross-linking groups represented by Formulae 5-1 to 5-10;
c, d, e, and f may be each independently selected from 1, 2, and 3;
A' may be selected from a single bond, a substituted or unsubstituted $C_1$-$C_{20}$ alkylene group, a substituted or unsubstituted $C_3$-$C_{16}$ cycloalkylene group, a substituted or unsubstituted $C_6$-$C_{30}$ arylene group, a substituted or unsubstituted $C_1$-$C_{20}$ oxyalkylene group, a substituted or unsubstituted $C_3$-$C_{16}$ oxycycloalkylene group, a substituted or unsubstituted $C_6$-$C_{30}$ oxyarylene group, a substituted or unsubstituted $C_7$-$C_{40}$ aralkylene group, a substituted or unsubstituted $C_5$-$C_{30}$ heteroarylene group, —Si($Q_4$)($Q_5$)-, and —N($Q_4$)-;

n5 may be selected from 1, 2, 3, 4, and 5;

m2 may be an integer from 0 to 20;

$Q_1$ to $Q_5$ may be each independently selected from a hydrogen atom, a substituted or unsubstituted $C_1$-$C_{20}$ alkyl group, and a substituted or unsubstituted $C_6$-$C_{30}$ aryl group;

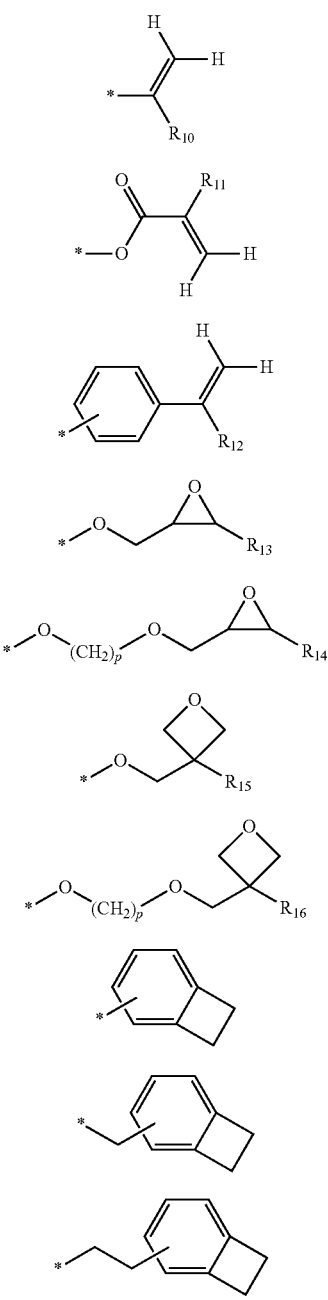

In Formulae 5-1 to 5-10, $R_{10}$ to $R_{16}$ may be each independently a hydrogen atom, or a substituted or unsubstituted $C_1$-$C_{20}$ alkyl group;

p may be an integer from 1 to 10; and

* may be a binding site to an adjacent atom.

For example, in Formula 6, $R_{17}$ to $R_{19}$ may be each independently selected from a hydrogen atom, a methyl group, an ethyl group, an n-propyl group, and an n-butyl group. However, embodiments are not limited thereto.

In certain embodiments, in Formula 6, $R_{17}$ to $R_{19}$ may be each independently selected from a hydrogen atom and a methyl group. However, embodiments are not limited thereto.

For example, in Formula 6, $R_{20}$ to $R_{28}$ may be each independently selected from the cross-linking groups represented by Formulae 5-1 to 5-10, a hydrogen atom, a $C_1$-$C_{20}$ alkyl group, a $C_6$-$C_{30}$ aryl group, a $C_1$-$C_{20}$ alkoxy group, and —N($Q_1$)($Q_2$), and a $C_6$-$C_{30}$ aryl group substituted with at least one selected from a $C_1$-$C_{20}$ alkyl group, a $C_6$-$C_{30}$ aryl group, and a $C_1$-$C_{20}$ alkoxy group;

wherein, adjacent groups of $R_{20}$ to $R_{28}$ may be optionally linked to one another to form a ring;

at least one group of $R_{20}$ to $R_{28}$ may be selected from the cross-linking groups represented by Formulae 5-1 to 5-10; and $Q_1$ and $Q_2$ may be each independently selected from a hydrogen atom and a $C_6$-$C_{30}$ aryl group; and a $C_6$-$C_{30}$ aryl group substituted with $C_1$-$C_{20}$ alkyl group. However, embodiments are not limited thereto.

In certain embodiments, in Formula 6, $R_{20}$ to $R_{28}$ may be each independently selected from the cross-linking groups represented by Formulae 5-1 to 5-10, a hydrogen atom, a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethylpropyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethyl hexyl group, a 3-methyl-1-isopropyl butyl group, a 2-methyl-1-iso-propyl group and 1-tert-butyl-2-methyl-propyl group, a phenyl group, a naphthyl group, an anthracenyl group, a phenanthrenyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, an n-octyloxy group, and —N($Q_1$)($Q_2$), and a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a phenyl group, a naphthyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, and an n-octyloxy group, wherein, adjacent groups of $R_{20}$ to $R_{28}$ may be optionally linked to one another to form a ring;

at least one group of $R_{20}$ to $R_{28}$ may be selected from the cross-linking groups represented by Formulae 5-1 to 5-10; and $Q_1$ and $Q_2$ may be each independently selected from a hydrogen atom, a phenyl group, a naphthyl group, an anthracenyl group, and a phenanthrenyl group, and a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, and a tert-butyl group. However, embodiments are not limited thereto.

In certain embodiments, in Formula 6, $R_{20}$ to $R_{28}$ may be each independently selected from the cross-linking groups represented by Formulae 5-1 to 5-10, a hydrogen atom, a methyl group, an n-hexyl group, a phenyl group, a naphthyl group, a methoxy group, and groups represented by Formulae 8-1 to 8-7;

wherein, adjacent groups of $R_{20}$ to $R_{28}$ may be optionally linked to one another to form a ring; and at least one group of $R_{20}$ to $R_{28}$ may be selected from the cross-linking groups represented by Formulae 5-1 to 5-10. However, embodiments are not limited thereto.

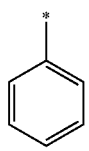

8-1

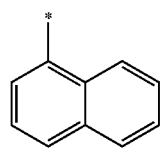

8-2

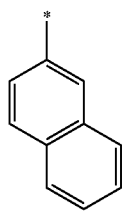

8-3

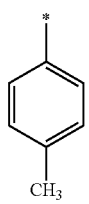

8-4

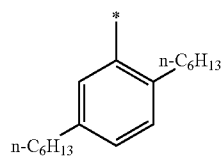

8-5

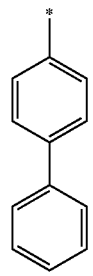

8-6

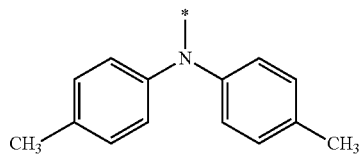

8-7

In Formulae 8-1 to 8-7, * may be a binding site to an adjacent atom.

For example, in Formula 6, A' may be selected from a single bond, a $C_1$-$C_{20}$ alkylene group, a $C_6$-$C_{30}$ arylene group, and —N($Q_4$), and a $C_1$-$C_{20}$ alkylene group and a $C_6$-$C_{30}$ arylene group, each substituted with at least one selected from a $C_1$-$C_{20}$ alkyl group and a $C_6$-$C_{30}$ aryl group; and $Q_4$ may be selected from a hydrogen atom, a $C_1$-$C_{20}$ alkyl group, and a $C_6$-$C_{30}$ aryl group, and a $C_6$-$C_{30}$ aryl group substituted with at least one selected from a $C_1$-$C_{20}$ alkyl group, a $C_6$-$C_{30}$ aryl group, and a $C_1$-$C_{20}$ alkoxy group. However, embodiments are not limited thereto.

In certain embodiments, in Formula 6, A' may be selected from a single bond, a methylene group, a phenylene group, and —N($Q_4$), and a methylene group and a phenylene group, each substituted with at least one selected from a methyl group, an n-hexyl group, and a phenyl group; and $Q_4$ may be selected from a hydrogen atom, a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethylbutyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethyl hexyl group, a 3-methyl-1-isopropylbutyl group, a 2-methyl-1-iso-propyl group, a 1-tert-butyl-2-methyl-propyl group, a phenyl group, a naphthyl group, an anthracenyl group, and a phenanthrenyl group, and a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethylpentyl group, a 3-ethyl pentyl group, a 2-methyl-1-isopropyl propyl group, a 1-ethyl-3-methyl butyl group, an n-octyl group, a phenyl group, a naphthyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, and an n-octyloxy group. However, embodiments are not limited thereto.

In certain embodiments, in Formula 6, A' may be selected from a single bond, a methylene group, a phenylene group, and $-N(Q_4)$, and a methylene group and a phenylene group, each substituted with at least one selected from a methyl group, an n-hexyl group, and a phenyl group; and $Q_4$ may be selected from a hydrogen atom, a methyl group, an n-hexyl group, a phenyl group, a naphthyl group, and groups represented by Formulae 8-1 to 8-6. However, embodiments are not limited thereto.

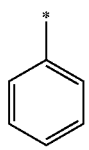

8-1

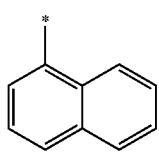

8-2

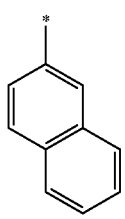

8-3

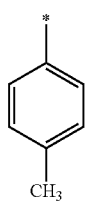

8-4

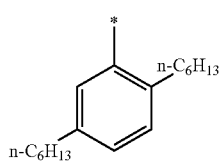

8-5

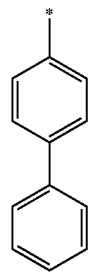

8-6

In Formulae 8-1 to 8-6, * may be a binding site to an adjacent atom.

For example, in Formula 6, $(A')_{n5}$ may be selected from a single bond, a $C_1$-$C_{20}$ alkylene group, a $C_6$-$C_{30}$ arylene group, and a group represented by Formula 2, and a $C_1$-$C_{20}$ alkylene group and a $C_6$-$C_{30}$ arylene group, each substituted with at least one selected from a $C_1$-$C_{20}$ alkyl group and a $C_6$-$C_{30}$ aryl group. However, embodiments are not limited thereto.

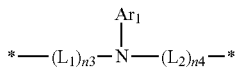

Formula 2

In Formula 2, $L_1$ and $L_2$ may be each independently selected from a single bond, a $C_1$-$C_{20}$ alkylene group, and a $C_6$-$C_{30}$ arylene group, and a $C_1$-$C_{20}$ alkylene group and a $C_6$-$C_{30}$ arylene group, each substituted with at least one selected from a $C_1$-$C_{20}$ alkyl group and a $C_6$-$C_{30}$ aryl group;

n3 and n4 may be each independently selected from 1 and 2;

$Ar_1$ may be selected from a hydrogen atom, a $C_1$-$C_{20}$ alkyl group, and a $C_6$-$C_{30}$ aryl group, and a $C_6$-$C_{30}$ aryl group substituted with at least one selected from a $C_1$-$C_{20}$ alkyl group, a $C_6$-$C_{30}$ aryl group, and a $C_1$-$C_{20}$ alkoxy group; and

* may be a binding site to an adjacent atom.

For example, in Formula 6, at least one group of $R_{20}$ to $R_{28}$ may be selected from cross-linking groups represented by Formulae 5-8 to 5-10. However, embodiments are not limited thereto.

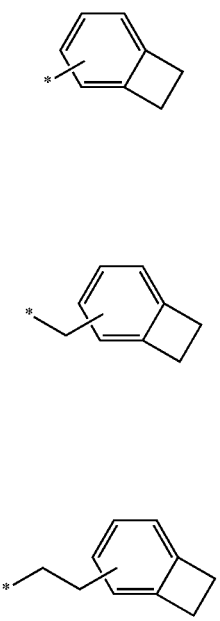

5-8

5-9

5-10

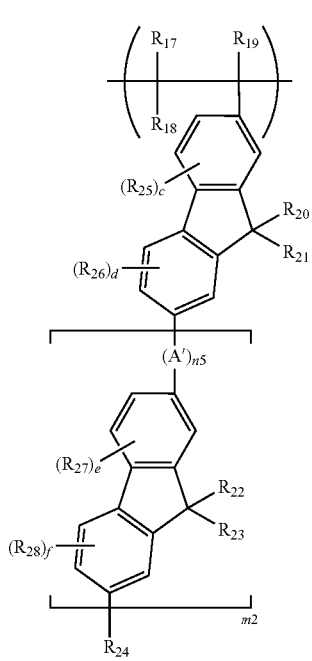

Formula 6-1

In Formulae 5-8 to 5-10, * may be a binding site to an adjacent group.

For example, the second repeating unit of Formula 6 may be represented by Formula 6-1. However, embodiments are not limited thereto.

In Formula 6-1, $R_{17}$ to $R_{28}$, c, d, e, f, A', n5, and m2 may be defined the same as those in Formula 6.

In certain embodiments, the second repeating unit may be selected from units represented by the following formulae. However, embodiments are not limited thereto.

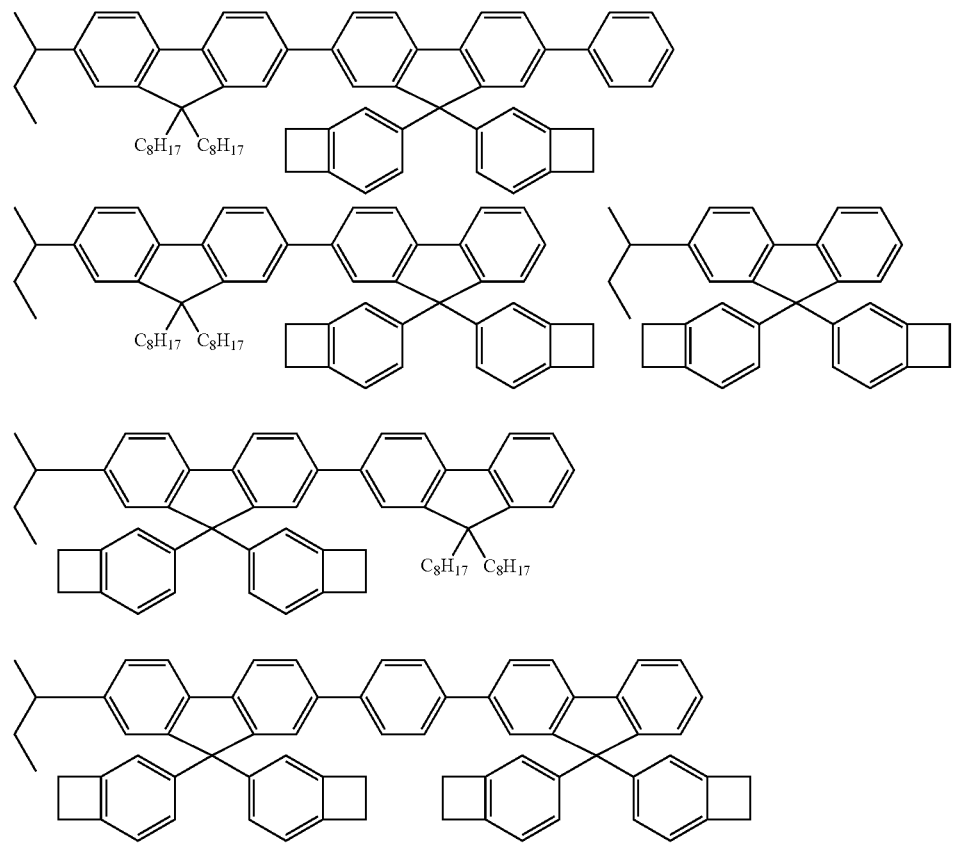

-continued
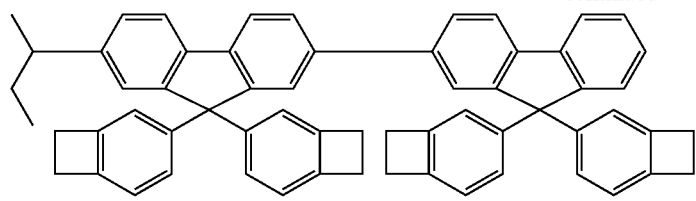
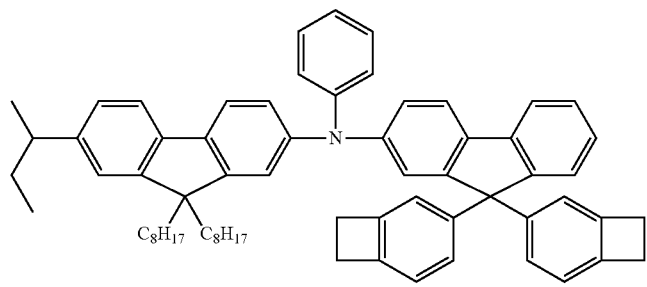
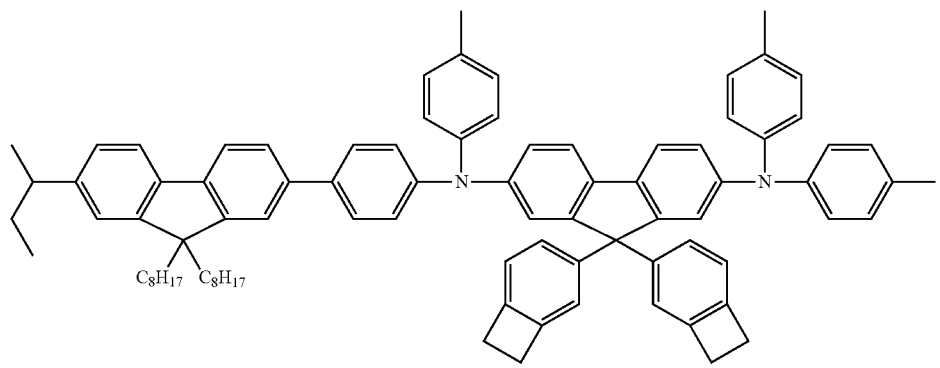
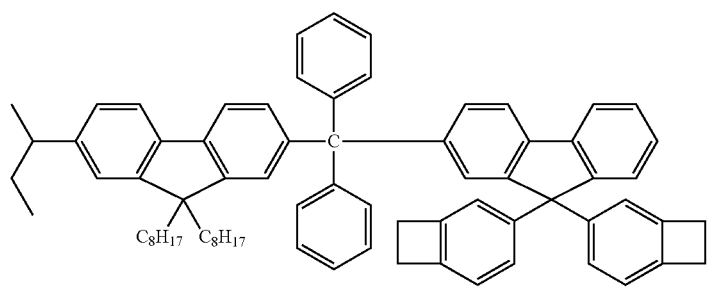
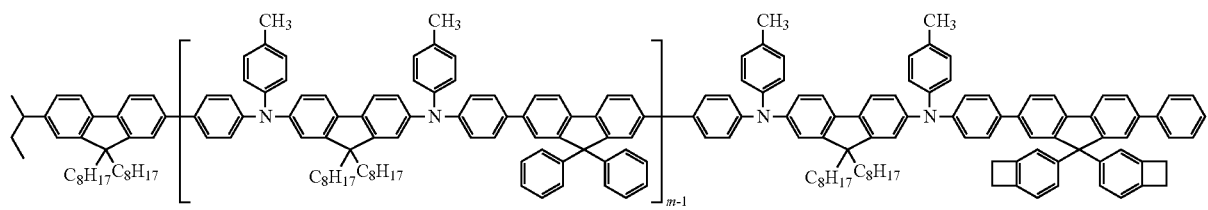
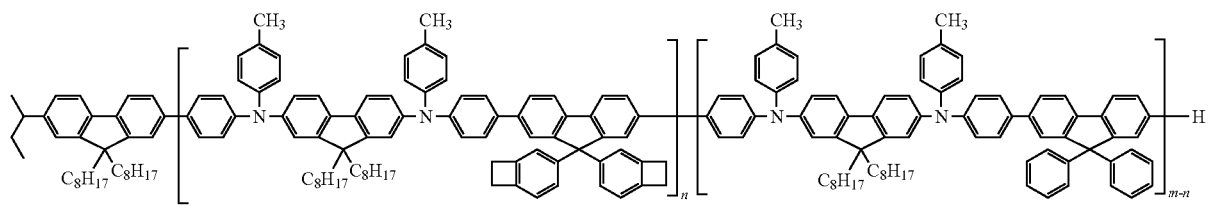

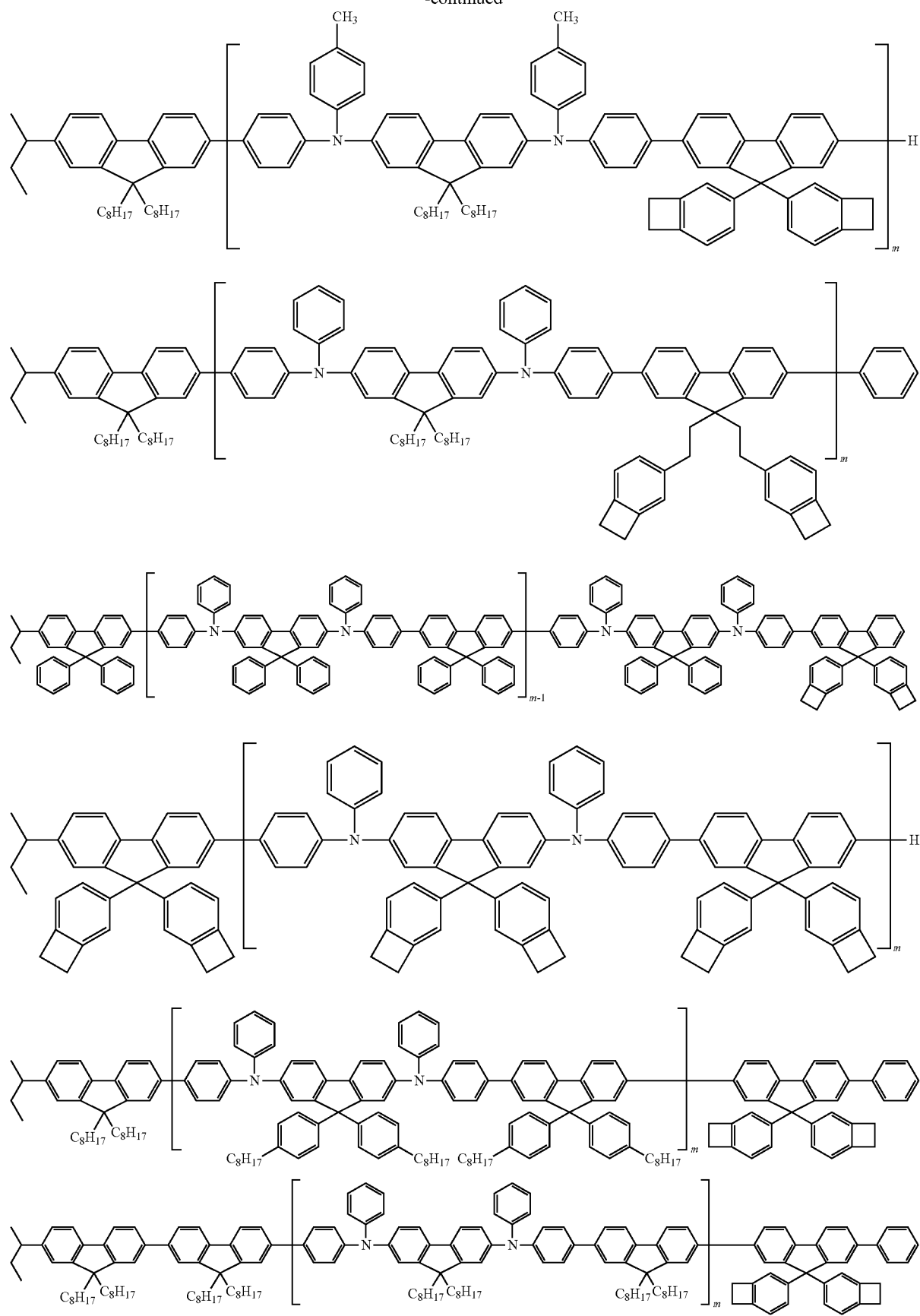

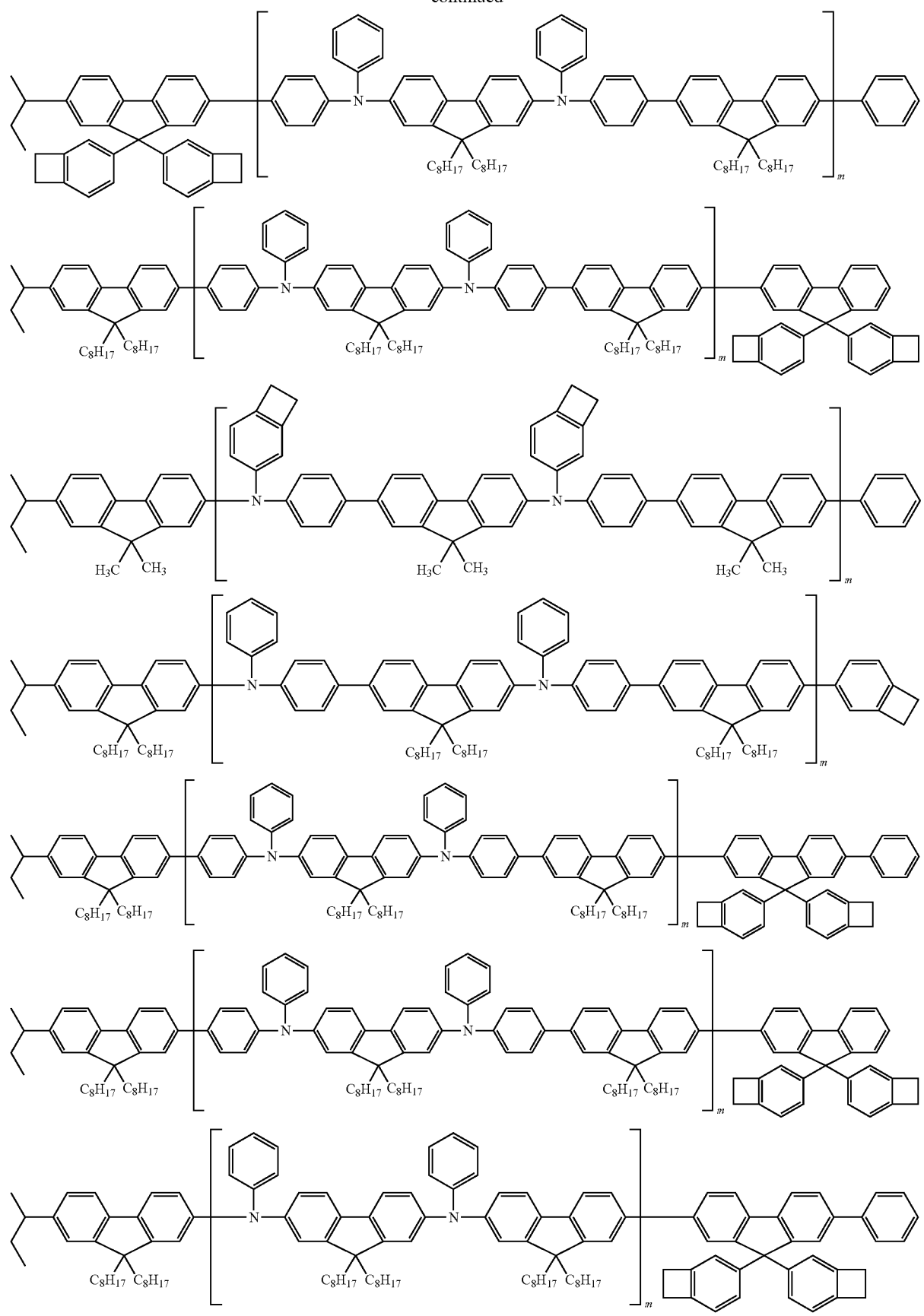

-continued
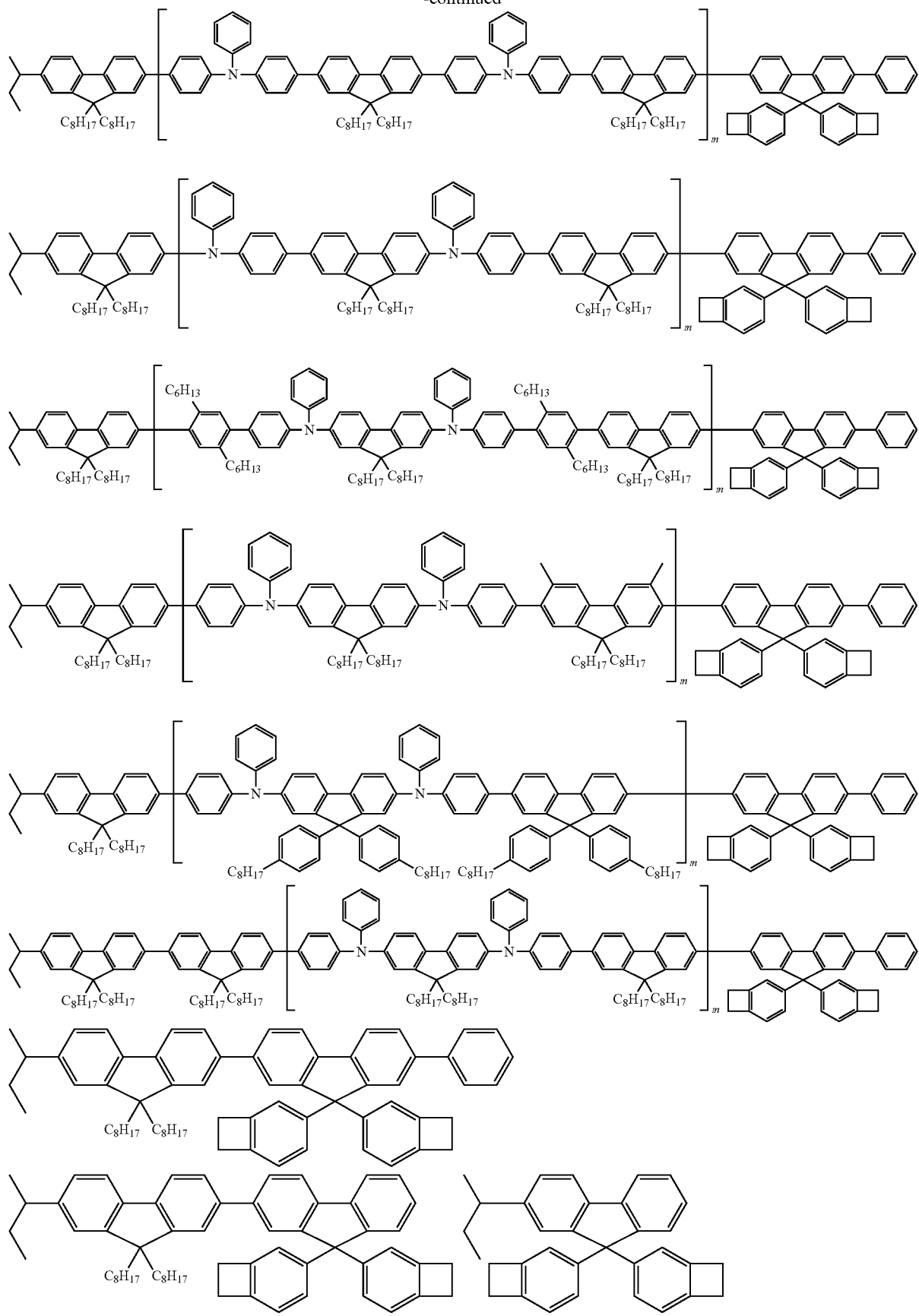

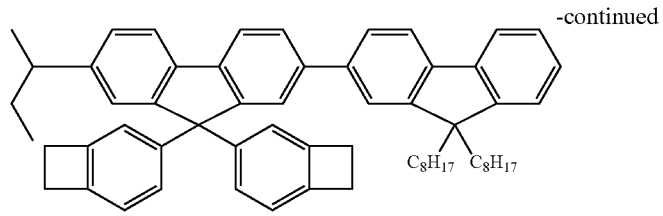

In the above formulae, n and m may be each independently an integer from 1 to 10.

The second repeating unit as a triphenylamine unit having a cross-linking group may serve as a cross-linkable unit and a charge transporting unit. Accordingly, an amino fluorene polymer according to an embodiment including such a second repeating unit may have an increased ratio of charge transporting units (high charge transporting ability) and increased cross-linking ability. Due to the inclusion of cross-linking groups, the second repeating unit may participate in a cross-linking reaction under heating and/or active energy ray radiation. This cross-linking reaction may enable formation of a more durable layer that is not dissolved by a solvent. Therefore, an organic light-emitting device using an amino fluorene polymer according to any of the embodiments including such a second repeating unit as described above may have improved emission lifetime.

For example, even when forming another layer on an amino fluorene polymer-including layer, the amino fluorene polymer-including layer may be nearly not dissolved or not dissolved at all by a solvent that is used to form a layer thereon.

When the amino fluorene polymer is a copolymer, the amino fluorene polymer may have any non-limited structures. For example, the amino fluorene polymer may be any one of a random copolymer, an alternating copolymer, a periodic copolymer, and a block copolymer. However, embodiments are not limited thereto.

A ratio of the second repeating unit may be from about 1 mole percent (mole %) or greater to about 50 mole % or less with respect to a total number of the repeating units that form the amino fluorene polymer (for example, a total number of first and second repeating units when the amino fluorene polymer includes both the first and second repeating units). If the ratio of the second repeating unit is less than 1 mole %, a layer that is insoluble in a solvent may be not formed through cross-linking reaction. If the ratio of the second repeating unit exceeds 50 mole %, an organic light-emitting device including the amino fluorene polymer may not have satisfactory lifetime improvement.

For example, the ratio of the second repeating unit may be from 5 mole % or greater to about 15 mole % or less, and in some embodiments, about 10 mole %, with respect to a total number of the repeating units of the amino fluorene polymer. However, embodiments are not limited thereto.

In certain embodiments, a total amount of the first and second repeating units may be about 100 mole %. In certain embodiments, the amino fluorene polymer may be a random copolymer represented by Formula 9. However, embodiments are not limited thereto.

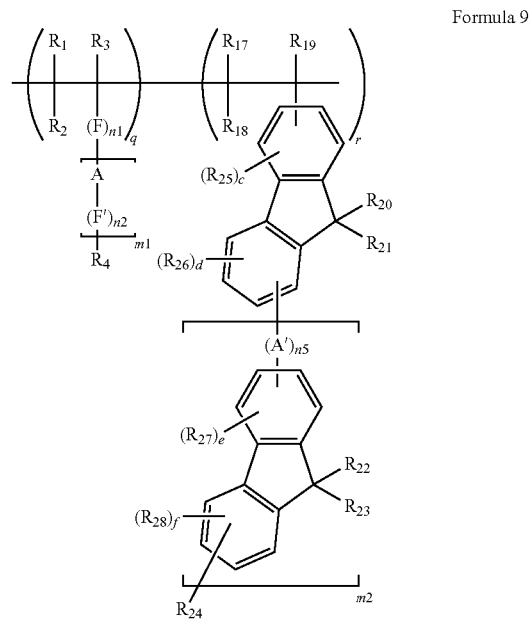

Formula 9

In Formula 9, $R_1$ to $R_4$, F, F', A, n1, n2, and m1 may be defined the same as those of Formula 1;

$R_{17}$ to $R_{28}$, c, d, e, f, A', n5, and m2 may be defined the same as those of Formula 6;

q may be an integer from 5 to 300; and r may be an integer from 1 to 300.

The amino fluorene polymer represented by Formula 9 may have sufficient durability (i.e., may be insoluble) in solvent as a result of the cross-linking. Accordingly, even when another layer is formed on an amino fluorene polymer-including layer, the amino fluorene polymer-including layer may be nearly not dissolved or not dissolved at all by a solvent used to form the layer on the amino fluorene polymer-including layer.

A ratio of each of the first and second repeating units may be adjusted by changing a ratio of monomers used in polymerization to form the amino fluorene polymer. A ratio of each of the first and second repeating units with respect to a total amount of the repeating units may be measured by nuclear magnetic resonance (NMR).

For example, the amino fluorene polymer may be formed by polymerization of monomers represented by Formula 1'. However, embodiments are not limited thereto.

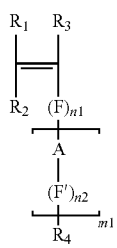

Formula 1'

In Formula 1', $R_1$ to $R_4$, F, F', A, n1, n2, and m1 may be defined the same as those of Formula 1.

The monomers for the amino fluorene polymer may be synthesized using any known synthesis method, and structures of the monomers may also be identified using NMR and liquid chromatography-mass spectroscopy (LC-MS).

Methods of polymerization for the amino fluorene polymer are not particularly limited. For example, any known methods, including radical polymerization, anionic polymerization, and cationic polymerization, may be used. For example, the amino fluorene polymer may be obtained by radical polymerization. However, embodiments are not limited thereto.

A solvent used in polymerization for the amino fluorene polymer may be selected, for example, from toluene, xylene, diethyl ether, chloroform, ethyl acetate, methylene chloride, tetrahydrofuran, acetone, acetonitrile, N, N-dimethylformamide, dimethyl sulfoxide, anisole, and hexamethylphosphorus triamide. In certain embodiments, the solvent may be selected from toluene and tetrahydrofuran. These solvents may be used either alone or in combination of at least two solvents. Monomers used in polymerization for an amino fluorene polymer according to any of the embodiments may have high solubility in the above-described solvents.

The concentration of a monomer (for example, a total concentration of monomers) in the solvent may be from about 5 percent by weight (wt %) to about 90 wt %, and in some embodiments, from about 10 wt % to about 80 wt %. However, embodiments are not limited thereto.

The polymerization temperature may be from about 40° C. to 150° C. in view of molecular weight control. However, embodiments are not limited thereto.

The polymerization reaction may be performed from about 30 minutes to about 24 hours. However, embodiments are not limited thereto.

The solvent including the monomer may be deaerated before addition of a polymerization initiator. For example, the deaeration may be freeze deaeration or deaeration using an inert gas such as nitrogen gas. However, embodiments are not limited thereto.

The polymerization initiator may be any of widely used polymerization initiators. For example, the polymerization initiator may be selected from benzophenone, benzoyl peroxide, acetyl peroxide, lauroyl peroxide, and azobisisobutyronitrile. However, embodiments are not limited thereto. The amount of the polymerization initiator used to prepare an amino fluorene polymer according to any of the above-described embodiments may be, for example, from about 0.0001 moles to about 1 mole based on 1 mole of the total monomers. However, embodiments are not limited thereto.

A main chain terminal of an amino fluorene polymer according to any of the embodiments may be appropriately defined depending on the types of monomers. For example, the main chain terminal of the amino fluorene polymer may be a hydrogen atom. However, embodiments are not limited thereto.

A synthesis method of an amino fluorene polymer according to any of the embodiments may be understood by one of ordinary skill in the art with reference to the following synthesis examples.

Organic Light-Emitting Device

An organic light-emitting device according to an embodiment will be described in greater detail with reference to FIG. 1. FIG. 1 is a cross-sectional view of an organic light-emitting device 100 according to an embodiment.

Referring to FIG. 1, the organic light-emitting device 100 includes a substrate 110, a first electrode 120, a hole injection layer 130, a hole transport layer 140, an emission layer 150, an electron transport layer 160, an electron injection layer 170, and a second electrode 180 which are sequentially stacked in the stated order. However, the organic light-emitting device 100 may have a structure not limited thereto.

The organic light-emitting device 100 may have, for example, a structure of first electrode/single layer with hole injection and hole transport functions/emission layer/electron transport layer/second electrode or first electrode/single layer with hole injection and hole transport functions/emission layer/electron transport layer/electron injection layer/second electrode.

An amino fluorene polymer according to any of the embodiments may be included in at least one organic layer between the first electrode 120 and the second electrode 180. For example, the amino fluorene polymer may be included in the hole transport layer 140 in terms of improved lifespan and high efficiency.

The amino fluorene polymer may be appropriate for an organic light-emitting device manufactured using a liquid coating method.

The organic layer including the amino fluorene polymer may be formed using a liquid coating method. For example, the organic layer including the amino fluorene polymer may be formed using a liquid coating method such as spin coating, casting, micro gravure coating, gravure coating, bar coating, roll coating, wire bar coating, dip coating, spry coating, screen printing, flexographic printing, offset printing, or ink jet printing. A solvent for the solution coating method may be any solvent able to dissolve the amino fluorene polymer.

Methods for forming the other layers except for the organic layer including the amino fluorene polymer are not specifically limited, and for example, may include a vacuum deposition method or a liquid coating method.

The substrate 110 may be any substrate used in general organic light-emitting devices. For example, the substrate 110 may be a glass substrate, a semiconductor substrate, or a plastic substrate.

The first electrode 120 may be, for example, an anode. The first electrode 120 may be formed on the substrate 110 by, for example, deposition or sputtering. For example, the first electrode 120 may be formed of a metal, an alloy, or a conductive compound that have high work function. For example, the first electrode 120 may be formed as a transmissive electrode using a transparent, high-conductivity material, such as indium tin oxide ($In_2O_3$—$SnO_2$; ITO), indium zinc oxide ($In_2O_3$—ZnO; IZO), tin oxide ($SnO_2$), or zinc oxide (ZnO). For example, the first electrode 120 may be formed of a reflective electrode using, for example, magnesium (Mg), aluminum (Al), or the like.

The hole injection layer 130 may be formed on the first electrode 120. The hole injection layer 130 may facilitate injection of holes from the first electrode 120. The hole injection layer 130 may have a thickness of about 10 nanometers (nm) to about 1,000 nm, and in some embodiments, about 10 nm to about 100 nm.

The hole injection layer 130 may be formed of a known material, for example, triphenylamine-containing poly(ether ketone) (TPAPEK), 4-isopropyl-4'-methyldiphenyliodonium tetrakis (pentafluorophenyl) borate (PPBI), N,N'-diphenyl-N,N'-bis-[4-(phenyl-m-tolyl-amino)-phenyl]-biphenyl-4,4'-diamine (DNTPD), phthalocyanine compounds, such as copper phthalocyanine, 4,4',4"-tris(3-methylphenyl phenyl amino) triphenylamine (m-MTDATA), N,N'-di(1-naphthyl)-N,N'-diphenylbenzidine (NPB), 4,4',4"-tris{N,N-diphenyl amino}triphenylamine (TDATA), 4,4',4"-tris(N,N-2-naphthylphenylamino) triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline)/poly(4-styrene sulfonate) (PANI/PSS), or the like.

The hole transport layer 140 may be formed on the hole injection layer 130. The hole transport layer 140 may include a hole transporting material with the ability to form holes. The hole transport layer 140 may have a thickness of about 10 nm to about 150 nm.

The hole transport layer 140 may be formed of an amino fluorene polymer according to any of the embodiments by a liquid coating method. The amino fluorene polymer that may improve lifetime of the organic light-emitting device 100 may be efficiently coated over a large area by liquid coating method.

The hole transport layer 140 may be formed of, in addition to an amino fluorene polymer as described above, a known material, for example, 1,1-bis[(di-4-tolylamino) phenyl] cyclohexane (TAPC), a carbazole derivative such as N-phenylcarbazole or polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-bis(naphthalen-2-yl)-N,N'-bis(phenyl)-benzidine (NPB), N,N'-bis(naphthalene-1-yl)-N,N'-bis(phenyl)-benzidine, or the like.

The emission layer 150 may be formed on the hole transport layer 140. The emission layer 150 may be a phosphorescent or fluorescent emission layer. The emission layer 150 may be formed on the hole transport layer 140 by a vacuum deposition method, a spin coating method, or an ink jet method. The emission layer 150 may have a thickness of, for example, about 10 nm to about 60 nm.

The emission layer 150 may include a known luminescent material. For example, the emission layer 150 may include a luminescent material that may emit light (phosphorescence) from triplet excitons. This may further improved emission lifetime of the organic light-emitting device 100.

In certain embodiments, the emission layer 150 may include another host material, for example, 1,3-bis(carbazole)benzene (mCP), tris(8-quinolinolinato)aluminum ($Alq_3$), 4,4'-N,N'-dicarbazole-biphenyl (CBP), poly(n-vinylcarbazole) (PVK), poly(n-vinyl carbazole), 9,10-di(naphthalene-2-yl)anthracene (AND), 9,10-di(naphthalene-2-yl)anthracene, TCTA, 1,3,5-tris(N-phenylbenzimidazole-2-yl) benzene (TPBI), 1,3,5-tris(N-phenylbenzimidazole-2-yl) benzene), 3-tert-butyl-9,10-di(naphth-2-yl) anthracene (TBADN), distyrylarylene (DSA), 4,4'-bis(9-carbazole)-2,2'-dimethylbiphenyl (dmCBP), 2,4,6-tris(diphenylamino)-1,3,5-triazine, or the like.

The emission layer 150 may be an emission layer emitting light of a specific color. For example, the emission layer 150 may be formed as a red emission layer, a green emission layer, and/or a blue emission layer.

When the emission layer 150 is a blue emission layer, the emission layer 150 may include a known blue dopant, for example, perilene, a derivative thereof, or an iridium (Ir) complex, such as bis[2-(4,6-difluorophenyl) pyridinato]picolinate iridium(III) (FIrpic).

When the emission layer 150 is a red emission layer, the emission layer 150 may include a known red dopant, for example, rubrene, a derivative thereof, 4-(dicyanomethylene)-2-methyl-6-[p-(dimethylamino)styryl]-4H-pyran (DCM), an iridium complex, such as bis(1-phenylisoquinoline)(acetylacetonate)iridium(III) ($Ir(piq)_2(acac)$), an osmium (Os) complex, a platinum complex, or the like.

When the emission layer 150 is a green emission layer, the emission layer 150 may include a known green dopant, for example, coumarin, a derivative thereof, an iridium complex, such as tris(2-phenylpyridine) iridium(III) ($Ir(ppy)_3$), tris(2-(3-p-xylyl)phenyl)pyridine iridium (III) (TEG), tris (acetylacetonato)iridium (III) ($Ir(acac)_3$), or the like.

The electron transport layer 160 may be formed on the emission layer 150. The electron transport layer 160 may be a layer including an electron transporting material. The electron transport layer 160 may be formed on the emission layer 150 by a vacuum deposition method, a spin coating method, or an inkjet method. The electron transport layer 160 may have a thickness of about 15 nm to about 50 nm.

The electron transport layer 160 may be formed of a known electron transport material, for example, tris(8-quinolinato)aluminum ($Alq_3$) and a compound having an nitrogen-containing aromatic ring. Examples of the nitrogen-containing aromatic ring are a pyridine ring-containing compound such as 1,3,5-tri[(3-pyridyl)-phen-3-yl]benzene, a triazine ring-containing compound such as 2,4,6-tris(3'-(pyridin-3-yl)biphenyl-3-yl)-1,3,5-triazine, and an imidazole ring-containing compound such as 2-(4-(N-phenylbenzoimidazolyl-1-yl-phenyl)-9,10-dinaphthylanthracene. A material for the electron transport layer 160 may be a commercially available product or may be prepared by a synthetic method. Examples of the commercially available product as a material for the electron transport layer 180 are KLET-01, KLET-02, KLET-03, KLET-10, KLET-M1 (available from Chemipro Kasei). These materials for the electron transport layer 160 may be used alone or in a combination of at least two thereof.

The electron injection layer 170 may be formed on the electron transport layer 160. The electron injection layer 170 may facilitate injection of electrons from the second electrode 180. The electron injection layer 170 may be formed on the electron transport layer 160 by a vacuum deposition method. For example, the electron injection layer 170 may have a thickness of about 0.3 nm to about 9 nm.

The electron injection layer 170 may be formed of a known electron injection material, for example, (8-quinolinato)lithium (Liq), lithium fluoride (LiF), sodium chloride (NaCl), cesium fluoride (CsF), lithium oxide ($Li_2O$), barium oxide (BaO), or the like.

The second electrode 180 may be formed on the electron injection layer 170. The second electrode 180 may be, for example, a cathode. The second electrode 180 may be formed of a metal, an alloy, or a conductive compound that have a low work function. For example, the second electrode 180 may be formed as a reflective electrolyte from a metal such as lithium (Li), magnesium (Mg), aluminum (Al), or calcium (Ca), or an alloy such as an aluminum-lithium (Al—Li) alloy, a magnesium-indium (Mg—In) alloy, or a magnesium-silver (Mg—Ag) alloy. In some embodiments, the second electrode 180 may be formed as a transmissive electrode having a thickness of about 20 nm or less, for example, from indium tin oxide (ITO), indium zinc oxide (IZO), or the like.

The organic light-emitting device 100 may be of a top-emission or rear-emission type.

Exemplary embodiments of the structure of the organic light-emitting device 100 are described above. However, embodiments are not limited to the above-described structures of the organic light-emitting device 100.

The organic light-emitting device 100 as an embodiment of the present disclosure may have any of known various structures. For example, the organic light-emitting device 100 may have a structure without at least one of the hole injection layer 130, the hole transport layer 140, the electron transport layer 160, and the electron injection layer 170. Each of these layers of the organic light-emitting device 100 may be formed as a single layer or multiple layers.

For example, the organic light-emitting device 100 may further include a hole blocking layer (not shown) disposed between the hole transport layer 140 and the emission layer 150 to prevent diffusion of triplet excitons or holes into the electron transport layer 160. For example, the hole blocking layer may be formed of an oxadiazole derived, a triazole derivative, a phenanthroline derivative, or the like.

As used herein, a $C_1$-$C_{20}$ alkyl group refers to a linear or branched saturated aliphatic hydrocarbon monovalent group having 1 to 20 carbon atoms. Non-limiting examples of the $C_1$-$C_{20}$ alkyl group are a methyl group, an ethyl group, a propyl group, an isobutyl group, a sec-butyl group, a tert-butyl group, a pentyl group, an iso-amyl group, and a hexyl group. A $C_1$-$C_{20}$ alkylene group refers to a divalent group having the same structure as the $C_1$-$C_{20}$ alkyl group.

As used herein, a $C_1$-$C_{20}$ alkoxy group refers to a monovalent group represented by —$OA_{101}$ (where $A_{101}$ is a $C_1$-$C_{20}$ alkyl group, as described above. Non-limiting examples of the $C_1$-$C_{20}$ alkoxy group are a methoxy group, an ethoxy group, and an isopropyloxy group.

As used herein, a $C_1$-$C_{20}$ oxyalkylene group refers to a $C_1$-$C_{20}$ alkylene group of which carbon atoms are partially substituted by oxygen.

As used herein, a $C_3$-$C_{16}$ cycloalkyl group refers to a monovalent, monocyclic hydrocarbon group having 3 to 16 carbon atoms as ring-forming atoms. Non-limiting examples of the $C_3$-$C_{16}$ cycloalkyl group are a cyclopropyl group, a cyclobutyl group, a cyclopentyl group, a cyclohexyl group, and a cycloheptyl group. A $C_3$-$C_{16}$ cycloalkylene group refers to a divalent group having the same structure as the $C_3$-$C_{16}$ cycloalkyl group.

As used herein, a $C_3$-$C_{16}$ cycloalkoxy group refers to a monovalent group represented by the formula of —$OA_{102}$ (wherein $A_{102}$ is a $C_3$-$C_{16}$ cycloalkyl group as described above). Non-limiting examples of the $C_3$-$C_{16}$ cycloalkoxy group are a cyclopropoxy group, a cyclobutoxy group, and a cyclopentoxy group.

As used herein, a $C_3$-$C_{16}$ oxycycloalkylene group refers to a $C_3$-$C_{16}$ cycloalkylene group of which some carbon atoms are replaced by oxygen atoms.

As used herein, a $C_6$-$C_{30}$ aryl group refers to a monovalent, aromatic carbocyclic group having 6 to 30 carbon atoms as ring-forming atoms, and a $C_6$-$C_{30}$ arylene group refers to a divalent, aromatic carbocyclic group having 6 to 30 carbon atoms. Non-limiting examples of the $C_6$-$C_{30}$ aryl group are a phenyl group, a naphthyl group, an anthracenyl group, a phenanthrenyl group, a pyrenyl group, and a chrysenyl group. When a $C_6$-$C_{30}$ aryl group and a $C_6$-$C_{30}$ arylene group include at least two rings, the rings may be fused to each other.

As used herein, a $C_6$-$C_{30}$ aryloxy group refer to a group represented by —$OA_{103}$ (wherein $A_{103}$ is a $C_6$-$C_{30}$ aryl group as described above).

As used herein, a $C_6$-$C_{30}$ oxyarylene group refers to a $C_6$-$C_{30}$ arylene group of which some carbon atoms are replaced by oxygens.

As used herein, a $C_5$-$C_{30}$ heteroaryl group refers to a monovalent, aromatic heterocyclic group having 5 to 30 carbon atoms and at least one hetero atom selected from N, O, Si, P, and S as ring-forming atoms. A $C_5$-$C_{30}$ heteroarylene group refers to a divalent, aromatic heterocarbocyclic group having 5 to 30 carbon atoms and at least one hetero atom selected from N, O, Si, P, and S as ring-forming atoms. Non-limiting examples of the $C_3$-$C_{30}$ heteroaryl group are a pyridinyl group, a pyrimidinyl group, a pyrazinyl group, a pyridazinyl group, a triazinyl group, a quinolinyl group, and an isoquinolinyl group. When a $C_5$-$C_{30}$ heteroaryl and a $C_5$-$C_{30}$ heteroarylene include at least two rings, the rings may be fused to each other.

As used herein, a $C_7$-$C_{40}$ aralkyl group refers to a monovalent hydrocarbon group including alkyl groups with aryl groups as substituents, wherein a total number of carbon atoms of the alkyl groups and the aryl groups is 7 to 40. Non-limiting examples of the $C_7$-$C_{40}$ aralkyl group are a benzyl group, a phenylethyl group, a methylbenzyl group, and a naphthylmethyl group.

At least one of substituent(s) of the substituted groups defined above may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, and a $C_2$-$C_{60}$ heteroarylalkyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, and a $C_2$-$C_{60}$ heteroarylalkyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, —$N(Q_{21})(Q_{22})$, —$Si(Q_{23})(Q_{24})(Q_{25})$, and —$B(Q_{26})(Q_{27})$; and
—$N(Q_{31})(Q_{32})$, —$Si(Q_{33})(Q_{34})(Q_{35})$, and —$B(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ may each independently be selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, and a $C_1$-$C_{60}$ heteroarylthio group.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

As used herein, "a halogen atom" may be selected from a fluorine atom, a chlorine atom, a bromine atom, and an iodine atom.

One or more embodiments of amino fluorene polymers and organic light-emitting devices according to the present disclosure will now be described in detail with reference to the following examples. However, these examples are only for illustrative purposes and are not intended to limit the scope of the one or more embodiments of the present disclosure. In the following synthesis examples, the expression that "'B', instead of 'A', was used" means that the amounts of 'A' and 'B' were the same in equivalent amounts.

EXAMPLES

In the following synthesis examples, analysis was performed according to the following methods.

(1) Measurement of Number Average Molecular Weight, Weight Average Molecular Weight, and Polydispersity Index (PDI)

Number average molecular weight (Mn), weight average molecular weight (Mw) and polydispersity index (PDI, Mw/Mn) were measured by gel permeation chromatography (GPC) using polystyrene as a standard sample under the following conditions.

Analysis system: Prominence (available from Shimadzu)
Column: PLgel MIXED-B (available from Polymer Laboratories)
Column temperature: 40° C.
Flow rate: 1.0 mL/min
Injection volume: 20 microliters (μL)
Solvent: Tetrahydrofuran (THF) (concentration: about 0.05 wt %)
Detector: UV-VIS detector (SPD-10AV, available from Shimadzu)
Standard sample: Polystyrene Synthesis Example 1: Synthesis of Compound 100

1) Synthesis of Monomer A
Monomer A was synthesized according to the following Reaction Scheme A.

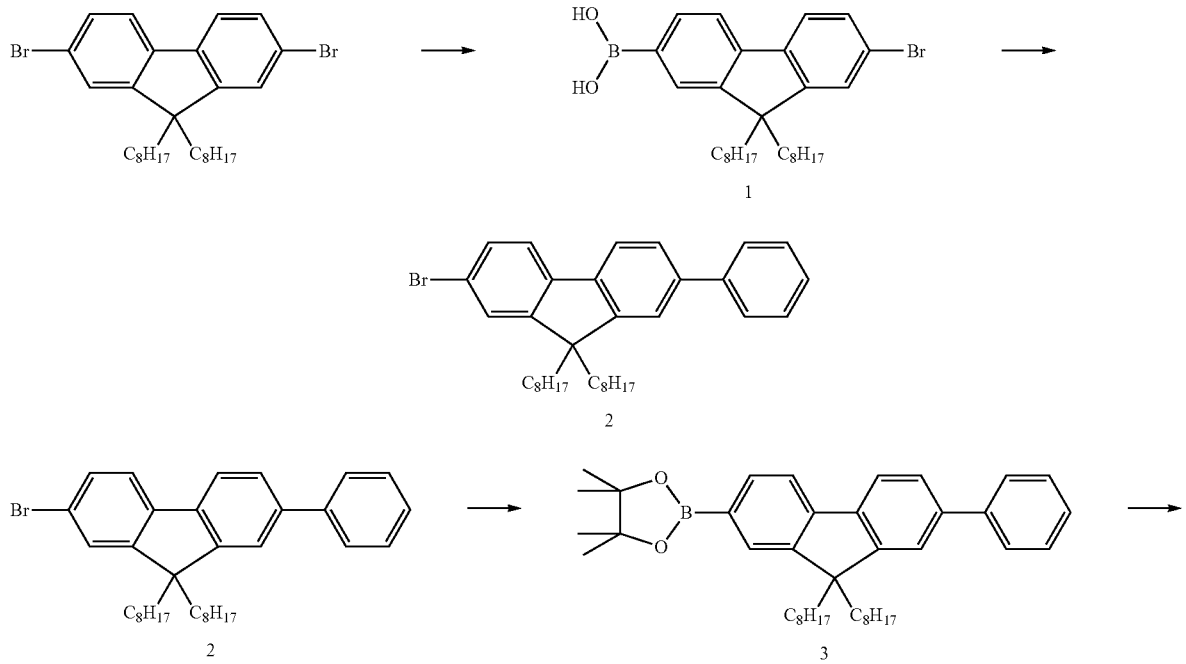

Reaction Scheme A

-continued
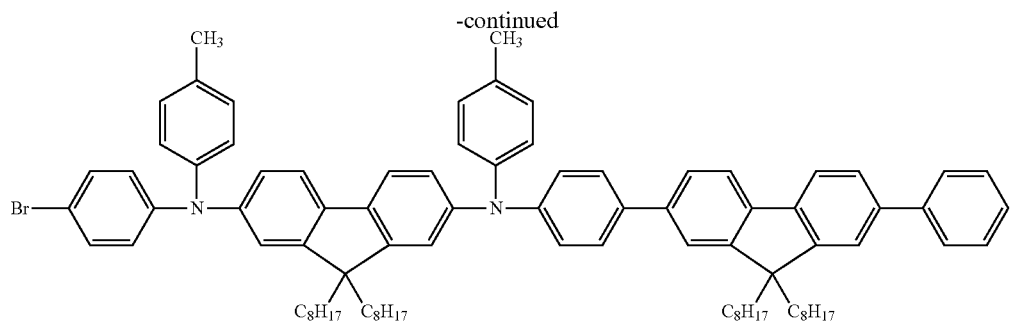
4
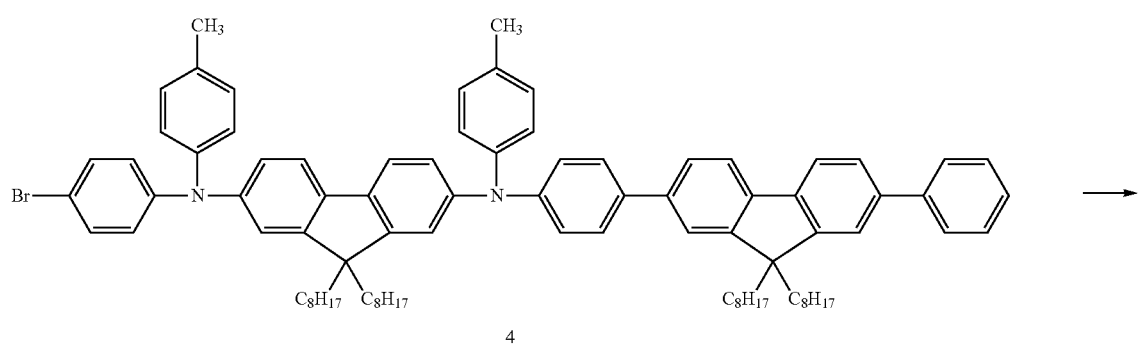
4
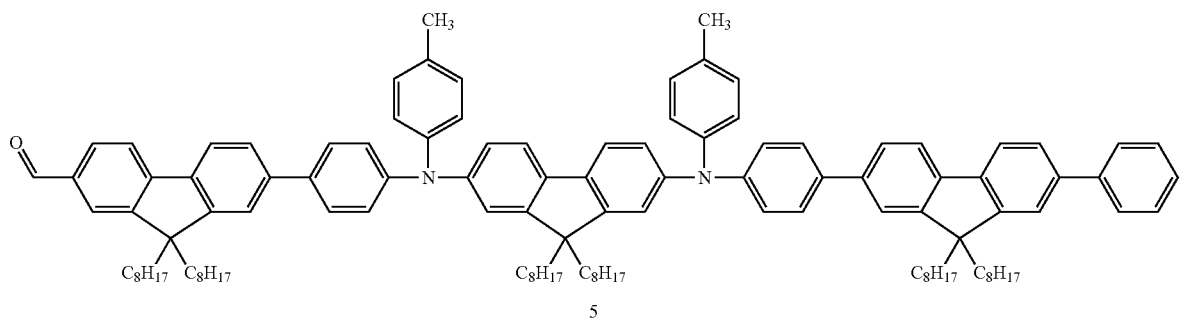
5
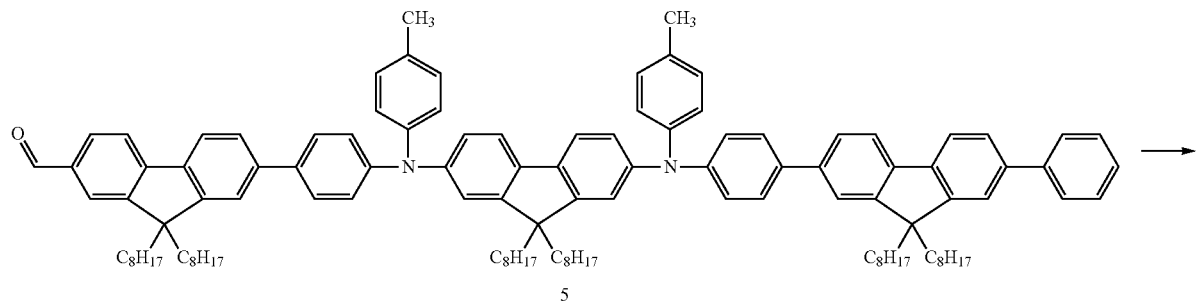
5
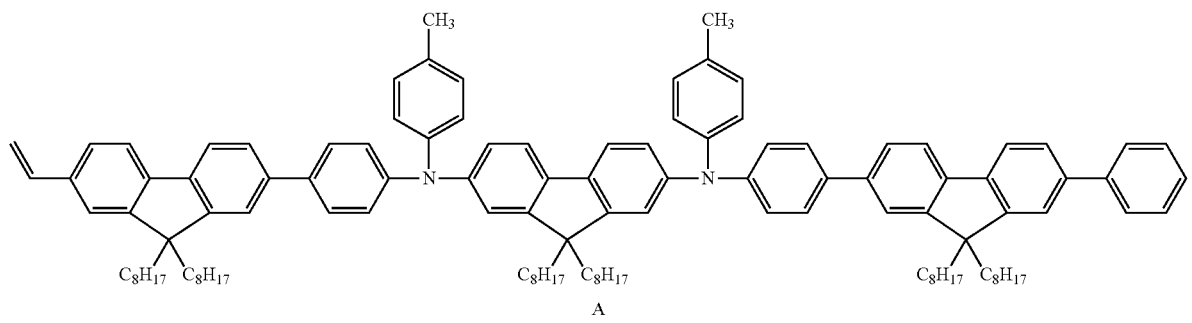
A 50.00 grams (g) (91.17 millimoles, mmol) of 2,7-dibromo-9,9-dioctylfluorene was placed into a 2 liter (L), 3-necked flask, followed by purging the interior of the flask with argon (Ar). After adding 750 milliliters (mL) of tetrahydrofuran into the flask, the flask was cooled down in an acetone/dry ice bath to about −75° C., and the resulting mixture was stirred for about 15 minutes. 36.12 mL (95.72 mmol) of a 1.6 molar (M) solution of n-butyl lithium in hexane was dropwise added into the flask, the mixture was stirred for about 1 hour. 20.58 mL (109.40 mmol) of triisopropyl borate was added into the flask, and the mixture was stirred at room temperature for about 3 hours. Upon completion of the reaction, water was added to the reaction mixture, followed by extraction with ethyl acetate to obtain an organic phase, and the resulting organic phase was concentrated to obtain a solid. This solid was recrystallized using chloroform and hexane, thereby obtaining Compound 1.

Next, 15.00 g (29.22 mmol) of Compound 1, 6.56 g (32.14 mmol) of iodobenzene, 1.01 g (0.88 mmol) of tetrakis(triphenylphosphine)palladium (0), and 24.77 g (233.75 mmol) of sodium carbonate were placed into a 500-mL, 3-necked flask, followed by purging the interior of the flask with argon. 15 mL of ethanol, 100 mL of water, and 116 mL of toluene were placed into the flask, and the mixture was stirred at about 85° C. for about 3 hours. Upon completion of the reaction, the reaction mixture was cooled to room temperature, and the impurities were removed by filtration using a Celite (Registered trademark). Water was then added to the resulting filtrate, followed by extraction with toluene to obtain an organic phase, and the organic phase was concentrated. The resulting concentrate was purified by column chromatography, thereby obtaining Compound 2.

15.00 g (27.49 mmol) of Compound 2, 7.68 g (30.24 mmol) of pinacol diborane, 0.34 g (0.41 mmol) of a 1,1'-bis(diphenylphosphino)ferrocene-palladium(II) dichloride dichloromethane complex (Pd(dppf)Cl$_2$.CH$_2$Cl$_2$), and 8.09 g (82.47 mmol) of potassium acetate were placed into a 300-mL, 3-necked flask, followed by purging the interior of the flask with argon. 110 mL of anhydrous 1,4-dioxane was added into the flask, and the resulting mixture was stirred at about 100° C. for about 1 hour. Upon completion of the reaction, the reaction mixture was cooled to room temperature, and the impurities were removed by filtration using a Celite. 10 g of activated carbon was added into the resulting filtrate, followed by stirring at about 100° C. for about 1 hour and removing the activated carbon using a Celite. The resulting filtrate was concentrated to obtain a solid. This solid was then washed at room temperature with 25 mL of acetonitrile, thereby obtaining Compound 3.

3.90 g (6.59 mmol) of Compound 3, 6.00 g (6.59 mmol) of N,N-bis(4-bromophenyl)-N,N-bis(4-methylphenyl)-9,9-dioctyl-9H-fluorene-2,7-diamine, and 0.23 g (0.33 mmol) of bis(triphenylphosphine)palladium(II) dichloride were placed into a 500-mL, 3-necked flask, followed by purging the interior of the flask with argon. 3.88 g (26.35 mmol) of tetraethyl ammonium hydroxide and 300 mL of anhydrous toluene were placed into the flask, and the resulting mixture was stirred at about 100° C. for about 3 hours. Upon completion of the reaction, the reaction mixture was cooled to room temperature, and the impurities were removed by filtration using a Celite. Water was then added to the resulting filtrate, followed by extraction with toluene to obtain an organic phase, and the organic phase was concentrated. The resulting concentrate was purified by column chromatography, thereby obtaining a light-green solid. This solid was recrystallized using tetrahydrofuran and methanol, thereby obtaining Compound 4.

4.00 g (3.08 mmol) of Compound 4, 1.65 g (3.02 mmol) of 9,9-dioctyl-7-(4,4,5,5-tetramethyl-1,3,2-dioxaborolan-2-yl)-9H-fluorene-2-carboxaldehyde, 0.035 g (0.15 mmol) of palladium (II) acetate, and 0.22 g (0.62 mmol) of tris(2-methoxyphenyl)phosphine were placed into a 50-mL, 3-necked flask, followed by purging the interior of the flask with argon. 1.82 g (2.40 mmol) of tetraethyl ammonium hydroxide and 10 mL of anhydrous toluene were placed into the flask, and the resulting mixture was stirred at about 100° C. for about 4 hours. Upon completion of the reaction, the reaction mixture was cooled to room temperature, and the impurities were removed by filtration using a Celite. Water was then added to the resulting filtrate, followed by extraction with toluene to obtain an organic phase, and the organic phase was concentrated. The resulting concentrate was purified by column chromatography, thereby obtaining Compound 5.

3.80 g (2.32 mmol) of Compound 5 and 1.31 g (3.26 mmol) of methyltriphenylphosphonium iodide were placed into a 50-mL, 3-necked flask, followed by purging the interior of the flask with argon. After adding 26 mL of tetrahydrofuran into the flask, the flask was cooled down on an ice bath to about 0° C., 0.34 g (3.01 mmol) of potassium tert-butoxide was added thereto, and the resulting mixture was stirred. Upon completion of the reaction, water was added to the reaction mixture, followed by extraction with toluene to obtain an organic phase, and the resulting organic phase was concentrated. The resulting concentrate was purified by column chromatography to obtain a light-yellow solid. This solid was dissolved in tetrahydrofuran and then re-precipitated with methanol, thereby obtaining monomer A.

The monomer A was identified by proton nuclear magnetic resonance (H$^1$-NMR).

$^1$H-NMR (300 MHz, CDCl$_3$): δ 7.77-7.36 (m, 23H), 7.10-6.90 (m, 16H), 6.81 (dd, J=17.4 Hz, 10.8 Hz, 1H), 5.80 (d, J=17.4 Hz, 1H), 5.26 (d, J=11.4 Hz, 1H), 2.35 (s, 6H), 2.06-1.96 (m, 8H), 1.83-1.77 (m, 2H), 1.53-1.06 (m, 60H), 0.88-0.71 (m, 30H).

2) Synthesis of Monomer B

Monomer B was synthesized according to the following Reaction Scheme B.

Reaction Scheme B

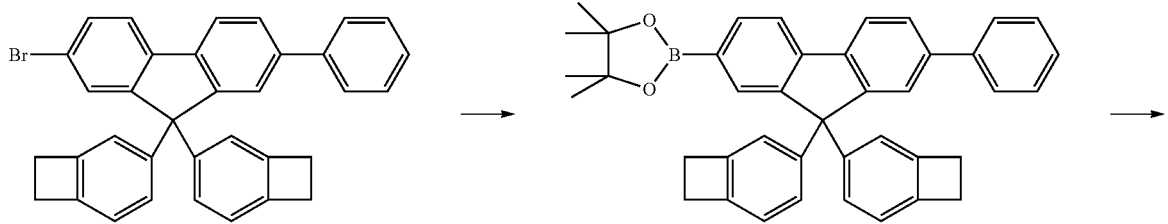

-continued
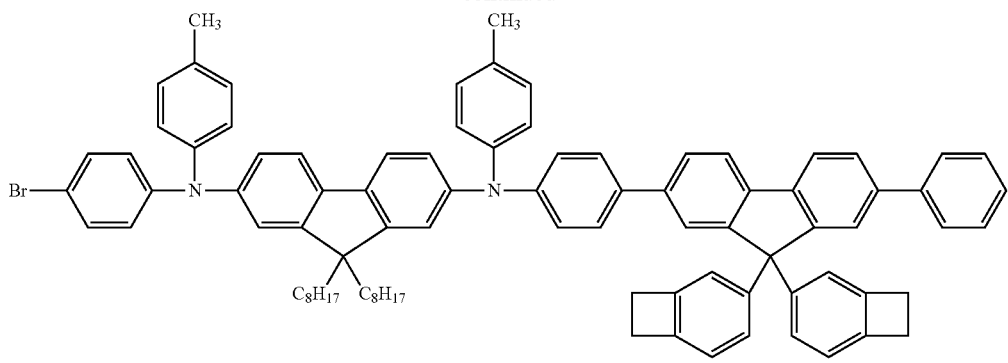
8
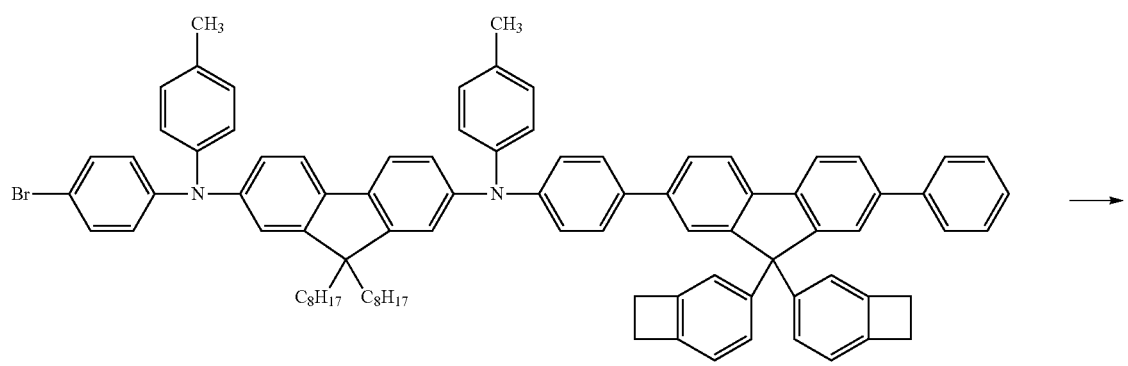
8
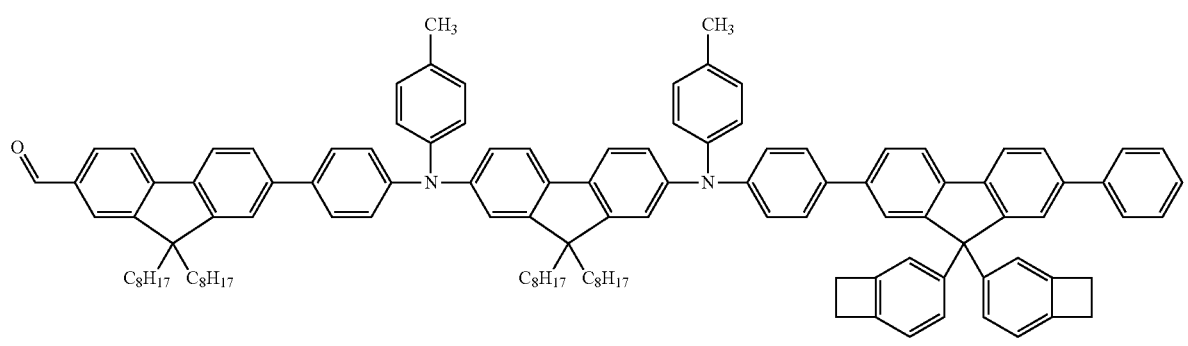
9
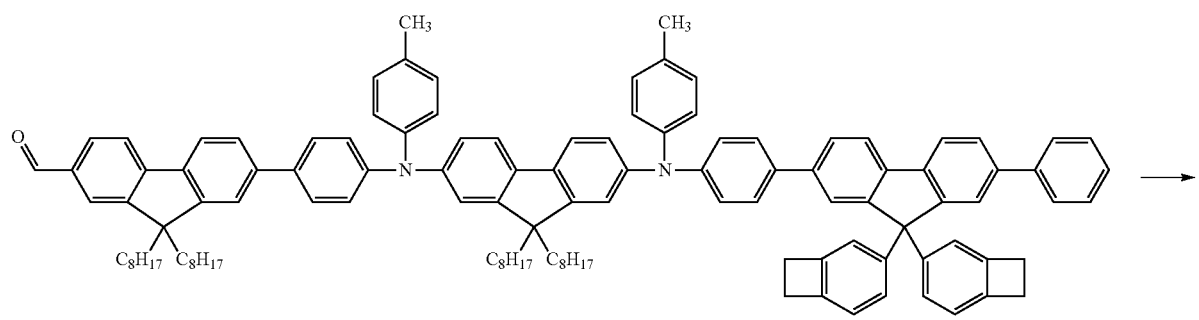
9

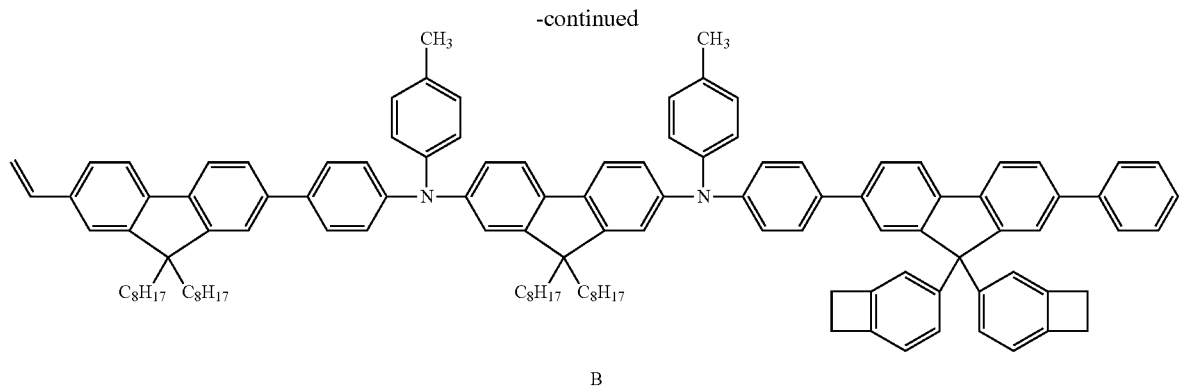

B 10.00 g (19.03 mmol) of Compound 6, 5.80 g (22.83 mmol) of pinacol diborane, 0.56 g (0.68 mmol) of Pd(dppf)Cl$_2$.CH$_2$Cl$_2$, and 5.60 g (57.09 mmol) of potassium acetate were placed into a 3-mL, 3-necked flask, followed by purging the interior of the flask with argon. 100 mL of anhydrous 1,4-dioxane was placed into the flask, and the resulting mixture was stirred at about 100° C. for about 1 hour. Upon completion of the reaction, the reaction mixture was cooled to room temperature, and the impurities were removed by filtration using a Celite. 10 g of activated carbon was placed into the resulting filtrate, followed by stirring at about 100° C. for about 1 hour and removing the activated carbon using a Celite. The resulting filtrate was concentrated to obtain a solid. This solid was then washed at room temperature with 25 mL of acetonitrile, thereby obtaining Compound 7.

0.95 g (1.66 mmol) of Compound 7, 1.51 g (1.66 mmol) of N,N-bis(4-bromophenyl)-N,N-bis(4-methylphenyl)-9,9-dioctyl-9H-fluorene-2,7-diamine, and 0.06 g (0.09 mmol) of bis(triphenylphosphine)palladium(II) dichloride were placed into a 100-mL, 3-necked flask, followed by purging the interior of the flask with argon. 2.44 g (16.59 mmol) of tetraethyl ammonium hydroxide and 47 mL of anhydrous toluene were placed into the flask, and the resulting mixture was stirred at about 100° C. for about 3 hours. Upon completion of the reaction, the reaction mixture was cooled to room temperature, and the impurities were removed by filtration using a Celite. Water was then added to the resulting filtrate, followed by extraction with toluene to obtain an organic phase, and the organic phase was concentrated. The resulting concentrate was purified by column chromatography, thereby obtaining a light-green solid. This solid was recrystallized using tetrahydrofuran and methanol, thereby obtaining Compound 8.

1.0 g (0.60 mmol) of Compound 8, 0.33 g (0.60 mmol) of 9,9-dioctyl-7-(4,4,5,5-tetramethyl-1,3,2-dioxaborolan-2-yl)-9H-fluorene-2-carboxaldehyde, 0.007 g (0.03 mmol) of palladium (II) acetate, and 0.04 g (0.20 mmol) of tris(2-methoxyphenyl)phosphine were placed into a 50-mL, 3-necked flask, followed by purging the interior of the flask with argon. 0.35 g (2.40 mmol) of tetraethyl ammonium hydroxide and 10 mL of anhydrous toluene were placed into the flask, and the resulting mixture was stirred at about 100° C. for about 4 hours. Upon completion of the reaction, the reaction mixture was cooled to room temperature, and the impurities were removed by filtration using a Celite. Water was then added to the resulting filtrate, followed by extraction with toluene to obtain an organic phase, and the organic phase was concentrated. The resulting concentrate was purified by column chromatography, thereby obtaining Compound 9.

0.73 g (0.45 mmol) of Compound 9 and 0.25 g (0.63 mmol) of methyltriphenylphosphonium iodide were placed into a 100-mL, 3-necked flask, followed by purging the interior of the flask with argon. After adding 50 mL of tetrahydrofuran into the flask, the flask was cooled down on an ice bath to about 0° C., 0.06 g (0.59 mmol) of potassium tert-butoxide was added thereto, and the resulting mixture was stirred. Upon completion of the reaction, water was added to the reaction mixture, followed by extraction with toluene to obtain an organic phase, and the resulting organic phase was concentrated. The resulting concentrate was purified by column chromatography to obtain a light-yellow solid. This solid was dissolved in tetrahydrofuran and then re-precipitated with methanol, thereby obtaining monomer B.

The monomer B was identified by H$^1$-NMR.

$^1$H-NMR (300 MHz, CDCl$_3$): δ 7.81-6.90 (m, 46H), 6.81 (dd, J=17.4 Hz, 10.8 Hz, 1H), 5.80 (d, J=17.4 Hz, 1H), 5.26 (d, J=11.4 Hz, 1H), 3.09 (s, 8H), 2.35 (s, 6H), 2.01-1.96 (m, 4H), 1.80-1.75 (m, 4H), 1.25-1.05 (m, 42H), 0.87-0.69 (m, 12H).

3) Synthesis of Compound 100

Compound 100 having a structure represented by the following formula was synthesized using the monomer A and monomer B synthesized as described above.

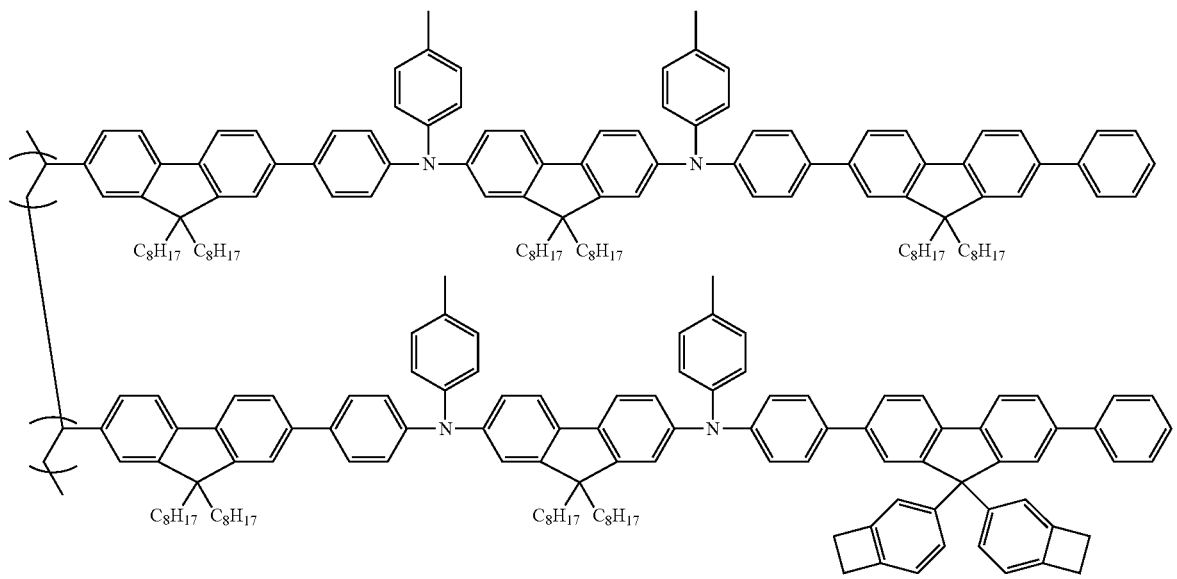

Compound 100

1,000 milligrams (mg) of the monomer A, 105.0 mg of the monomer B, 2.0 mg of azobisisobutyronitrile, and 2.8 mL of toluene were placed into a Schlenk flask, followed by bubbling, freeze degassing, and heating with stirring at about 80° C. for about 6.5 hours. The reaction mixture was cooled to room temperature, followed by re-precipitation seven times with tetrahydrofuran as a good solvent and methanol and acetone as bad solvents. The resulting precipitate was vacuum-dried, thereby obtaining 0.85 g of Compound 100 (having a ratio (Aa:Bb) of subunits Aa from the monomer A to subunits Bb from the monomer B of 90:10) as a random copolymer of the monomer A and monomer B. Compound 100 had a number average molecular weight (Mn) of about 35,800 Daltons (Da), a weight average molecular weight (Mw) of about 74,600 Da, and a polydispersity index (Mw/Mn) of about 2.08.

Synthesis Example 2: Synthesis of Compound 101

1) Synthesis of Monomer C

Monomer C was synthesized according to the following Reaction Scheme C.

Reaction Scheme C

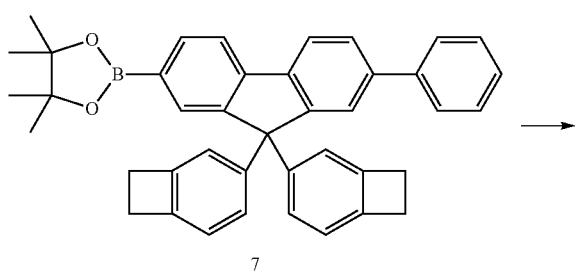

Compound 10 was synthesized in the same manner as in the synthesis of Compound 9, except that Compound 7, instead of Compound 8, was used. Monomer C was synthesized in the same manner as in the synthesis of monomer B, except that Compound 10, instead of Compound 9, was used.

The monomer C was identified by $H^1$-NMR.

$^1$H-NMR (300 MHz, CDCl$_3$): δ 7.84 (d, J=7.8, 2H), 7.71-7.50 (m, 10H), 7.44-7.20 (m, 9H), 6.70-6.93 (m, 2H), 6.81 (dd, J=17.4 Hz, 10.8 Hz, 1H), 5.80 (d, J=18.0 Hz, 1H), 5.24 (d, J=11.4 Hz, 1H), 3.09 (s, 8H), 2.00-1.95 (m, 4H), 1.21-1.05 (m, 20H), 0.82-0.66 (m, 10H).

2) Synthesis of Compound 101

Compound 101 having a structure represented by the following formula, as a random copolymer of the monomer A and the monomer C, was synthesized in the same manner as in the synthesis of Compound 100, except that the monomer C, instead of the monomer B, was used. Compound 101 had a ratio (Aa:Cc) of subunits Aa from the monomer A to subunits Cc from the monomer C of 90:10. Compound 101 had a number average molecular weight (Mn) of about 58,100 Da, a weight average molecular weight (Mw) of about 155,500 Da, and a polydispersity index (Mw/Mn) of about 2.67.

Compound 101
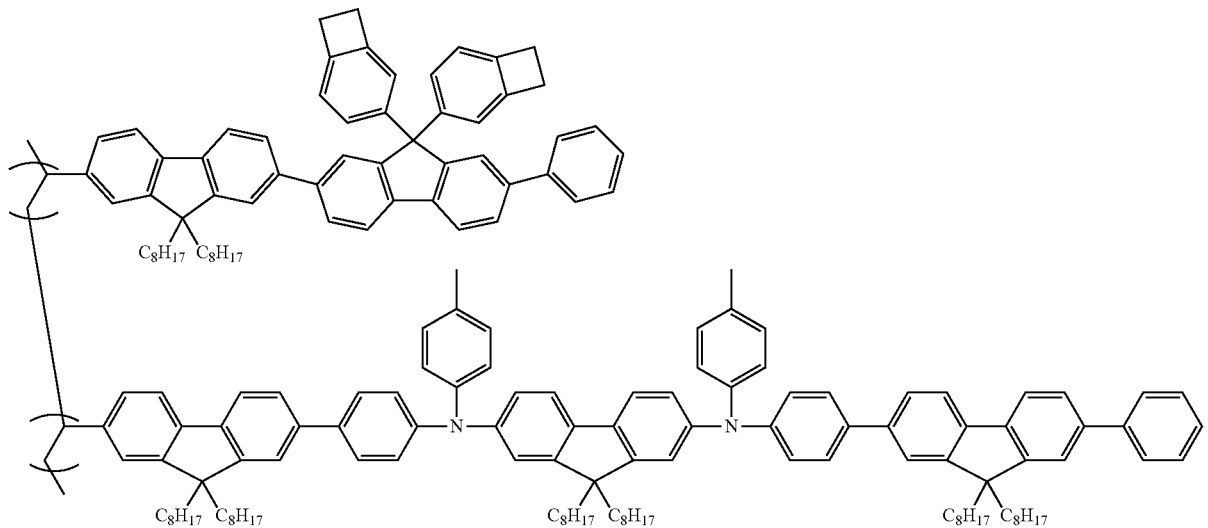
Synthesis Example 3: Synthesis of Compound 102
1) Synthesis of Monomer D
Monomer D was synthesized according to the following Reaction Scheme D.
Reaction Scheme D
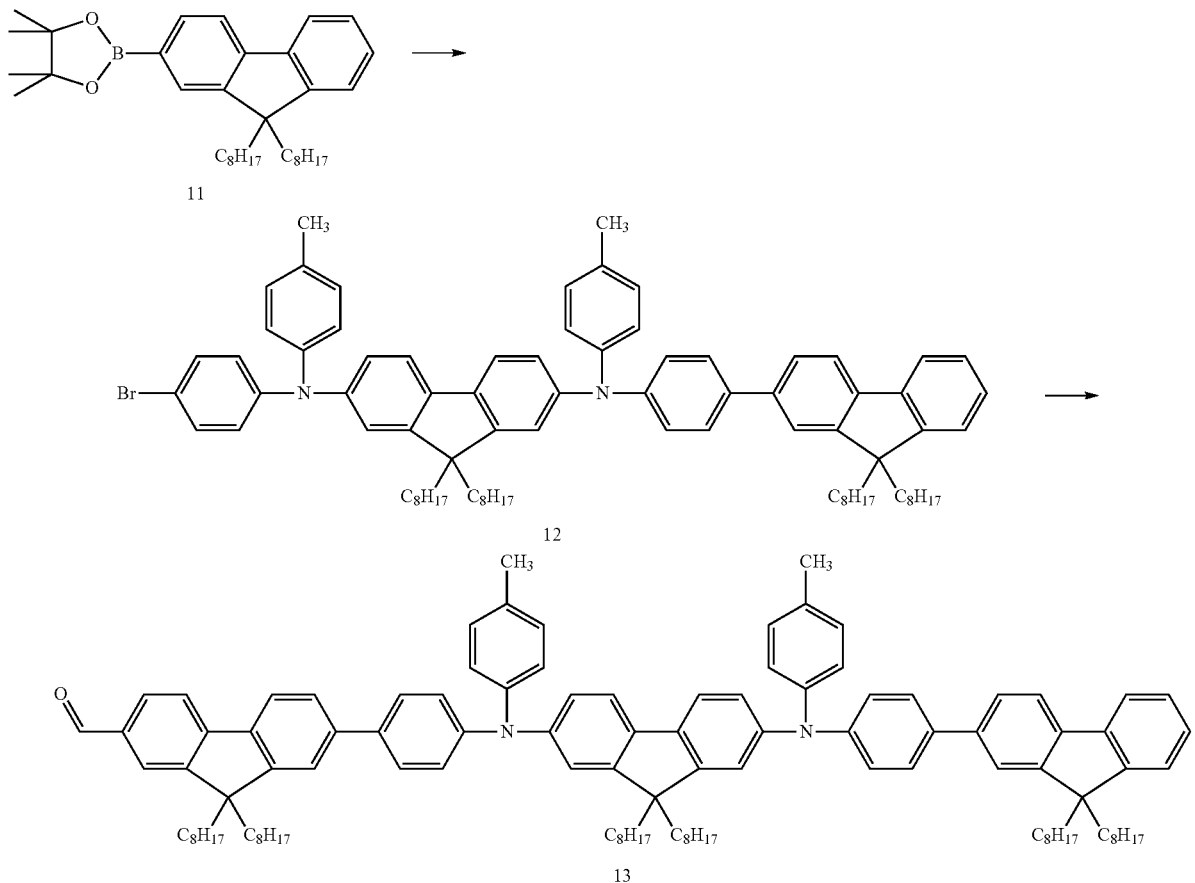

-continued

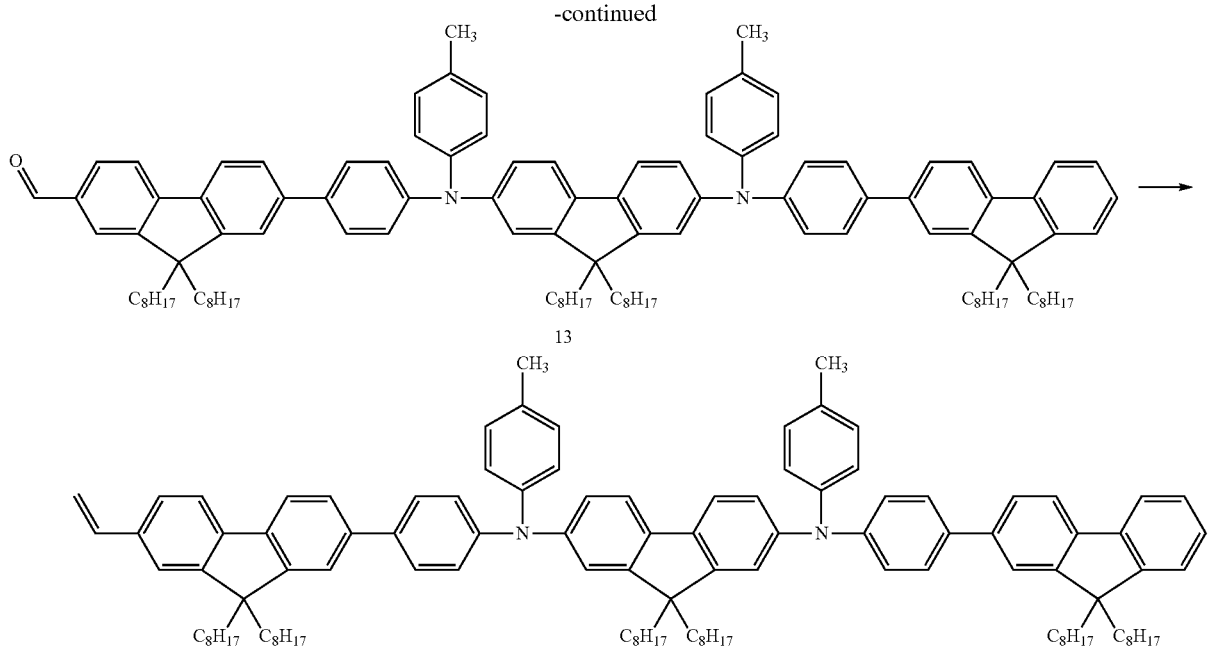

Compound 12 was synthesized in the same manner as in the synthesis of Compound 8, except that Compound 11, instead of Compound 7, was used. Compound 13 was synthesized in the same manner as in the synthesis of Compound 9, except that Compound 12, instead of Compound 8, was used. Monomer D was synthesized in the same manner as in the synthesis of the monomer B, except that Compound 13, instead of Compound 9, was used.

The monomer D was identified by H¹-NMR.

$^1$H-NMR (300 MHz, CDCl$_3$): δ 7.74-7.63 (m, 4H), 7.56-7.48 (m, 10H), 7.41-7.28 (m, 5H), 7.19-7.09 (m, 16H), 6.81 (dd, J=17.4 Hz, 10.8 Hz, 1H), 5.80 (d, J=17.4 Hz, 1H), 5.26 (d, J=11.4 Hz, 1H), 2.35 (s, 6H), 2.01-1.96 (m, 8H), 1.82-1.77 (m, 4H), 1.30-1.13 (m, 60H), 0.88-0.67 (m, 30H).

2) Synthesis of Monomer E

Reaction Scheme E

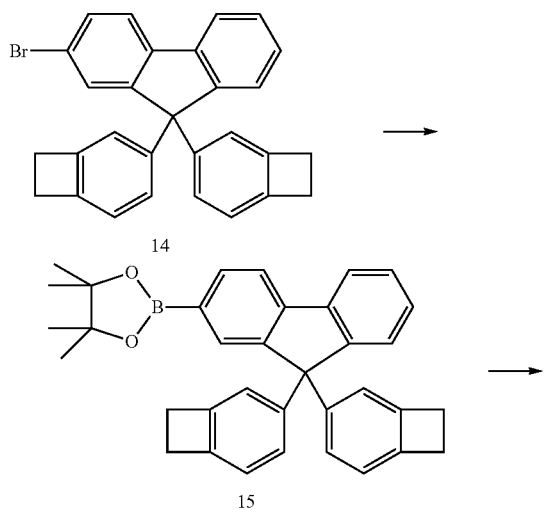

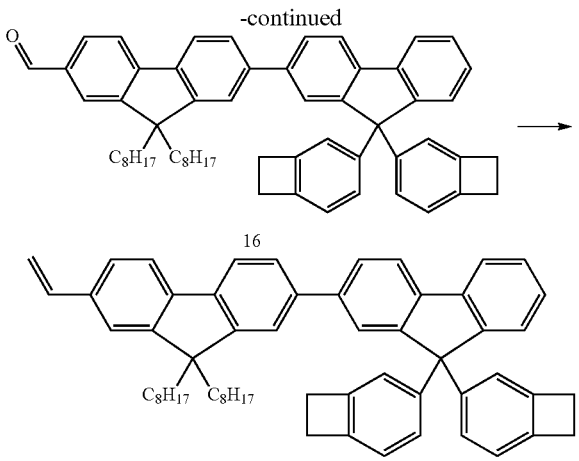

Compound 15 was synthesized in the same manner as in the synthesis of Compound 7, except that Compound 14, instead of Compound 6, was used. Compound 16 was synthesized in the same manner as in the synthesis of Compound 9, except that Compound 15, instead of Compound 8, was used. Monomer E was synthesized in the same manner as in the synthesis of the monomer B, except that Compound 16, instead of Compound 9, was used.

The monomer E was identified by H¹-NMR.

$^1$H-NMR (300 MHz, CDCl$_3$): δ 7.83-7.63 (m, 2H), 7.54-7.50 (m, 4H), 7.43-7.23 (m, 7H), 7.18-7.16 (m, 2H), 6.95-6.91 (m, 4H), 6.81 (dd, J=17.4 Hz, 10.8 Hz, 1H), 5.80 (d, J=18.0 Hz, 1H), 5.24 (d, J=11.4 Hz, 1H), 3.09 (s, 8H), 2.00-1.94 (m, 7H), 1.21-1.04 (m, 20H), 0.81-0.64 (m, 10H).

3) Synthesis of Compound 102

Compound 102 having a structure represented by the following formula as a random copolymer of the monomer D and the monomer E was synthesized in the same manner as in the synthesis of Compound 100, except that the monomers D and E, instead of the monomers A and B, were used. Compound 102 had a ratio (Dd:Ee) of subunits Dd from the monomer D and subunits Ee from the monomer E of 90:10. Compound 102 had a number average molecular weight (Mn) of about 74,000 Da, a weight average molecular weight (Mw) of about 195,000 Da, and a polydispersity index (Mw/Mn) of about 2.60.

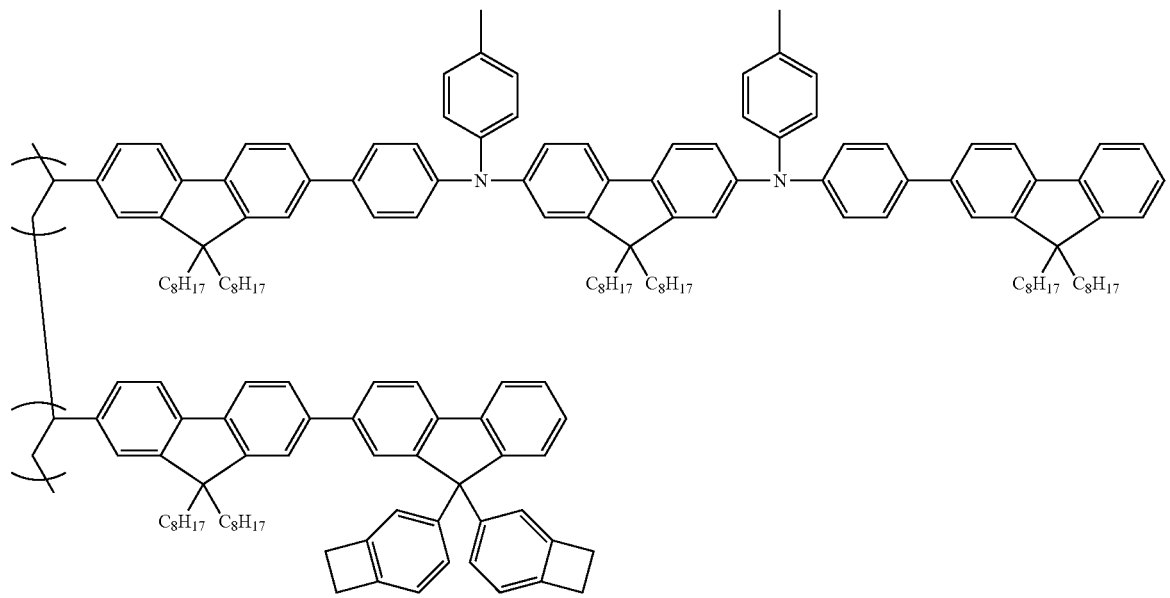

Compound 102

Synthesis Example 4: Synthesis of Compound 103

1) Synthesis of Monomer F

Monomer F was synthesized according to the following Reaction Scheme F.

Reaction Scheme F

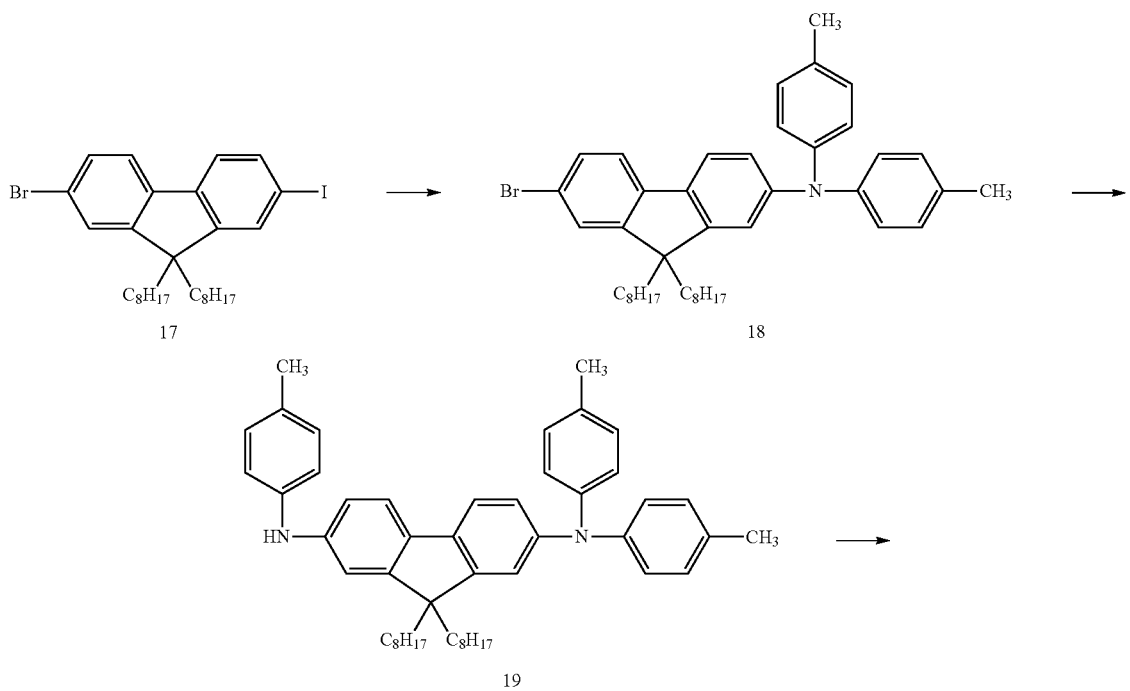

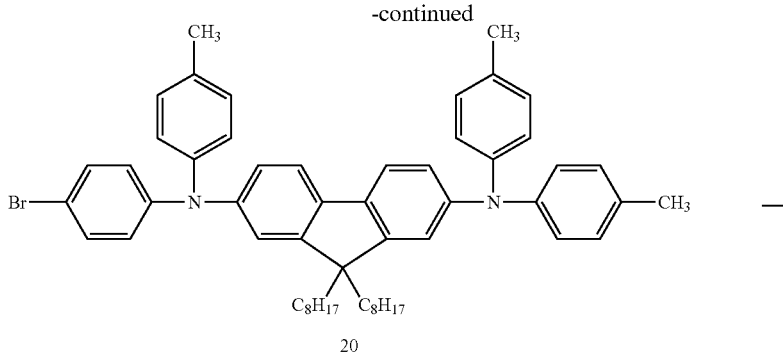

20

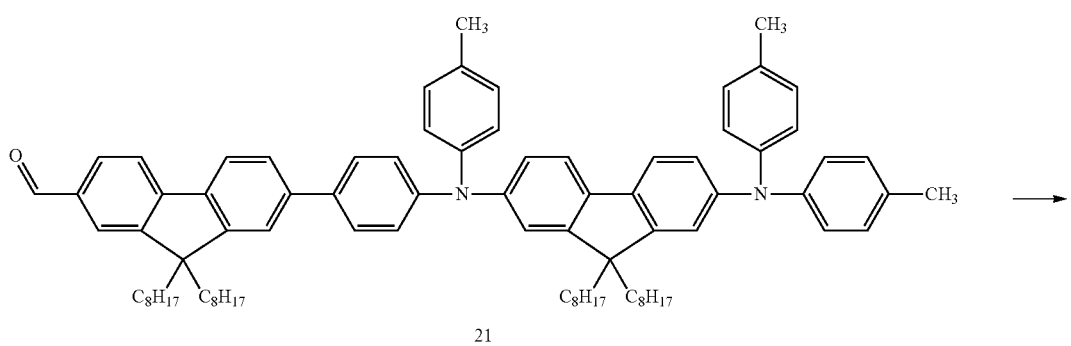

21

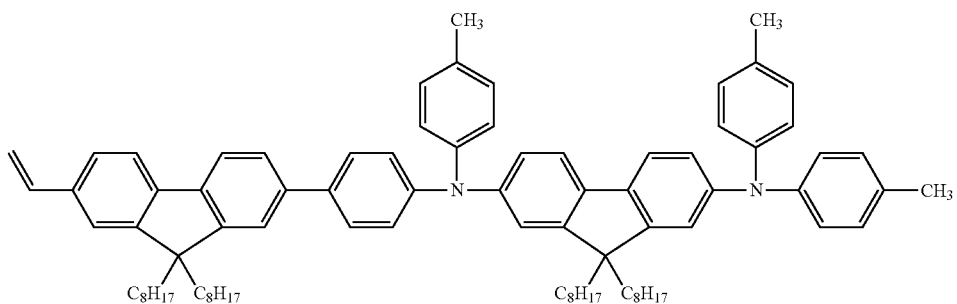

F 1.66 g (2.79 mmol) of Compound 17, 0.50 g (2.53 mmol) of ditolylamine, 0.02 g (0.13 mmol) of copper (I) iodide (CuI), 0.06 g (0.51 mmol) of cyclohexanediamine, and 0.54 g (5.58 mmol) of sodium tert-butoxide were placed into a 50-mL, 3-necked flask, followed by purging the interior of the flask with argon. 5 mL of anhydrous 1,4-dioxane was added into the flask, and the resulting mixture was stirred at about 100° C. for about 8 hours. Upon completion of the reaction, the reaction mixture was cooled to room temperature, impurities were removed by filtration using a Celite, and the resulting filtrate was concentrated. The resulting concentrate was purified by column chromatography, to thereby obtain Compound 18.

1.0 g (1.50 mmol) of Compound 18, 0.21 g (1.96 mmol) of toluidine, 0.07 g (0.08 mmol) of tris(dibenzylideneacetone) dipalladium (0) (Pd$_2$(dpa)$_3$), 0.13 g (0.23 mmol) of 1,1'-bis (diphenylphosphino)ferrocene (dppf), and 0.29 g (3.01 mmol) of sodium tert-butoxide were placed into a 50-mL, 3-necked flask, followed by purging the interior of the flask with argon. 2 mL of toluene was added into the flask, and the resulting mixture was stirred at about 100° C. for about 6 hours. Upon completion of the reaction, the reaction mixture was cooled to room temperature, and the impurities were removed by filtration using a Celite. Water was then added to the resulting filtrate, followed by extraction with toluene to obtain an organic phase, and the organic phase was concentrated. The resulting concentrate was purified by column chromatography, thereby obtaining Compound 19.

10.00 g (14.50 mmol) of Compound 19, 4.50 g (15.92 mmol) of 1-bromo-4-iodobenzene, 0.15 g (0.80 mmol) of copper (I) iodide, 0.33 g (2.89 mmol) of trans-1,2-cyclohexanediamine, and 2.78 g (28.04 mmol) of sodium tert-butoxide were placed into a 100-mL, 3-necked flask, followed by purging the interior of the flask with argon. 14 mL of anhydrous 1,4-dioxane was added into the flask, and the resulting mixture was stirred at about 100° C. for about 8 hours. Upon completion of the reaction, the reaction mixture was cooled down to room temperature, impurities were removed by filtration using a Celite, and the resulting filtrate was concentrated. The resulting concentrate was purified by column chromatography, thereby obtaining Compound 20.

Compound 21 was synthesized in the same manner as in the synthesis of Compound 9, except that Compound 20, instead of Compound 8, was used. Monomer F was synthesized in the same manner as in the synthesis of the monomer B, except that Compound 21, instead of Compound 9, was used.

The monomer F was identified by $H^1$-NMR.

$^1$H-NMR (300 MHz, CDCl$_3$): δ 7.71-7.37 (m, 10H), 7.28-7.04 (m, 18H), 6.81 (dd, J=17.4 Hz, 10.8 Hz, 1H), 5.80 (d, J=18.0 Hz, 1H), 5.24 (d, J=11.4 Hz, 1H), 2.35 (s, 9H), 2.01-1.96 (m, 4H), 1.79-1.73 (m, 4H), 1.29-1.05 (m, 40H), 0.88-0.68 (m, 20H).

2) Synthesis of Compound 103

Compound 103 having a structure represented by the following formula was synthesized in the same manner as in the synthesis of Compound 100, except that the monomers E and F, instead of the monomers A and B, were used. Compound 103 had a ratio (Ee:Ff) of subunits Ee from the monomer E to subunits Ff from the monomer F of 90:10. Compound 103 had a number average molecular weight (Mn) of about 38,000 Da, a weight average molecular weight (Mw) of about 93,000 Da, and a polydispersity index (Mw/Mn) of about 2.4.

Next, a 7:3 (by mass ratio) mixture of 1,3-bis(N-carbazolyl)benzene (mCP) and 4,4'-bis(carbazole-9-yl)biphenyl (CBP) as a host and tris(2-(3-p-xylyl)phenyl)pyridine iridium(III) (TEG) as a dopant were co-deposited thereon in a vacuum deposition device to form an emission layer having a thickness of about 30 nm (about 10 percent by weight of the dopant based on a total weight of the emission layer). TEG is a light-emitting material which emits light (phosphorescent light) from triplet excitons.

Subsequently, the ITO glass substrate with the emission layer formed thereon was introduced into a vacuum deposition system, and Liq and KLET-03 were co-deposited on the emission layer to form an electron transport layer having a thickness of about 50 nm.

Subsequently, LiF as an electron injection material was deposited thereon to form an electron injection layer having a thickness of about 1 nm, and then aluminum was deposited on the electron injection layer to form a cathode having a thickness of about 100 nm, thereby completing the manufacture of the organic light-emitting device.

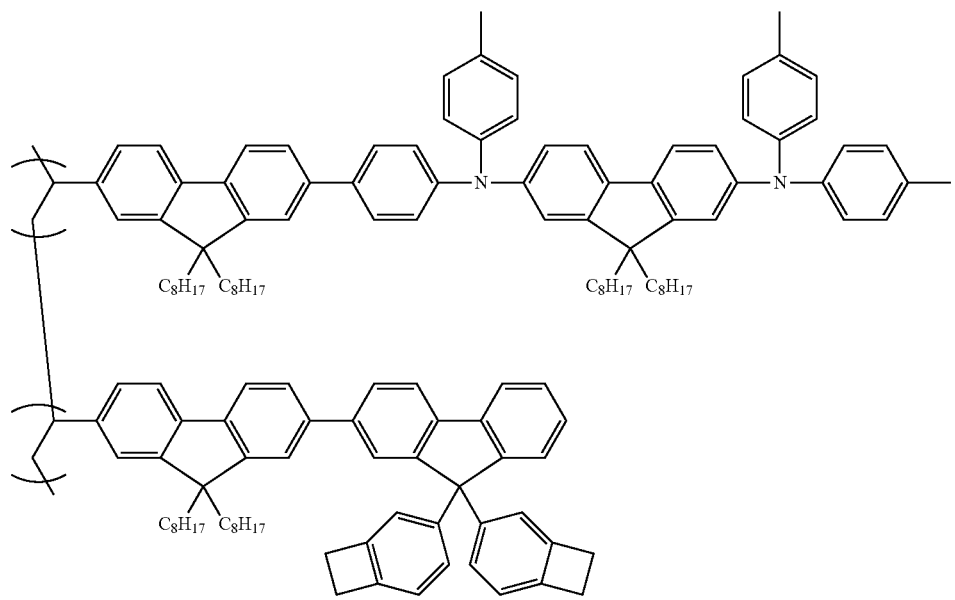

Compound 103

Example 1

An organic light-emitting device as illustrated in FIG. 1 was prepared according to the following method.

PEDOT/PSS (available from Sigma-Aldrich) was spin-coated on an ITO glass substrate with a strip type ITO (having a thickness of about 150 nanometers, nm) anode, and then dried to form a hole injection layer having a thickness of about 30 nm after drying.

Next, Compound 100 (1 percent by weight (wt %), in a xylene solution) was spin-coated on the hole injection layer under nitrogen atmosphere, and thermally treated on a hot plate at about 230° C. for about 1 hour to form a hole transport layer having a thickness of about 30 nm.

Example 2

An organic light-emitting device was manufactured in the same manner as in Example 1, except that Compound 101, instead of Compound 100, was used.

Example 3

An organic light-emitting device was manufactured in the same manner as in Example 1, except that Compound 102, instead of Compound 100, was used.

Example 4

An organic light-emitting device was manufactured in the same manner as in Example 1, except that Compound 103, instead of Compound 100, was used.

Comparative Example 1

An organic light-emitting device was manufactured in the same manner as in Example 1, except that Compound c1, instead of Compound 100, was used. Compound c1 represented by the following formula is a random copolymer including no repeating unit having a fluorene structure, wherein a mole ratio of n to m is 90:10. Compound c1 had a number average molecular weight (Mn) of about 24,000 Da and a weight average molecular weight (Mw) of about 64,000 Da.

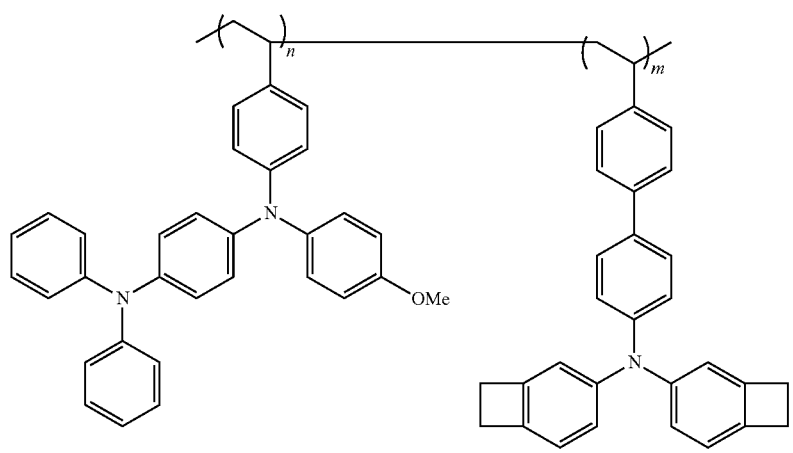

Compound c1

Evaluation Example

Current efficiencies and lifetimes of the organic light-emitting devices of Example 1 to 4 and Comparative Example 1 were evaluated according to the following methods. The results are shown in Table 1. The current efficiencies and lifetimes in Table 1 are relative values with respect to those of the organic light-emitting device of Comparative Example 1, i.e., with the assumption that the current efficiency and emission lifetime of the organic light-emitting device of Comparative Example 1 are both 100.

(1) Current Efficiency

A predetermined voltage was applied to each of the organic light-emitting device with a direct constant-voltage power supply (for example, a source meter available from KEYENCE) to operate the organic light-emitting device. The luminescence from each of the organic light-emitting devices was measured using a luminance meter (for example, SR-3, available from Topcon), while gradually increasing a current applied to the organic light-emitting device until a luminance of about 1,000 candelas per square meter ($cd/m^2$) at which the current was maintained constant. A current density per unit area (amperes per square meter, $A/m^2$) of each of the organic light-emitting devices was calculated, and a luminance ($cd/m^2$) was calculated from the current density ($A/m^2$). A current efficiency refers to a conversion efficiency of current into luminescence energy. A higher current efficiency means that an organic light-emitting device may have higher performance.

(2) Lifetime

The time it took for the luminance of an organic light-emitting device to reach 80% of an initial luminance measured with a luminance meter was evaluated as "lifetime."

TABLE 1

| Example | Hole transport layer | Current efficiency | Lifetime |
|---|---|---|---|
| Example 1 | Compound 100 | 120 | 1,630 |
| Example 2 | Compound 101 | 112 | 540 |
| Example 3 | Compound 102 | 118 | 2,000 |
| Example 4 | Compound 103 | 110 | 910 |
| Comparative Example 1 | Compound c1 | 100 | 100 |

Referring to Table 1, the organic light-emitting devices of Examples 1 to 4 were found to have improved current efficiency and improved emission lifetime.

An amino fluorene polymer according to any of the above-described embodiments may ensure efficient formation of layers by a liquid coating method, and may also improve lifetime of an organic light-emitting device.

As described above, an organic light-emitting device including an amino fluorene polymer according to any of the above-described embodiments may have improved emission lifetime and improved current efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present disclosure as defined by the following claims.

What is claimed is:

1. An amino fluorene polymer comprising at least two first repeating units represented by Formula 1:

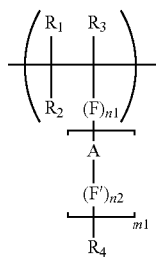

Formula 1 wherein, in Formula 1, $R_1$ to $R_3$ are each independently selected from a hydrogen atom, a substituted or unsubstituted $C_1$-$C_{10}$ alkyl group, and a substituted or unsubstituted $C_6$-$C_{30}$ aryl group;

m1 is an integer from 1 to 20;

F and F' are each independently selected from a substituted or unsubstituted azafluorenylene group and a substituted or unsubstituted fluorenylene group;

n1 and n2 are each independently selected from 1 and 2;

A is a group represented by Formula 2;

$R_4$ is selected from a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$);

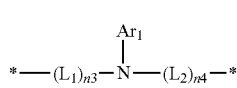

Formula 2 wherein, in Formula 2, $L_1$ and $L_2$ are each independently selected from a single bond, a substituted or unsubstituted $C_1$-$C_{20}$ alkylene group, a substituted or unsubstituted $C_3$-$C_{16}$ cycloalkylene group, a substituted or unsubstituted $C_6$-$C_{30}$ arylene group, a substituted or unsubstituted $C_1$-$C_{20}$ oxyalkylene group, a substituted or unsubstituted $C_3$-$C_{16}$ oxycycloalkylene group, a substituted or unsubstituted $C_6$-$C_{30}$ oxyarylene group, a substituted or unsubstituted $C_7$-$C_{40}$ aralkylene group, a substituted or unsubstituted $C_5$-$C_{30}$ heteroarylene group, —Si($Q_4$)($Q_5$)-, and —N($Q_4$)-;

n3 and n4 are each independently selected from 1 and 2;

$Ar_1$ is selected from a hydrogen atom, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, and —N($Q_6$)($Q_7$);

wherein, $Ar_1$ optionally binds to F, F', $L_1$, or $L_2$ to form a ring;

$Q_1$ to $Q_7$ are each independently selected from a hydrogen atom, a substituted or unsubstituted $C_1$-$C_{20}$ alkyl group, and a substituted or unsubstituted $C_6$-$C_{30}$ aryl group; and

* is a binding site to an adjacent atom.

2. The amino fluorene polymer of claim 1, wherein $R_1$ to $R_3$ are each independently selected from a hydrogen atom, a methyl group, an ethyl group, an n-propyl group, and an n-butyl group.

3. The amino fluorene polymer of claim 1, wherein F and F' are each independently a group represented by Formula 3:

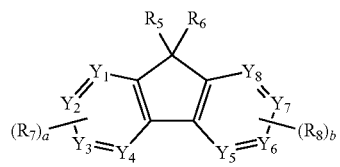

Formula 3 wherein, in Formula 3, $R_5$ to $R_8$ are each independently selected from a binding site, a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$);

wherein, adjacent groups selected from $R_5$ to $R_8$ are optionally linked to one another to form a ring;

two groups selected from $R_5$ to $R_8$ are binding sites to adjacent atoms;

$Q_1$ to $Q_3$ are each independently selected from a hydrogen atom, a substituted or unsubstituted $C_1$-$C_{20}$ alkyl group, and a substituted or unsubstituted $C_6$-$C_{30}$ aryl group;

a and b are each independently selected from 1, 2, 3, and 4; and $Y_1$ to $Y_8$ are each independently a carbon atom or a nitrogen atom.

4. The amino fluorene polymer of claim 3, wherein $R_5$ to $R_8$ are each independently selected from a single bond representing a binding site, hydrogen atom, a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethylpropyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethyl hexyl group, a 3-methyl-1-isopropyl butyl group, a 2-methyl-1-isopropyl group, a 1-tert-butyl-2-methyl propyl group, an n-nonyl group, a 3,5,5-trimethyl hexyl group, an n-decyl group, an iso-decyl group, an n-undecyl group, a 1-methyl decyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, a phenyl group, a naphthyl group, an anthracenyl group, a phenanthrenyl group, a pyridyl group, a pyrimidyl group, a pyrazinyl group, a triazinyl group, a furanyl group, and a thiophenyl group;

a methyl group, an ethyl group, and an n-propyl group, each substituted with at least one selected from —F, a phenyl group, and a naphthyl group;

a phenyl group, a naphthyl group, an anthracenyl group, a phenanthrenyl group, a pyridyl group, a pyrimidyl group, a pyrazinyl group, a triazinyl group, a furanyl group, and a thiophenyl group, each substituted with at least one selected from a methyl group, an ethyl group, an n-propyl group, an iso-propyl group, an n-butyl group, an isobutyl group, a sec-butyl group, a tert-butyl group, an n-octyl group, a phenyl group, a naphthyl group, a phenyl group substituted with a methyl group, and a phenyl group substituted with a tert-butyl group;

wherein, adjacent groups selected from $R_5$ to $R_8$ are optionally linked to one another to form a ring; and wherein two groups selected from $R_5$ to $R_8$ are binding sites to adjacent atoms.

5. The amino fluorene polymer of claim 1, wherein F and F' are each independently selected from groups represented by Formulae 4-1 to 4-58:

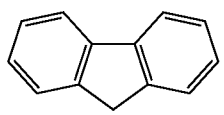
4-1

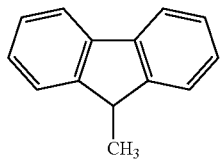
4-2

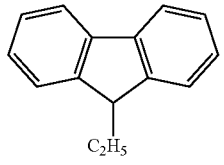
4-3

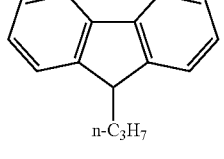
4-4

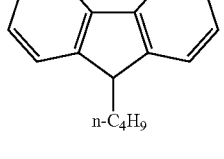
4-5

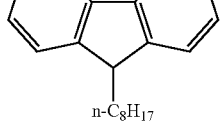
4-6

-continued

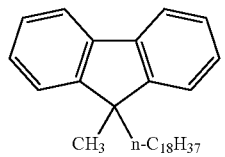
4-7

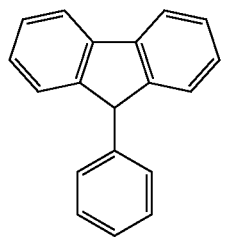
4-8

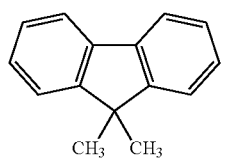
4-9

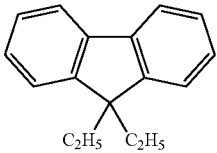
4-10

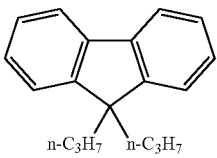
4-11

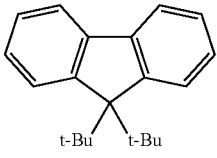
4-12

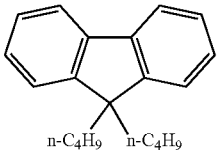
4-13

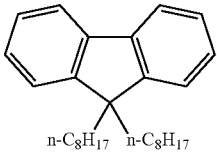
4-14

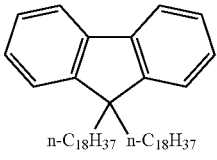
4-15

| | |
|---|---|
| 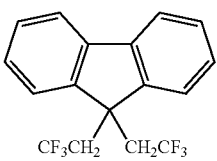 | 4-16 |
| 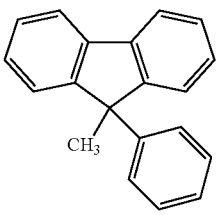 | 4-17 |
| 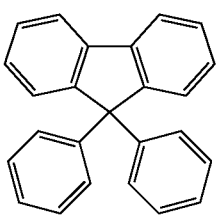 | 4-18 |
| 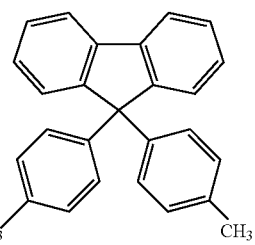 | 4-19 |
| 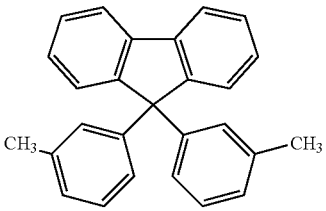 | 4-20 |
| 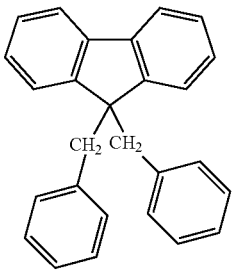 | 4-21 |
| 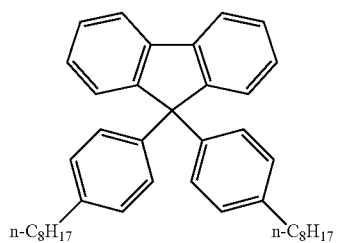 | 4-22 |
| 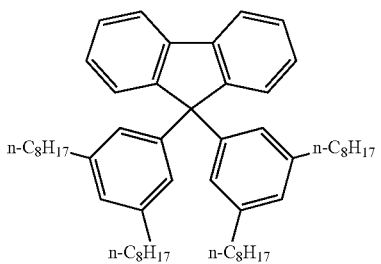 | 4-23 |
| 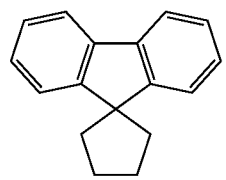 | 4-24 |
| 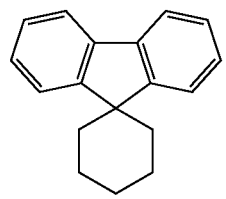 | 4-25 |
| 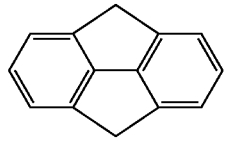 | 4-26 |
| 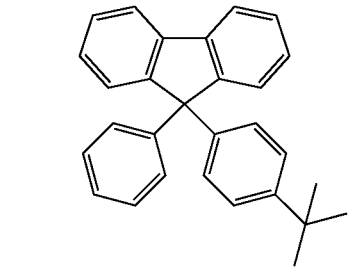 | 4-27 |
| 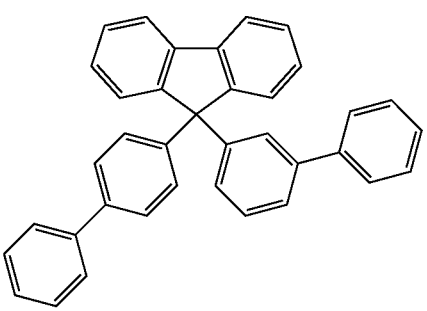 | 4-28 |

4-29
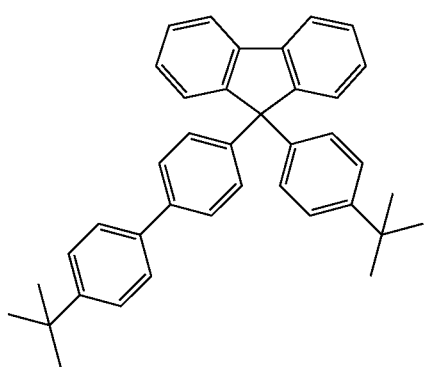
4-30
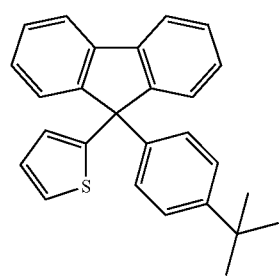
4-31
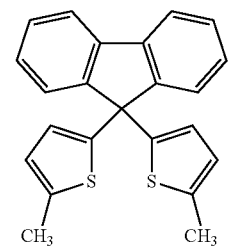
4-32
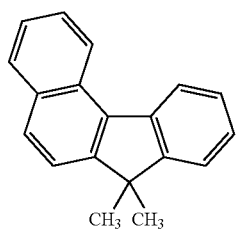
4-33
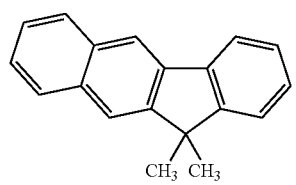
4-34
4-35
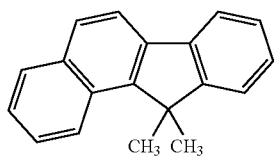
4-36
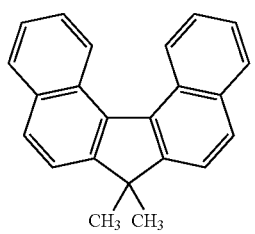
4-37
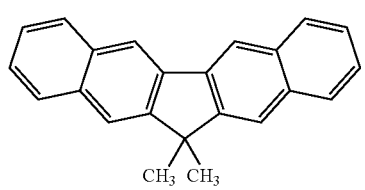
4-38
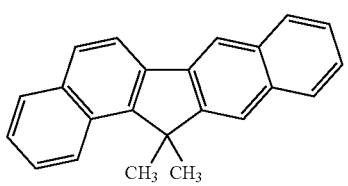
4-39
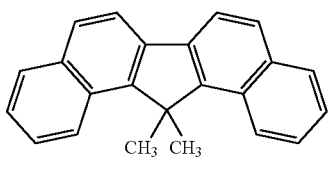
4-40
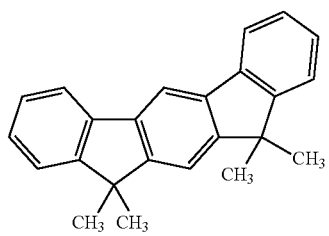
4-41
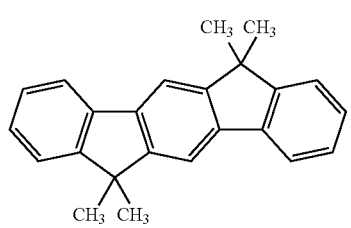

-continued
4-42
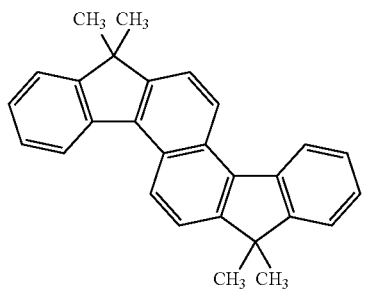
4-43
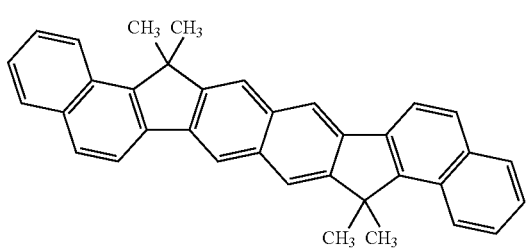
4-44
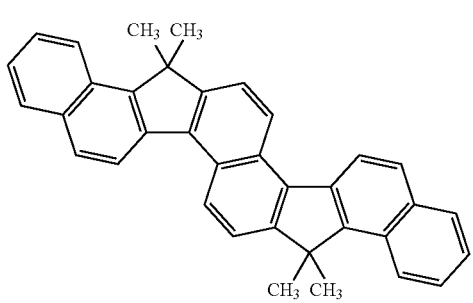
4-45
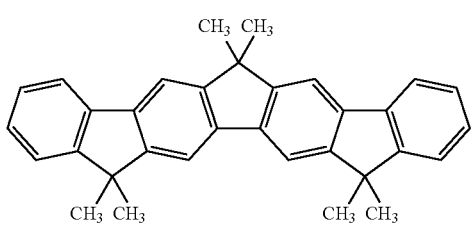
4-46
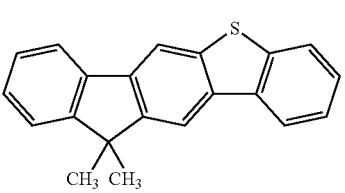
4-47
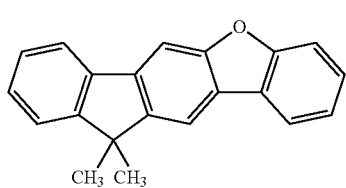
-continued
4-48
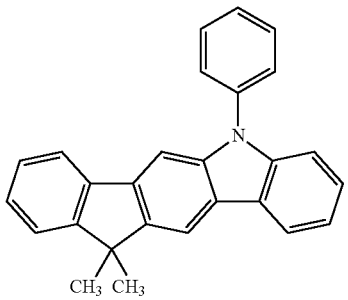
4-49
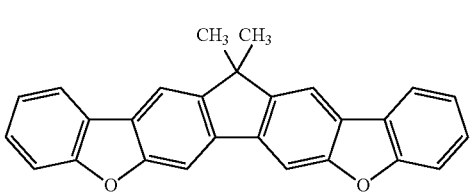
4-50
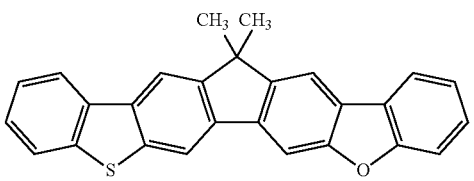
4-51
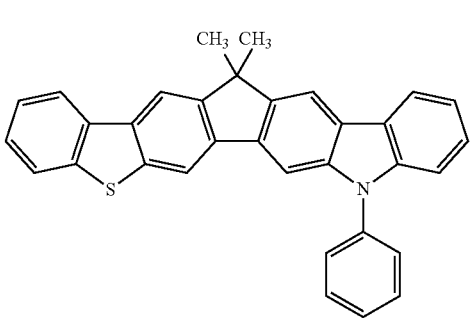
4-52
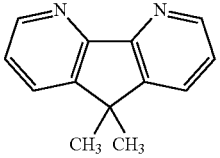
4-53
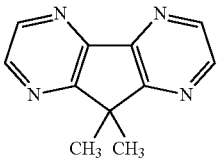
4-54
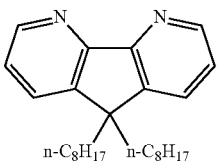

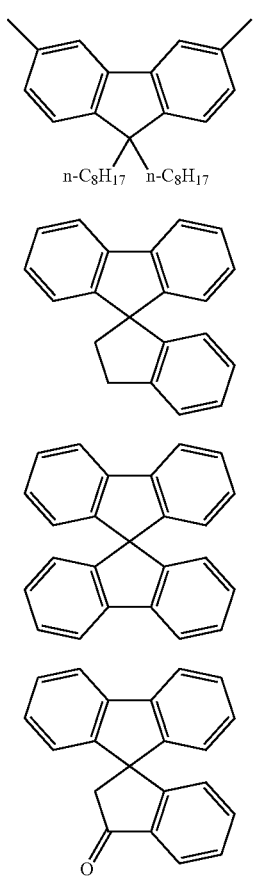

wherein, in Formulae 4-1 to 4-58, any two hydrogen atoms are replaced by binding sites to adjacent atoms.

6. The amino fluorene polymer of claim 1, wherein $R_4$ is selected from
a hydrogen atom, a $C_1$-$C_{20}$ alkyl group, a $C_6$-$C_{30}$ aryl group, a $C_1$-$C_{20}$ alkoxy group, and —$N(Q_1)(Q_2)$; and
a $C_6$-$C_{30}$ aryl group substituted with at least one selected from a $C_1$-$C_{20}$ alkyl group, a $C_6$-$C_{30}$ aryl group, and a $C_1$-$C_{20}$ alkoxy group; and
$Q_1$ and $Q_2$ are each independently selected from a hydrogen atom, a $C_6$-$C_{30}$ aryl group; and
a $C_6$-$C_{30}$ aryl group substituted with $C_1$-$C_{20}$ alkyl group.

7. The amino fluorene polymer of claim 1, wherein $R_4$ is selected from a hydrogen atom, a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethyl hexyl group, a 3-methyl-1-isopropyl butyl group, a 2-methyl-1-iso-propyl group, a 1-tert-butyl-2-methyl propyl group, a phenyl group, a naphthyl group, an anthracenyl group, a phenanthrenyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, an n-octyloxy group, and —$N(Q_1)(Q_2)$, and
a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a phenyl group, a naphthyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, and an n-octyloxy group; and
$Q_1$ and $Q_2$ are each independently selected from
a hydrogen atom, a phenyl group, a naphthyl group, an anthracenyl group, and a phenanthrenyl group, and
a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, and a tert-butyl group.

8. The amino fluorene polymer of claim 1, wherein $L_1$ and $L_2$ are each independently selected from
a single bond, a $C_1$-$C_{20}$ alkylene group, and a $C_6$-$C_{30}$ arylene group, and
a $C_1$-$C_{20}$ alkylene group and a $C_6$-$C_{30}$ arylene group, each substituted with at least one selected from a $C_1$-$C_{20}$ alkyl group and a $C_6$-$C_{30}$ aryl group.

9. The amino fluorene polymer of claim 1, wherein $L_1$ and $L_2$ are each independently selected from
a single bond, a methylene group, and a phenylene group, and
a methylene group and a phenylene group, each substituted with at least one selected from a methyl group, an n-hexyl group, and a phenyl group.

10. The amino fluorene polymer of claim 1, wherein $Ar_1$ is selected from
a hydrogen atom, a $C_1$-$C_{20}$ alkyl group, and a $C_6$-$C_{30}$ aryl group, and
a $C_6$-$C_{30}$ aryl group substituted with at least one selected from a $C_1$-$C_{20}$ alkyl group, a $C_6$-$C_{30}$ aryl group, and a $C_1$-$C_{20}$ alkoxy group, wherein, An optionally binds to F, F', $L_1$, or $L_2$ to form a ring.

11. The amino fluorene polymer of claim 1, wherein $Ar_1$ is selected from
a hydrogen atom, a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl-butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethyl hexyl group, a 3-methyl-1-isopropyl butyl group, a 2-methyl-1-iso-propyl group, a 1-tert-butyl-2-methyl-propyl group, a phenyl group, a naphthyl group, an anthracenyl group, and a phenanthrenyl group, and a phenyl group, a naphthyl group, an anthracenyl group, and a phenanthrenyl group, each substituted with at least one selected from a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethyl propyl group, an n-hexyl group, an iso-hexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a phenyl group, a naphthyl group, a methoxy group, an ethoxy group, an n-propoxy group, an iso-propoxy group, an n-butoxy group, a tert-butoxy group, an n-pentyloxy group, an n-hexyloxy group, an n-heptyloxy group, and an n-octyloxy group, and wherein, $Ar_1$ optionally binds to F, F', $L_1$, or $L_2$ to form a ring.

12. The amino fluorene polymer of claim 1, wherein the first repeating units of Formula 1 are represented by Formula 1-1:

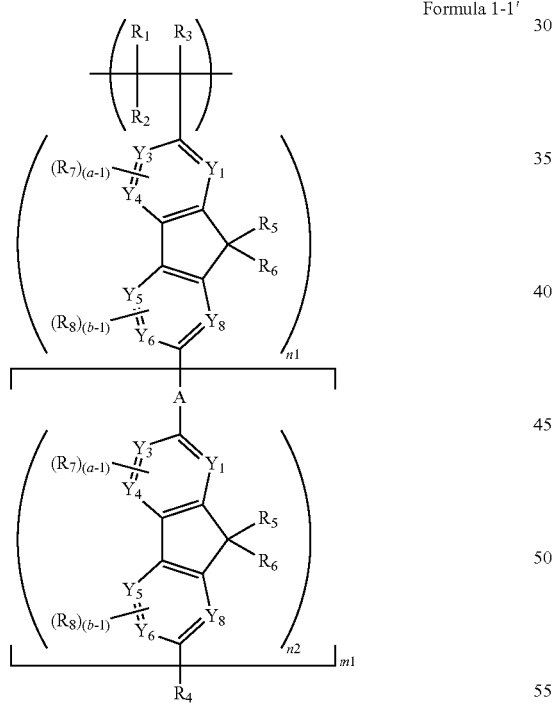

Formula 1-1' wherein, in Formula 1-1,
$R_1$ to $R_3$ are each independently selected from a hydrogen atom, a substituted or unsubstituted $C_1$-$C_{10}$ alkyl group, and a substituted or unsubstituted $C_6$-$C_{30}$ aryl group;
m1 is an integer from 1 to 20;
F and F' are each independently selected from a substituted or unsubstituted azafluorenylene group and a substituted or unsubstituted fluorenylene group;
n1 and n2 are each independently selected from 1 and 2;
A is a group represented by Formula 2; and $R_4$ is selected from a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$):

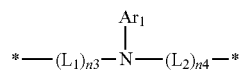

Formula 2 wherein, in Formula 2,
$L_1$ and $L_2$ are each independently selected from a single bond, a substituted or unsubstituted $C_1$-$C_{20}$ alkylene group, a substituted or unsubstituted $C_3$-$C_{16}$ cycloalkylene group, a substituted or unsubstituted $C_6$-$C_{30}$ arylene group, a substituted or unsubstituted $C_1$-$C_{20}$ oxyalkylene group, a substituted or unsubstituted $C_3$-$C_{16}$ oxycycloalkylene group, a substituted or unsubstituted $C_6$-$C_{30}$ oxyarylene group, a substituted or unsubstituted $C_7$-$C_{40}$ aralkylene group, a substituted or unsubstituted $C_5$-$C_{30}$ heteroarylene group, —Si($Q_4$)($Q_5$)-, and —N($Q_4$)-;
n3 and n4 are each independently selected from 1 and 2;
$Ar_1$ is selected from a hydrogen atom, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, and —N($Q_6$)($Q_7$);
wherein, $Ar_1$ optionally binds to F, F', $L_1$, or $L_2$ to form a ring;
* is a binding site to an adjacent atom;
$R_5$ to $R_8$ are each independently selected from a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$);
wherein, adjacent groups selected from $R_5$ to $R_8$ are optionally linked to one another to form a ring;
a and b are each independently selected from 1, 2, 3, and 4;
$Y_1$ to $Y_8$ are each independently a carbon atom or a nitrogen atom; and
$Q_1$ to $Q_7$ are each independently selected from a hydrogen atom, a substituted or unsubstituted $C_1$-$C_{20}$ alkyl group, and a substituted or unsubstituted $C_6$-$C_{30}$ aryl group.

13. The amino fluorene polymer of claim 1, wherein the first repeating units of Formula 1 are selected from units represented by the following formulae:

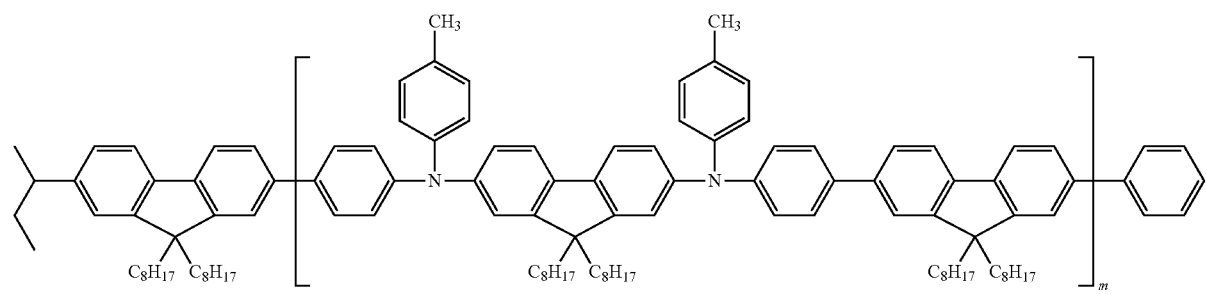
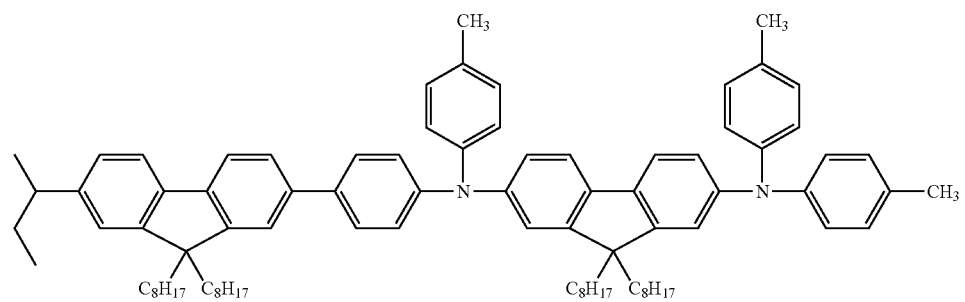
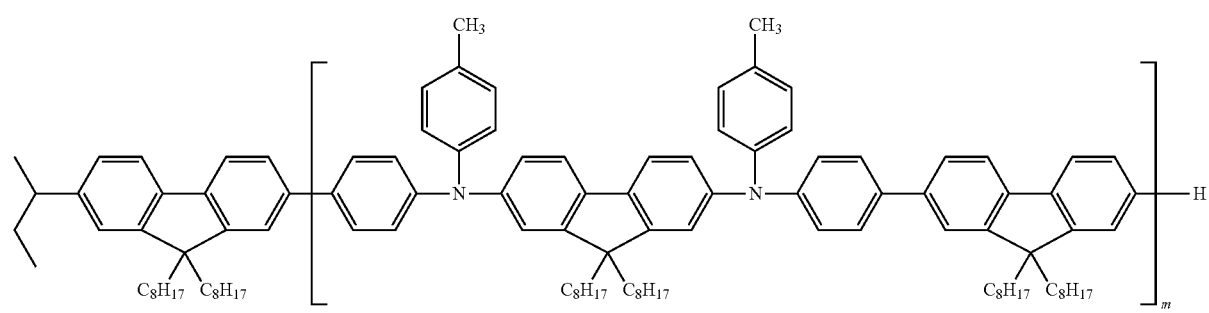
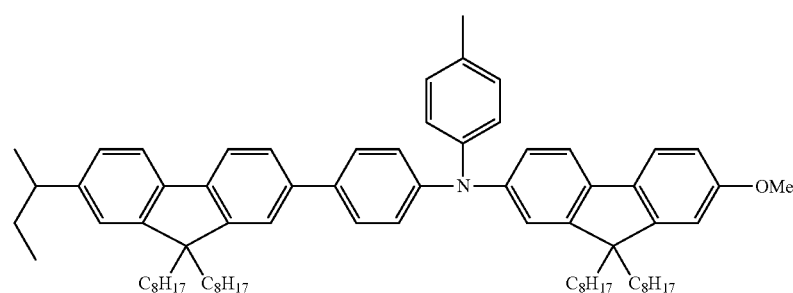
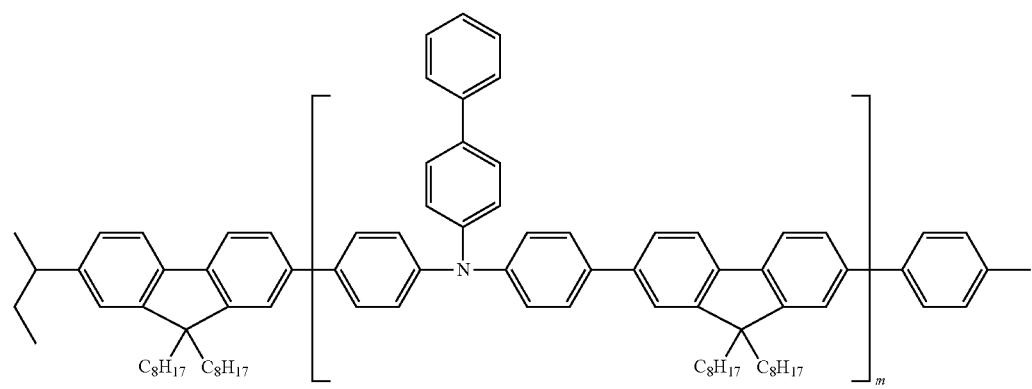

-continued
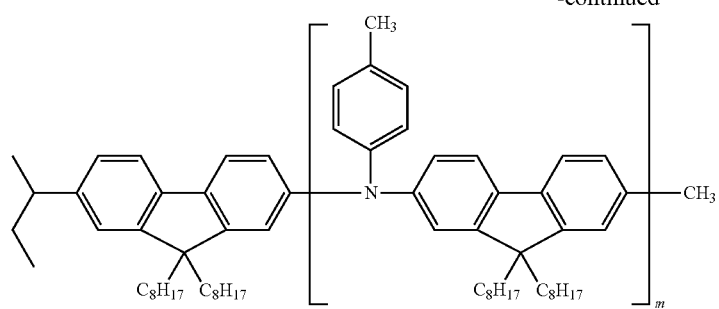
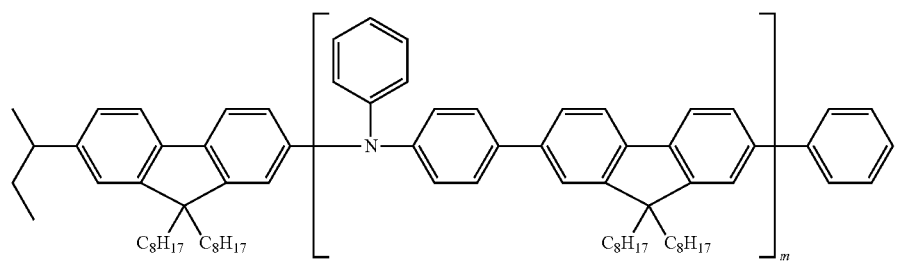
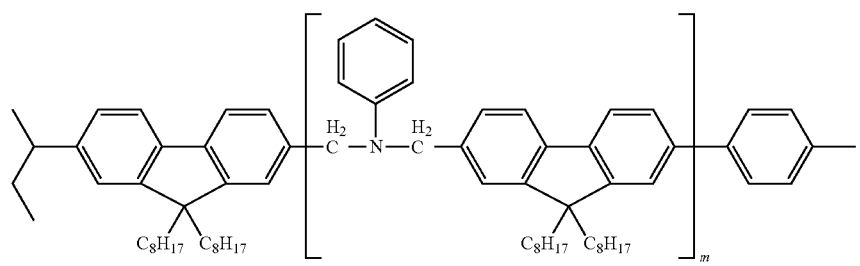
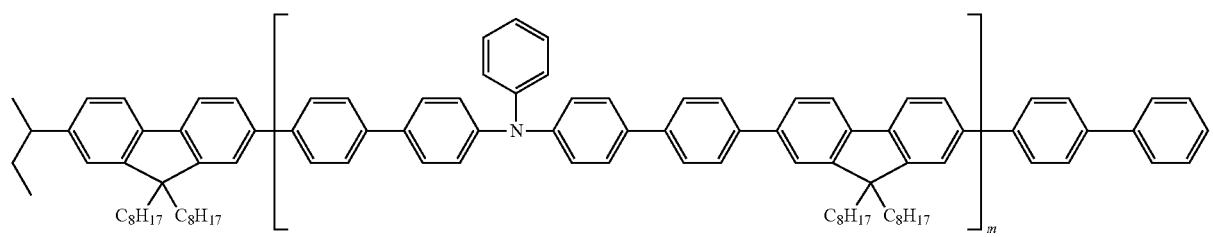
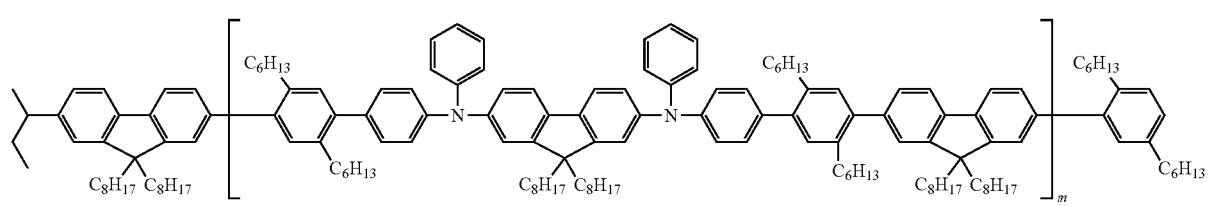
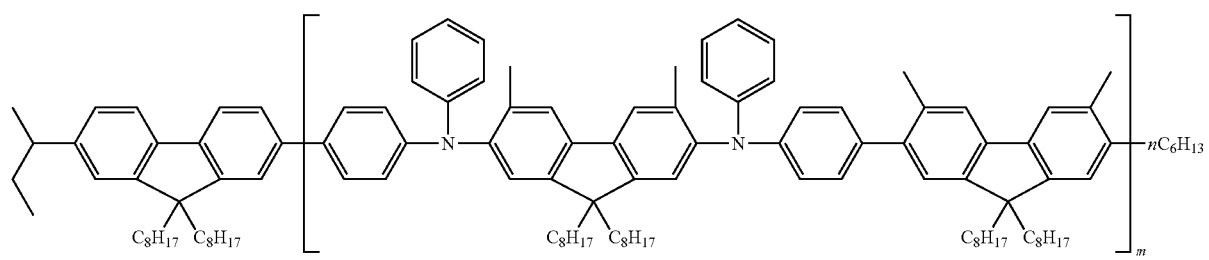

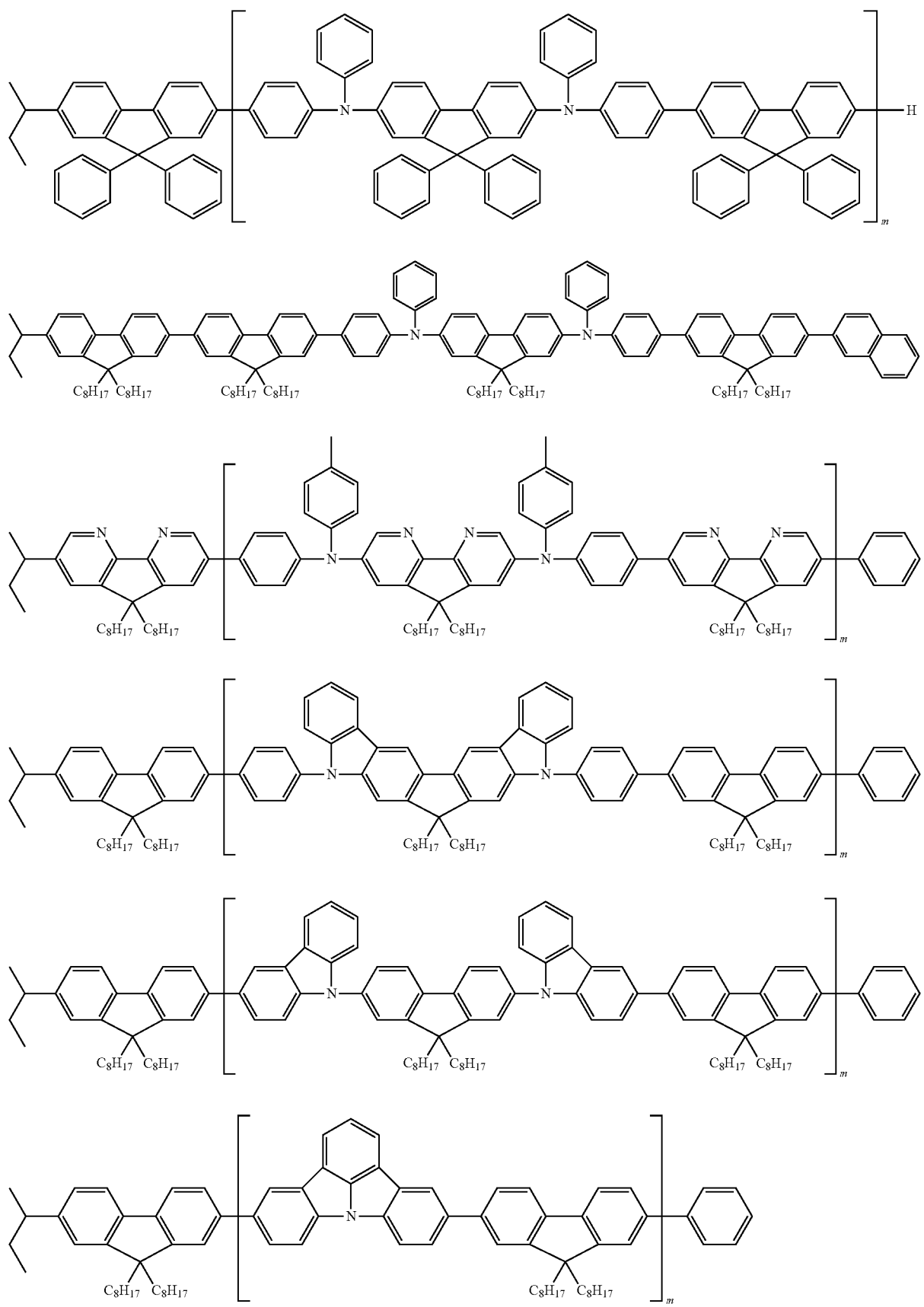

-continued
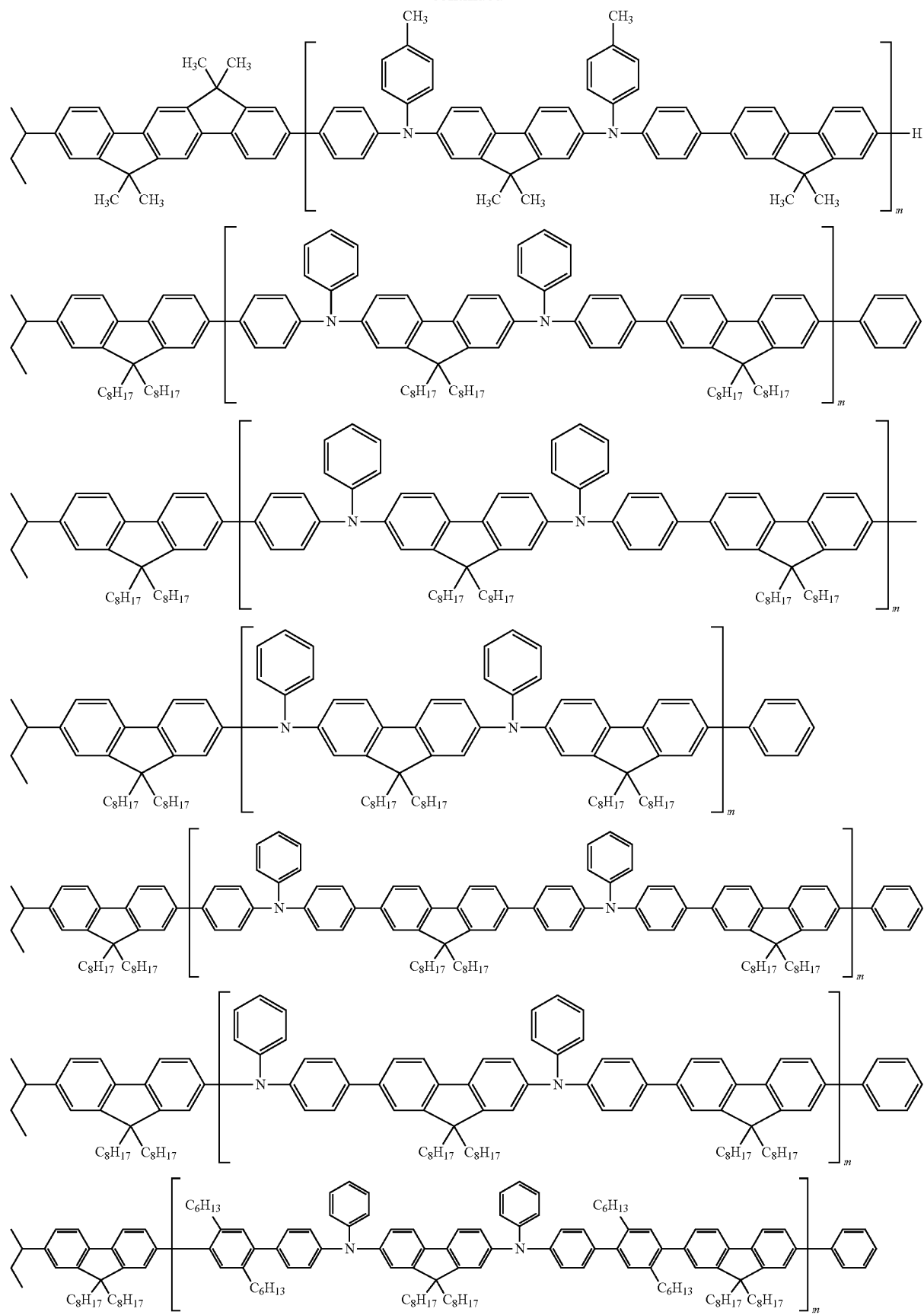

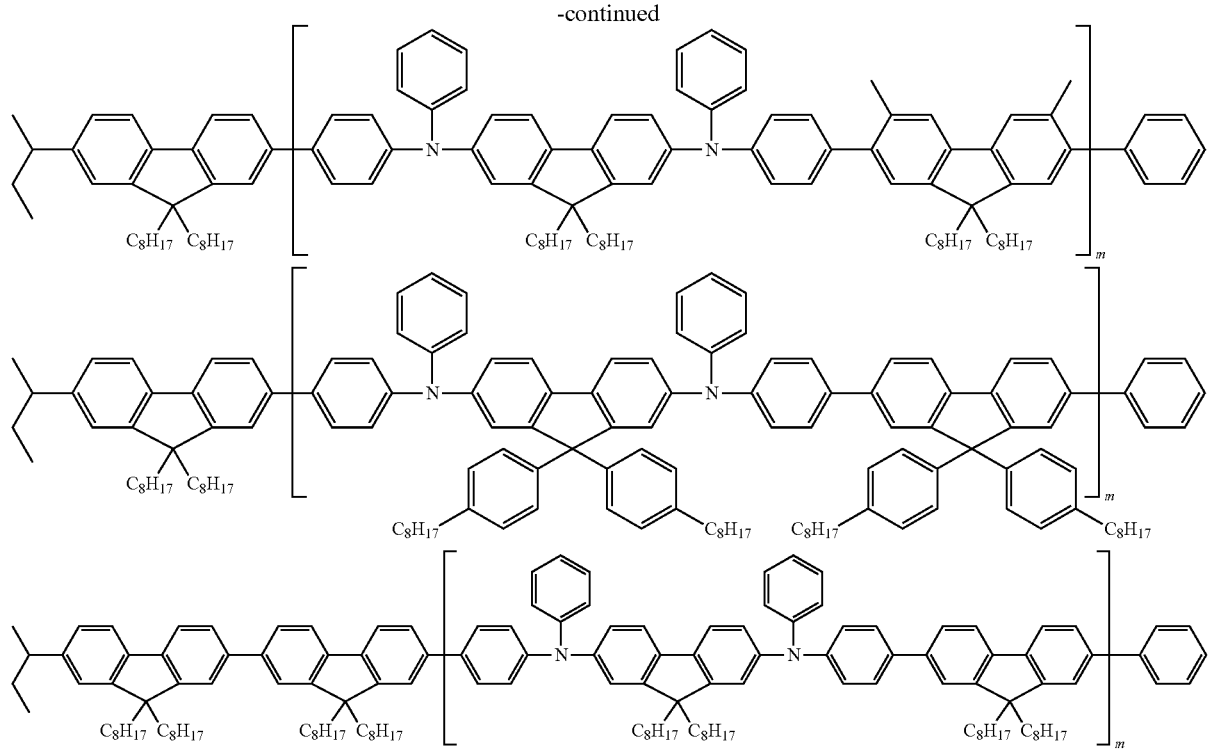

wherein m is an integer from 1 to 10.

14. The amino fluorene polymer of claim 1, wherein the amino fluorene polymer further comprises a second repeating unit derived from a monomer comprising at least one selected from cross-linking groups represented by Formulae 5-1 to 5-10:

5-1
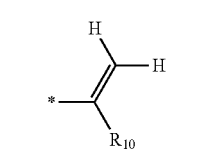

5-2
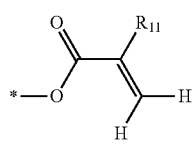

5-3
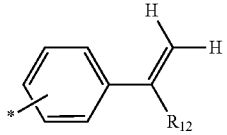

5-4
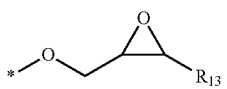

5-5
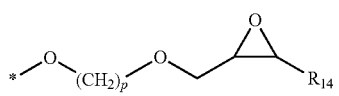

5-6
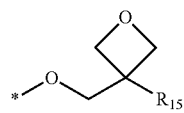

5-7
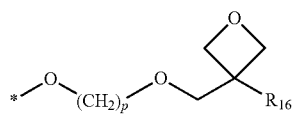

5-8
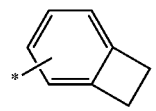

5-9
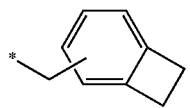

5-10
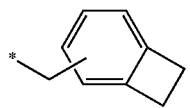

wherein, in Formulae 5-1 to 5-10, $R_{10}$ to $R_{16}$ are each independently a hydrogen atom, or a substituted or unsubstituted $C_1$-$C_{20}$ alkyl group;

p is an integer from 1 to 10; and

* is a binding site to an adjacent atom.

15. The amino fluorene polymer of claim 14, wherein the second repeating unit is represented by Formula 6:

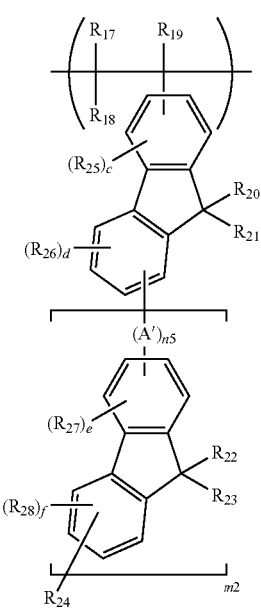

Formula 6

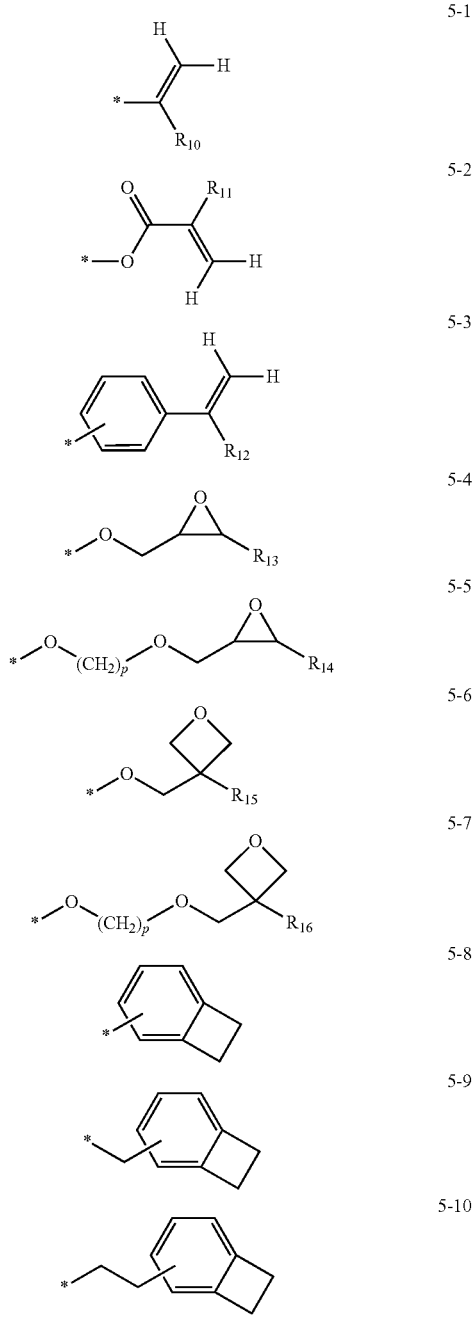

wherein, in Formula 6, $R_{17}$ to $R_{19}$ are each independently a hydrogen atom, a substituted or unsubstituted $C_1$-$C_{10}$ alkyl group, or a substituted or unsubstituted $C_6$-$C_{30}$ aryl group;

$R_{20}$ to $R_{28}$ are each independently selected from cross-linking groups represented by Formulae 5-1 to 5-10, a hydrogen atom, a halogen atom, a hydroxyl group, a nitro group, a cyano group, a substituted or unsubstituted $C_1$-$C_{20}$ alkyl group, a substituted or unsubstituted $C_3$-$C_{16}$ cycloalkyl group, a substituted or unsubstituted $C_6$-$C_{30}$ aryl group, a substituted or unsubstituted $C_1$-$C_{20}$ alkoxy group, a substituted or unsubstituted $C_3$-$C_{16}$ cycloalkoxy group, a substituted or unsubstituted $C_6$-$C_{30}$ aryloxy group, a substituted or unsubstituted $C_7$-$C_{40}$ aralkyl group, a substituted or unsubstituted $C_5$-$C_{30}$ heteroaryl group, —Si($Q_1$)($Q_2$)($Q_3$), and —N($Q_1$)($Q_2$);

wherein, adjacent groups of $R_{20}$ to $R_{28}$ are optionally linked to one another to form a ring;

at least one group of $R_{20}$ to $R_{28}$ is selected from cross-linking groups represented by Formulae 5-1 to 5-10;

c, d, e, and f are each independently selected from 1, 2, and 3;

A' is selected from a single bond, a substituted or unsubstituted $C_1$-$C_{20}$ alkylene group, a substituted or unsubstituted $C_3$-$C_{16}$ cycloalkylene group, a substituted or unsubstituted $C_6$-$C_{30}$ arylene group, a substituted or unsubstituted $C_1$-$C_{20}$ oxyalkylene group, a substituted or unsubstituted $C_3$-$C_{16}$ oxycycloalkylene group, a substituted or unsubstituted $C_6$-$C_{30}$ oxyarylene group, a substituted or unsubstituted $C_7$-$C_{40}$ aralkylene group, a substituted or unsubstituted $C_5$-$C_{30}$ heteroarylene group, —Si($Q_4$)($Q_5$)-, and —N($Q_4$)-;

n5 is selected from 1, 2, 3, 4, and 5;

m2 is an integer from 0 to 20; and $Q_1$ to $Q_5$ are each independently selected from a hydrogen atom, a substituted or unsubstituted $C_1$-$C_{20}$ alkyl group, and a substituted or unsubstituted $C_6$-$C_{30}$ aryl group;

wherein, in Formulae 5-1 to 5-10, $R_{10}$ to $R_{16}$ are each independently a hydrogen atom or a substituted or unsubstituted $C_1$-$C_{20}$ alkyl group;

p is an integer from 1 to 10; and

* is a binding site to an adjacent atom.

16. The amino fluorene polymer of claim 15, wherein (A')$_{n5}$ is selected from a single bond, a $C_1$-$C_{20}$ alkylene group, a $C_6$-$C_{30}$ arylene group, and a group represented by Formula 2, and a $C_1$-$C_{20}$ alkylene group and a $C_6$-$C_{30}$ arylene group, each substituted with at least one selected from a $C_1$-$C_{20}$ alkyl group and a $C_6$-$C_{30}$ aryl group:

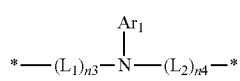

Formula 2 wherein, in Formula 2, $L_1$ and $L_2$ are each independently selected from a single bond, a $C_1$-$C_{20}$ alkylene group, and a $C_6$-$C_{30}$ arylene group, and a $C_1$-$C_{20}$ alkylene group and a $C_6$-$C_{30}$ arylene group, each substituted with at least one selected from a $C_1$-$C_{20}$ alkyl group and a $C_6$-$C_{30}$ aryl group;

n3 and n4 are each independently selected from 1 and 2;

$Ar_1$ is selected from a hydrogen atom, a $C_1$-$C_{20}$ alkyl group, and a $C_6$-$C_{30}$ aryl group, and a $C_6$-$C_{30}$ aryl group substituted with at least one selected from a $C_1$-$C_{20}$ alkyl group, a $C_6$-$C_{30}$ aryl group, and a $C_1$-$C_{20}$ alkoxy group; and \* is a binding site to an adjacent atom.

17. The amino fluorene polymer of claim 14, wherein the second repeating unit is selected from units represented by the following formulae:

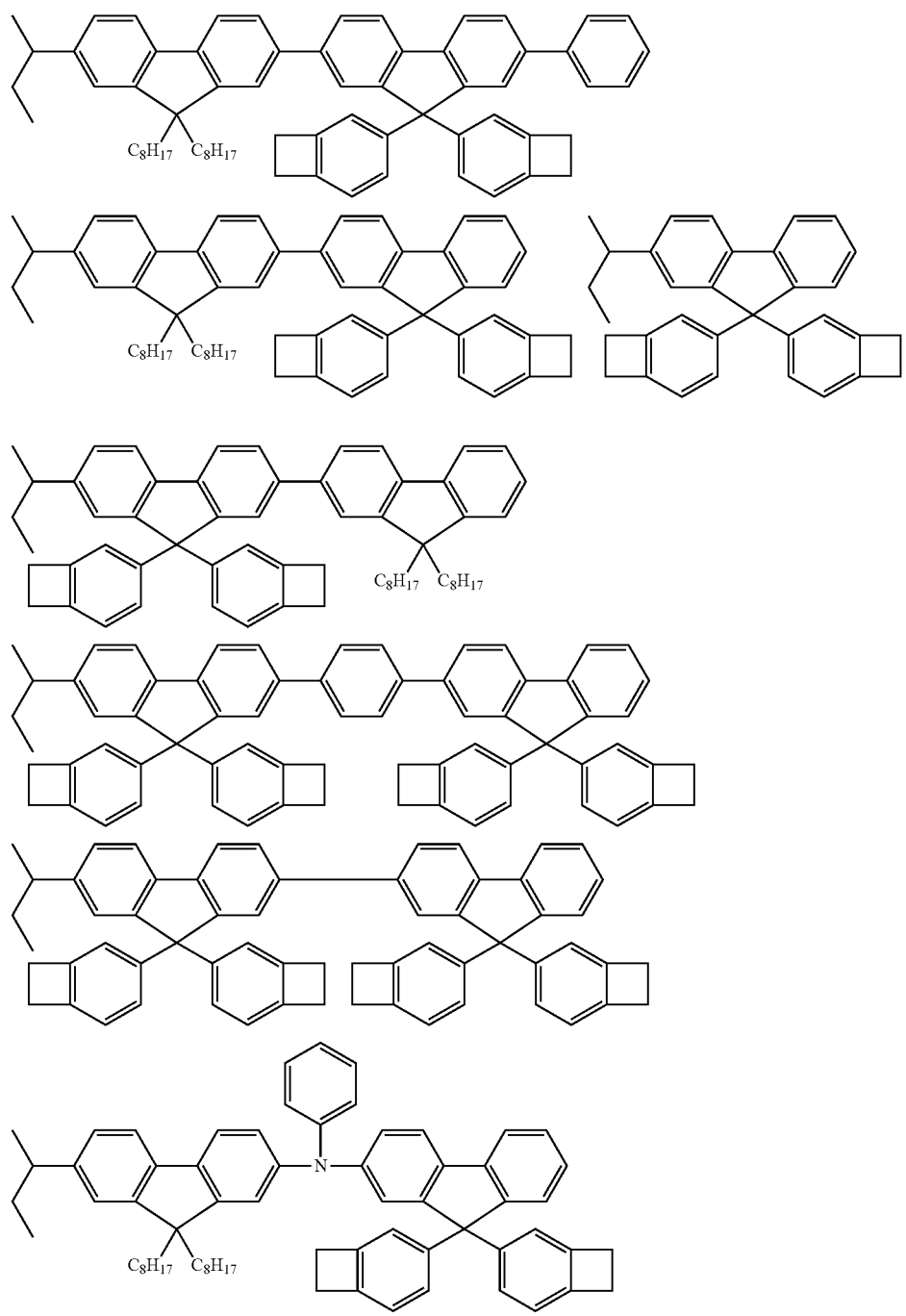

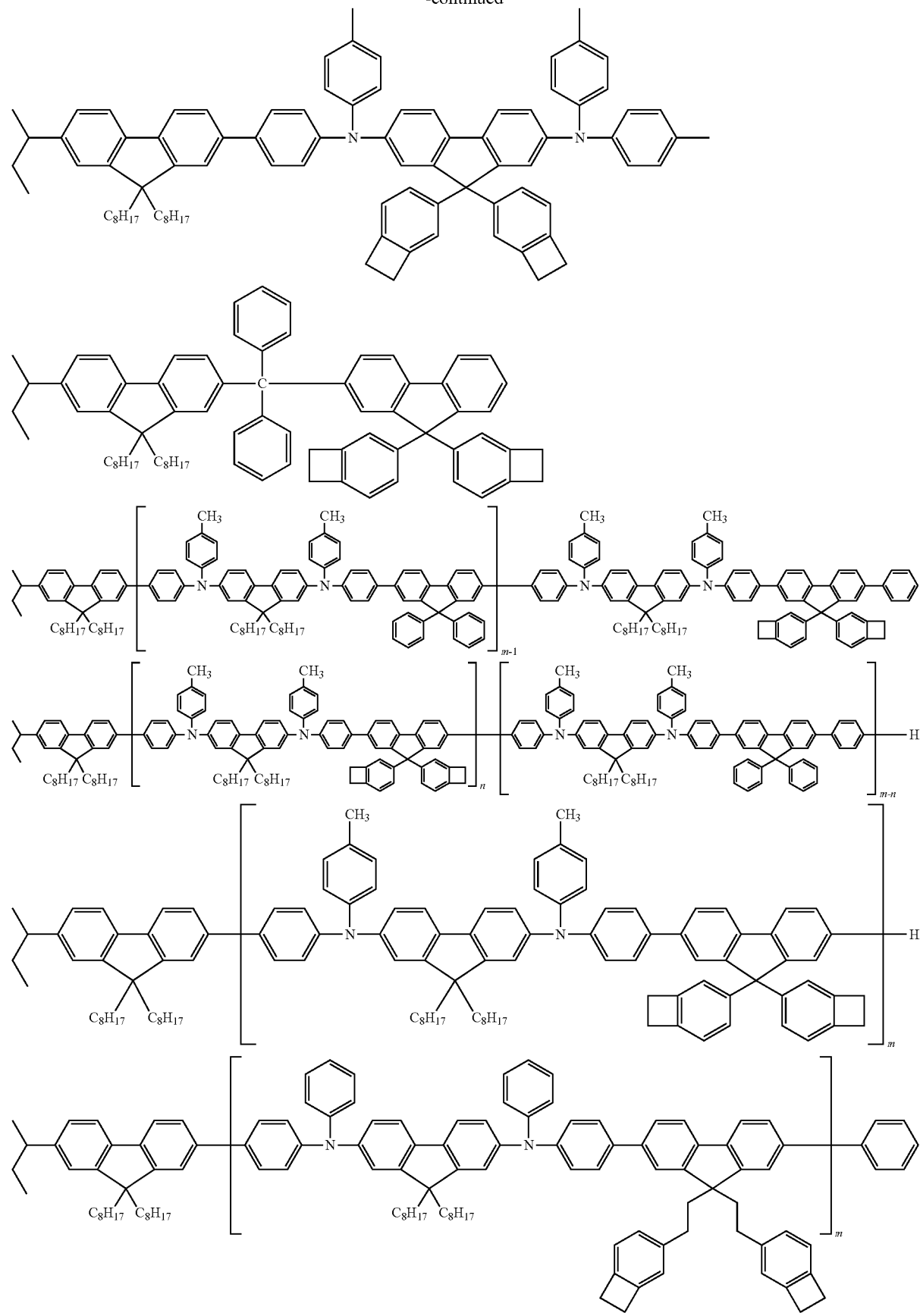

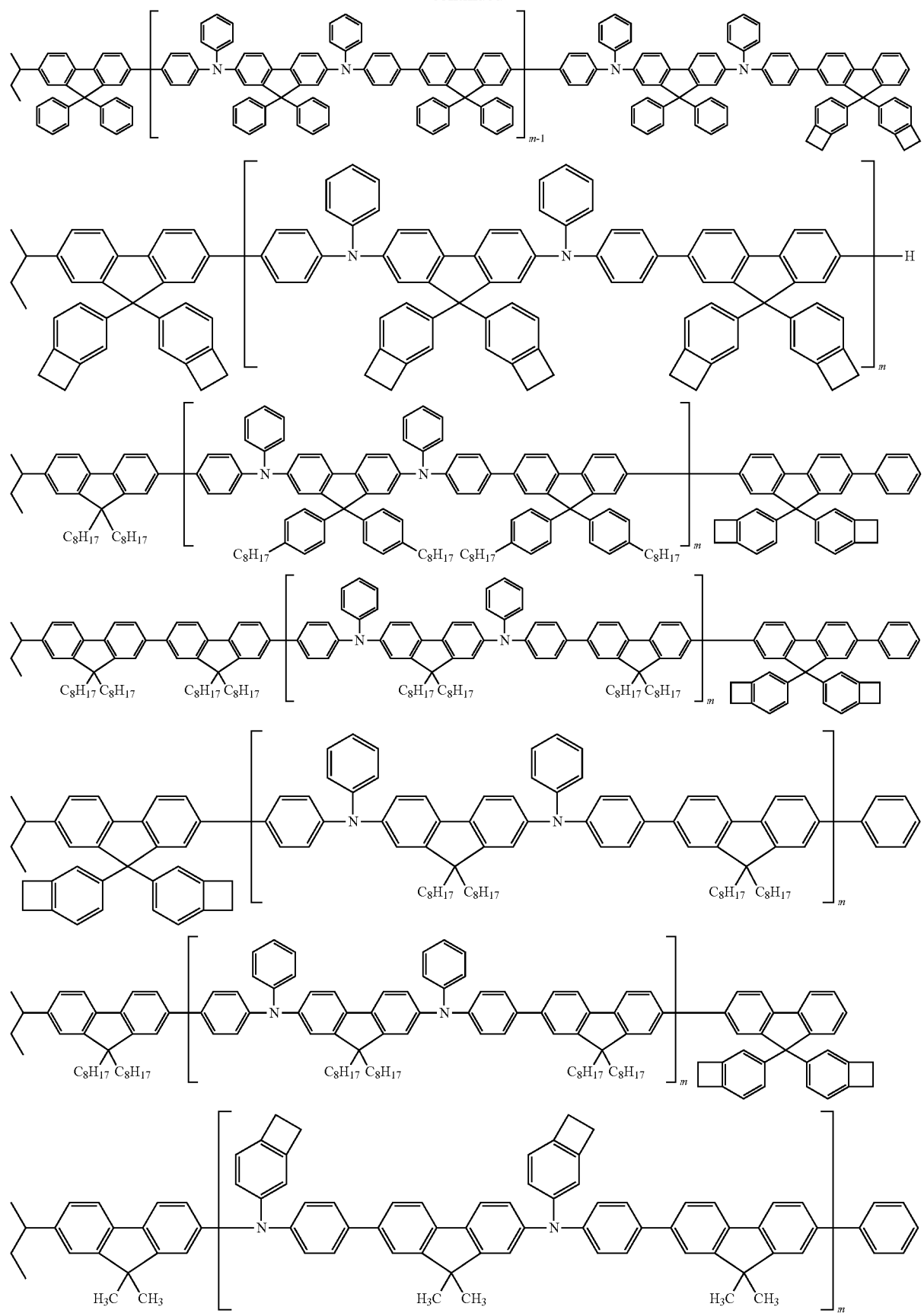

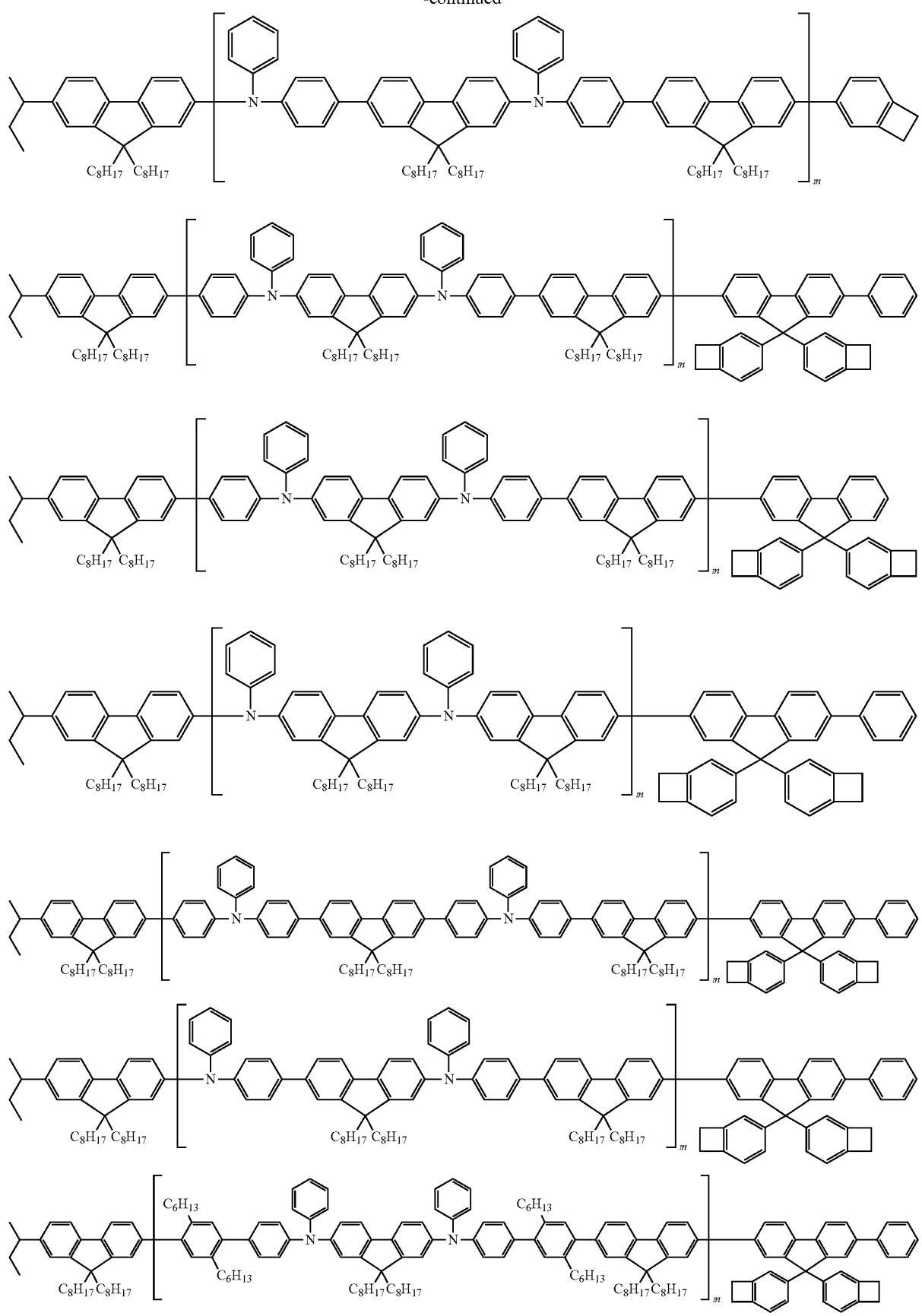

-continued

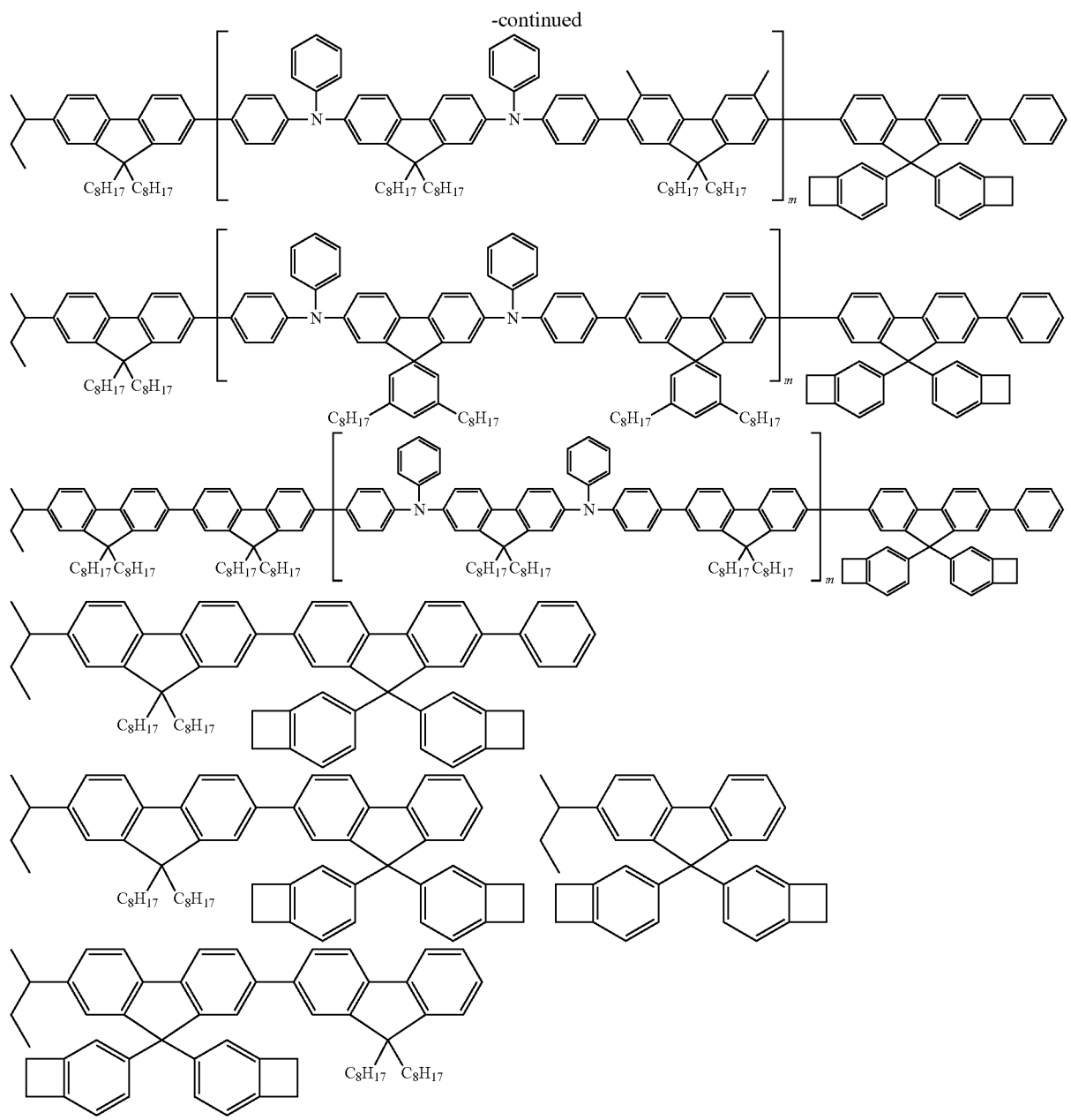

wherein, n and m are each independently an integer from 1 to 10.

18. An organic light-emitting device comprising:
a first electrode;
a second electrode; and
an organic layer disposed between the first electrode and the second electrode,
wherein the organic layer comprises an amino fluorene polymer according to claim 1.

19. The organic light-emitting device of claim 18,
wherein the organic layer comprises an emission layer, and
wherein the emission layer comprises a phosphorescent dopant.

20. The organic light-emitting device of claim 18,
wherein the organic layer comprises a hole transport layer, and
wherein the hole transport layer comprises the amino fluorene polymer.

* * * * *